(12) United States Patent
Briggs et al.

(10) Patent No.: US 7,211,037 B2
(45) Date of Patent: May 1, 2007

(54) APPARATUS FOR THE CONTINUOUS SEPARATION OF BIOLOGICAL FLUIDS INTO COMPONENTS AND METHOD OF USING SAME

(75) Inventors: Dennis Briggs, West Chester, PA (US); Steve Gara, Collegeville, PA (US); Tom Watters, Malvern, PA (US); Mike Hutchinson, King of Prussia, PA (US)

(73) Assignee: Therakos, Inc., Exton, PA (US)

( * ) Notice: Subject to any disclaimer, the term of this patent is extended or adjusted under 35 U.S.C. 154(b) by 368 days.

(21) Appl. No.: 10/654,742

(22) Filed: Sep. 3, 2003

(65) Prior Publication Data
US 2004/0124157 A1 Jul. 1, 2004

Related U.S. Application Data

(63) Continuation-in-part of application No. 10/375,629, filed on Feb. 27, 2003.

(60) Provisional application No. 60/361,287, filed on Mar. 4, 2002.

(51) Int. Cl.
*B04B 7/12* (2006.01)
(52) U.S. Cl. ............... 494/44; 604/5.04; 604/6.08; 494/43; 494/67; 210/206; 210/380.1
(58) Field of Classification Search .......... 210/380.1, 210/206; 494/41, 43, 44, 67, 76, 77; 604/4.01, 604/6.01, 6.04, 5.01, 5.04, 6.08
See application file for complete search history.

(56) References Cited

U.S. PATENT DOCUMENTS

| | | | |
|---|---|---|---|
| 2,983,639 A | 5/1961 | Jageman | |
| 3,103,489 A | 9/1963 | Pickels | |
| 3,145,713 A | 8/1964 | Latham, Jr. | |
| 3,628,445 A | 12/1971 | Webster | |
| 3,678,964 A | 7/1972 | Andrews | |
| 3,861,972 A | 1/1975 | Glover et al. | |
| 3,986,442 A | 10/1976 | Khoja et al. | |
| 4,056,224 A | 11/1977 | Lolachi | |
| 4,059,108 A | 11/1977 | Latham, Jr. | |
| 4,086,924 A | 5/1978 | Latham, Jr. | |
| 4,108,353 A | 8/1978 | Brown | |
| 4,109,852 A | 8/1978 | Brown et al. | |
| 4,109,854 A | 8/1978 | Brown | |

(Continued)

FOREIGN PATENT DOCUMENTS

DE 3817664 A1 11/1989

(Continued)

OTHER PUBLICATIONS

European Search Report, dated Dec. 16, 2004, for European Appln. No. EP 0425 5326 Austrian Search Report, dated Feb. 22, 2005, for Singapore Appln. No. 200404816-1.

(Continued)

*Primary Examiner*—David A Reifsynder
(74) *Attorney, Agent, or Firm*—Todd Volyn

(57) ABSTRACT

The present invention provides an apparatus for separating components of a fluid having an outer housing containing a core wherein three separate fluid pathways are provided to allow continuous separation of biological fluids.

27 Claims, 51 Drawing Sheets

U.S. PATENT DOCUMENTS

| | | |
|---|---|---|
| 4,109,855 A | 8/1978 | Brown et al. |
| 4,111,356 A | 9/1978 | Boggs et al. |
| 4,113,173 A | 9/1978 | Lolachi |
| 4,114,802 A | 9/1978 | Brown |
| 4,120,448 A | 10/1978 | Cullis |
| 4,120,449 A | 10/1978 | Brown et al. |
| 4,164,318 A | 8/1979 | Boggs |
| 4,194,684 A | 3/1980 | Boggs |
| 4,201,525 A | 5/1980 | Brown et al. |
| 4,204,537 A | 5/1980 | Latham, Jr. |
| 4,221,322 A | 9/1980 | Drago et al. |
| 4,230,263 A | 10/1980 | Westberg |
| 4,245,383 A | 1/1981 | Boggs |
| 4,261,507 A | 4/1981 | Baumler |
| 4,285,464 A | 8/1981 | Latham, Jr. |
| 4,300,717 A | 11/1981 | Latham, Jr. |
| 4,303,193 A | 12/1981 | Latham, Jr. |
| 4,305,659 A | 12/1981 | Bilstad et al. |
| 4,309,993 A | 1/1982 | Brown |
| 4,321,919 A | 3/1982 | Edelson |
| 4,333,016 A | 6/1982 | Bilstad et al. |
| 4,344,560 A | 8/1982 | Iriguchi et al. |
| 4,372,484 A | 2/1983 | Larsson et al. |
| 4,374,731 A | 2/1983 | Brown et al. |
| 4,389,206 A | 6/1983 | Bacehowski et al. |
| 4,398,906 A | 8/1983 | Edelson |
| 4,407,295 A | 10/1983 | Steuer et al. |
| 4,417,884 A | 11/1983 | Schoendorfer et al. |
| 4,421,503 A | 12/1983 | Latham, Jr. et al. |
| 4,425,112 A | 1/1984 | Ito |
| 4,425,116 A | 1/1984 | Bilstad et al. |
| 4,428,744 A | 1/1984 | Edelson |
| 4,464,166 A | 1/1984 | Edelson |
| 4,439,178 A | 3/1984 | Mulzet |
| 4,440,195 A | 4/1984 | van Dongeren |
| 4,459,169 A | 7/1984 | Bacehowski et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,517,404 A | 5/1985 | Hughes et al. |
| 4,530,691 A | 7/1985 | Brown |
| 4,540,397 A | 9/1985 | Lolachi et al. |
| 4,573,960 A | 3/1986 | Goss |
| 4,573,962 A | 3/1986 | Troutner |
| 4,578,056 A | 3/1986 | King et al. |
| 4,605,503 A | 8/1986 | Bilstad et al. |
| 4,636,346 A | 1/1987 | Gold et al. |
| 4,680,025 A | 7/1987 | Kruger et al. |
| 4,692,136 A | 9/1987 | Feldman et al. |
| 4,708,712 A | 11/1987 | Mulzet |
| 4,710,161 A | 12/1987 | Takabayashi et al. |
| 4,724,317 A | 2/1988 | Brown et al. |
| 4,734,089 A | 3/1988 | Cullis |
| 4,737,140 A | 4/1988 | Lee et al. |
| 4,767,396 A | 8/1988 | Powers |
| 4,775,794 A | 10/1988 | Behmann |
| 4,776,964 A | 10/1988 | Schoendorfer et al. |
| 4,778,444 A | 10/1988 | Westberg et al. |
| 4,806,252 A | 2/1989 | Brown et al. |
| 4,834,890 A | 5/1989 | Brown et al. |
| 4,854,933 A | 8/1989 | Mull |
| 4,857,190 A | 8/1989 | Wada et al. |
| 4,859,333 A | 8/1989 | Panzani |
| 4,865,081 A | 9/1989 | Neumann et al. |
| 4,866,282 A | 9/1989 | Miripol et al. |
| 4,876,014 A | 10/1989 | Malson |
| 4,879,031 A | 11/1989 | Panzani |
| 4,889,524 A | 12/1989 | Fell et al. |
| 4,898,571 A | 2/1990 | Epper et al. |
| 4,911,833 A | 3/1990 | Schoendorfer et al. |
| 4,940,543 A | 7/1990 | Brown et al. |
| 4,943,273 A | 7/1990 | Pages |
| 4,950,401 A | 8/1990 | Unger et al. |
| D312,128 S | 11/1990 | Headley |
| 4,983,158 A | 1/1991 | Headley |
| 4,986,442 A | 1/1991 | Hinterreiter |
| 4,997,577 A | 3/1991 | Stewart |
| 5,039,401 A | 8/1991 | Columbus et al. |
| 5,053,127 A | 10/1991 | Schoendorfer et al. |
| 5,061,381 A | 10/1991 | Burd |
| 5,076,911 A | 12/1991 | Brown et al. |
| 5,078,671 A | 1/1992 | Dennehey et al. |
| 5,097,870 A | 3/1992 | Williams |
| 5,100,372 A | 3/1992 | Headley |
| 5,104,526 A | 4/1992 | Brown et al. |
| 5,147,290 A | 9/1992 | Jonsson |
| 5,160,310 A | 11/1992 | Yhland |
| 5,186,844 A | 2/1993 | Burd et al. |
| 5,217,426 A | 6/1993 | Bacehowski et al. |
| 5,217,427 A | 6/1993 | Cullis |
| 5,224,921 A | 7/1993 | Dennehey et al. |
| 5,240,614 A | 8/1993 | Ofsthun et al. |
| 5,254,248 A | 10/1993 | Nakamura |
| 5,273,517 A | 12/1993 | Barone et al. |
| 5,281,342 A | 1/1994 | Biesel et al. |
| 5,298,171 A | 3/1994 | Biesel |
| 5,305,799 A | 4/1994 | Dal Palu |
| 5,316,666 A | 5/1994 | Brown et al. |
| 5,316,667 A | 5/1994 | Brown |
| 5,322,620 A | 6/1994 | Brown et al. |
| 5,332,500 A | 7/1994 | Seureau et al. |
| 5,360,542 A | 11/1994 | Williamson, IV et al. |
| 5,362,291 A | 11/1994 | Williamson, IV |
| 5,370,802 A | 12/1994 | Brown |
| 5,372,136 A | 12/1994 | Steuer et al. |
| 5,405,308 A | 4/1995 | Headley et al. |
| 5,427,509 A | 6/1995 | Chapman et al. |
| 5,427,695 A | 6/1995 | Brown |
| 5,437,598 A | 8/1995 | Antwiler |
| 5,443,451 A | 8/1995 | Chapman et al. |
| 5,445,506 A | 8/1995 | Afflerbaugh et al. |
| 5,445,593 A | 8/1995 | Biesel et al. |
| 5,460,493 A | 10/1995 | Deniega et al. |
| 5,462,416 A | 10/1995 | Dennehey et al. |
| 5,480,294 A | 1/1996 | Di Perna et al. |
| 5,482,440 A | 1/1996 | Dennehey et al. |
| 5,494,578 A | 2/1996 | Brown et al. |
| 5,494,592 A | 2/1996 | Lathan, Jr. et al. |
| 5,501,840 A | 3/1996 | Mantovani et al. |
| 5,505,685 A | 4/1996 | Antwiler |
| 5,514,069 A | 5/1996 | Brown et al. |
| 5,514,070 A | 5/1996 | Pages |
| 5,525,218 A | 6/1996 | Williamson, IV et al. |
| 5,527,467 A | 6/1996 | Ofsthun et al. |
| 5,527,472 A | 6/1996 | Bellotti et al. |
| 5,529,691 A | 6/1996 | Brown |
| 5,538,405 A | 7/1996 | Patno et al. |
| 5,549,834 A | 8/1996 | Brown |
| 5,551,942 A | 9/1996 | Brown et al. |
| 5,573,678 A | 11/1996 | Brown et al. |
| 5,591,113 A | 1/1997 | Darnell et al. |
| 5,591,643 A | 1/1997 | Schembri |
| 5,607,579 A | 3/1997 | Latham, Jr. et al. |
| 5,628,915 A | 5/1997 | Brown et al. |
| 5,632,893 A | 5/1997 | Brown et al. |
| 5,634,893 A | 6/1997 | Rishton |
| 5,637,082 A | 6/1997 | Pages et al. |
| 5,639,382 A | 6/1997 | Brown |
| 5,641,414 A | 6/1997 | Brown |
| 5,641,622 A | 6/1997 | Lake et al. |
| 5,643,193 A | 7/1997 | Papillon et al. |
| 5,649,905 A | 7/1997 | Zanger et al. |
| 5,651,766 A | 7/1997 | Kingsley et al. |
| 5,653,887 A | 8/1997 | Wahl et al. |

| | | | | | | |
|---|---|---|---|---|---|---|
| 5,656,163 | A | 8/1997 | Brown | 6,273,849 | B1 | 8/2001 | Scherer |
| 5,676,841 | A | 10/1997 | Brown | 6,296,450 | B1 | 10/2001 | Westberg et al. |
| 5,681,273 | A | 10/1997 | Brown | 6,312,593 | B1 | 11/2001 | Petrie |
| 5,690,602 | A | 11/1997 | Brown et al. | 6,312,607 | B1 | 11/2001 | Brown et al. |
| 5,690,835 | A | 11/1997 | Brown | 6,315,707 | B1 | 11/2001 | Smith et al. |
| 5,693,232 | A | 12/1997 | Brown et al. | 6,319,223 | B1 | 11/2001 | Wortrich et al. |
| 5,702,357 | A | 12/1997 | Bainbridge et al. | 6,322,488 | B1 | 11/2001 | Westberg et al. |
| 5,704,887 | A | 1/1998 | Slowik et al. | 6,334,842 | B1 | 1/2002 | Hlavinka et al. |
| 5,728,060 | A | 3/1998 | Kingsley | 6,346,069 | B1 | 2/2002 | Collier |
| 5,730,883 | A | 3/1998 | Brown | 6,348,031 | B1 | 2/2002 | Unger et al. |
| 5,738,644 | A | 4/1998 | Holmes et al. | 6,348,156 | B1 | 2/2002 | Vishnoi et al. |
| 5,738,784 | A | 4/1998 | Holm et al. | 6,352,499 | B1 | 3/2002 | Geigle |
| 5,746,708 | A | 5/1998 | Giesler et al. | 6,379,322 | B1 | 4/2002 | Kingsley |
| 5,750,039 | A | 5/1998 | Brown | 6,387,263 | B1 | 5/2002 | Bhaskar et al. |
| 5,759,147 | A | 6/1998 | Bacehowski et al. | 6,464,624 | B2 | 10/2002 | Pages |
| 5,759,413 | A | 6/1998 | Brown | 6,475,132 | B2 | 11/2002 | Zettier |
| 5,769,811 | A | 6/1998 | Stacey et al. | 6,491,656 | B1 | 12/2002 | Morris |
| 5,779,660 | A | 7/1998 | Kingsley et al. | 6,495,366 | B1 | 12/2002 | Briggs |
| 5,785,869 | A | 7/1998 | Martinson et al. | 6,511,411 | B1 | 1/2003 | Brown |
| 5,792,372 | A | 8/1998 | Brown et al. | 6,514,189 | B1 | 2/2003 | Hlavinka et al. |
| 5,804,079 | A | 9/1998 | Brown | 6,524,231 | B1 | 2/2003 | Westberg et al. |
| 5,807,492 | A | 9/1998 | Brown et al. | 6,544,162 | B1 | 4/2003 | Van Wie et al. |
| 5,833,866 | A | 11/1998 | Brown | 6,544,416 | B2 | 4/2003 | Helwig |
| 5,849,203 | A | 12/1998 | Brown et al. | 6,554,788 | B1 | 4/2003 | Hunley et al. |
| 5,855,773 | A | 1/1999 | Lasota | 6,558,307 | B2 | 5/2003 | Headley |
| 5,868,695 | A | 2/1999 | Wolf, Jr. et al. | 6,579,219 | B2 | 6/2003 | Dolecek et al. |
| 5,870,805 | A | 2/1999 | Kandler et al. | 6,582,349 | B1 | 6/2003 | Cantu et al. |
| 5,906,598 | A | 5/1999 | Giesler et al. | 6,582,350 | B2 | 6/2003 | Dolecek |
| 5,916,743 | A | 6/1999 | Lake et al. | 6,589,153 | B2 | 7/2003 | Dolecek et al. |
| 5,919,125 | A | 7/1999 | Berch | 6,589,155 | B2 | 7/2003 | Dolecek |
| 5,921,909 | A | 7/1999 | Gustafsson | 6,596,179 | B2 | 7/2003 | Giesler et al. |
| 5,935,051 | A | 8/1999 | Bell | 6,596,180 | B2 | 7/2003 | Baugh et al. |
| 5,945,291 | A | 8/1999 | Bolton et al. | 6,596,181 | B2 | 7/2003 | Dolecek et al. |
| 5,948,271 | A | 9/1999 | Wardwell et al. | 6,605,223 | B2 | 8/2003 | Jorgensen et al. |
| 5,951,509 | A | 9/1999 | Morris | 6,607,473 | B2 | 8/2003 | Collier |
| 5,958,250 | A | 9/1999 | Brown et al. | 6,610,002 | B2 | 8/2003 | Dolecek |
| 5,961,842 | A | 10/1999 | Min et al. | 6,612,975 | B2 | 9/2003 | Malcom et al. |
| 5,976,388 | A | 11/1999 | Carson | 6,616,589 | B1 | 9/2003 | Maehans |
| 5,980,757 | A | 11/1999 | Brown et al. | 6,709,377 | B1 | 3/2004 | Rochat |
| 5,980,760 | A | 11/1999 | Min et al. | 2001/0000185 | A1 | 4/2001 | Keller et al. |
| 5,989,177 | A | 11/1999 | West et al. | 2001/0004444 | A1 | 6/2001 | Haser et al. |
| 5,993,370 | A | 11/1999 | Brown et al. | 2001/0024623 | A1 | 9/2001 | Grimm et al. |
| 5,996,634 | A | 12/1999 | Dennehey et al. | 2002/0032112 | A1 | 3/2002 | Pages |
| 6,007,509 | A | 12/1999 | Kingsley et al. | 2002/0068674 | A1 | 6/2002 | Hlavinka et al. |
| 6,007,725 | A | 12/1999 | Brown | 2002/0068675 | A1 | 6/2002 | Felt et al. |
| 6,027,655 | A | 2/2000 | Holm | 2002/0091057 | A1 | 7/2002 | Westberg et al. |
| 6,027,657 | A | 2/2000 | Min et al. | 2002/0099319 | A1 | 7/2002 | Saito et al. |
| 6,056,522 | A | 5/2000 | Johnson | 2002/0142909 | A1 | 10/2002 | Sakota |
| 6,059,979 | A | 5/2000 | Brown | 2002/0147094 | A1 | 10/2002 | Dolecek |
| 6,071,421 | A | 6/2000 | Brown | 2003/0085185 | A1 | 5/2003 | Kouba |
| 6,071,423 | A | 6/2000 | Brown et al. | 2003/0094425 | A1 | 5/2003 | Brandt et al. |
| 6,080,322 | A | 6/2000 | Deniega et al. | 2003/0102272 | A1 | 6/2003 | Brown |
| 6,102,883 | A | 8/2000 | Kingsley et al. | 2003/0106858 | A1 | 6/2003 | Sharpe |
| 6,123,655 | A | 9/2000 | Fell | 2003/0114289 | A1 | 6/2003 | Merino et al. |
| 6,129,656 | A | 10/2000 | Blakeslee et al. | 2003/0116506 | A1 | 6/2003 | Lane |
| 6,168,561 | B1 | 1/2001 | Cantu et al. | 2003/0116512 | A1 | 6/2003 | Antwiler et al. |
| 6,179,801 | B1 | 1/2001 | Holmes et al. | 2003/0136739 | A1 | 7/2003 | Kirkland et al. |
| 6,183,407 | B1 | 2/2001 | Hallgren et al. | 2003/0146170 | A1 | 8/2003 | Corbin, III et al. |
| 6,183,651 | B1 | 2/2001 | Brown et al. | 2003/0155312 | A1 | 8/2003 | Ivansons et al. |
| 6,186,752 | B1 | 2/2001 | Deniega et al. | 2003/0173274 | A1 | 9/2003 | Corbin, III et al. |
| 6,196,987 | B1 | 3/2001 | Holmes et al. | 2003/0181305 | A1* | 9/2003 | Briggs et al. ................. 494/37 |
| 6,197,202 | B1 | 3/2001 | Brown | | | | |
| 6,200,287 | B1 | 3/2001 | Keller et al. | | | FOREIGN PATENT DOCUMENTS | |
| 6,204,058 | B1 | 3/2001 | Bolton | | | | |
| 6,207,063 | B1 | 3/2001 | Brown | DE | | 4220232 A1 | 9/1994 |
| 6,219,584 | B1 | 4/2001 | Lee | EP | | 112990 A2 | 3/1984 |
| 6,228,017 | B1 | 5/2001 | Brown | EP | | 268025 B1 | 5/1988 |
| 6,231,537 | B1 | 5/2001 | Holmes et al. | EP | | 0297216 | 1/1989 |
| 6,234,989 | B1 | 5/2001 | Brierton et al. | EP | | 608519 A2 | 8/1994 |
| 6,248,053 | B1 | 6/2001 | Ehnstrom et al. | EP | | 749771 A2 | 12/1996 |
| 6,251,056 | B1 | 6/2001 | Berger et al. | EP | | 755708 A2 | 1/1997 |
| 6,261,065 | B1 | 7/2001 | Nayak et al. | EP | | 779077 A1 | 6/1997 |
| 6,261,217 | B1 | 7/2001 | Unger et al. | EP | | 0786324 | 7/1997 |

| | | | |
|---|---|---|---|
| EP | 799645 A1 | 10/1997 |
| EP | 0992256 | 4/2000 |
| EP | 1043071 A1 | 10/2000 |
| EP | 1066842 A2 | 1/2001 |
| EP | 1138392 A2 | 10/2001 |
| EP | 1208856 | 5/2002 |
| EP | 1241249 A1 | 9/2002 |
| EP | 1252918 A2 | 10/2002 |
| FR | 2305238 A1 | 9/1978 |
| JP | 09192215 | 7/1997 |
| JP | 2001/070832 | 9/1999 |
| WO | WO 93/12887 A1 | 7/1993 |
| WO | WO 94/08687 A1 | 4/1994 |
| WO | WO 94/08688 A1 | 4/1994 |
| WO | WO 94/29722 A1 | 12/1994 |
| WO | WO 96/25234 A1 | 8/1996 |
| WO | WO 97/36581 | 10/1997 |
| WO | WO 97/36634 | 10/1997 |
| WO | WO 98/22163 | 5/1998 |
| WO | WO 98/48938 A1 | 11/1998 |
| WO | WO 99/02269 A1 | 1/1999 |
| WO | WO 99/23471 A1 | 5/1999 |
| WO | WO 01/17651 A1 | 3/2001 |
| WO | WO 01/17653 A1 | 3/2001 |
| WO | WO 01/24848 A1 | 4/2001 |
| WO | WO 02/40176 A1 | 5/2002 |
| WO | WO 03/000026 A2 | 1/2003 |
| WO | WO 03/013686 A1 | 2/2003 |

OTHER PUBLICATIONS

European Search Report, dated Sep. 26, 2006, for European Appln. No. EP04255327.

* cited by examiner

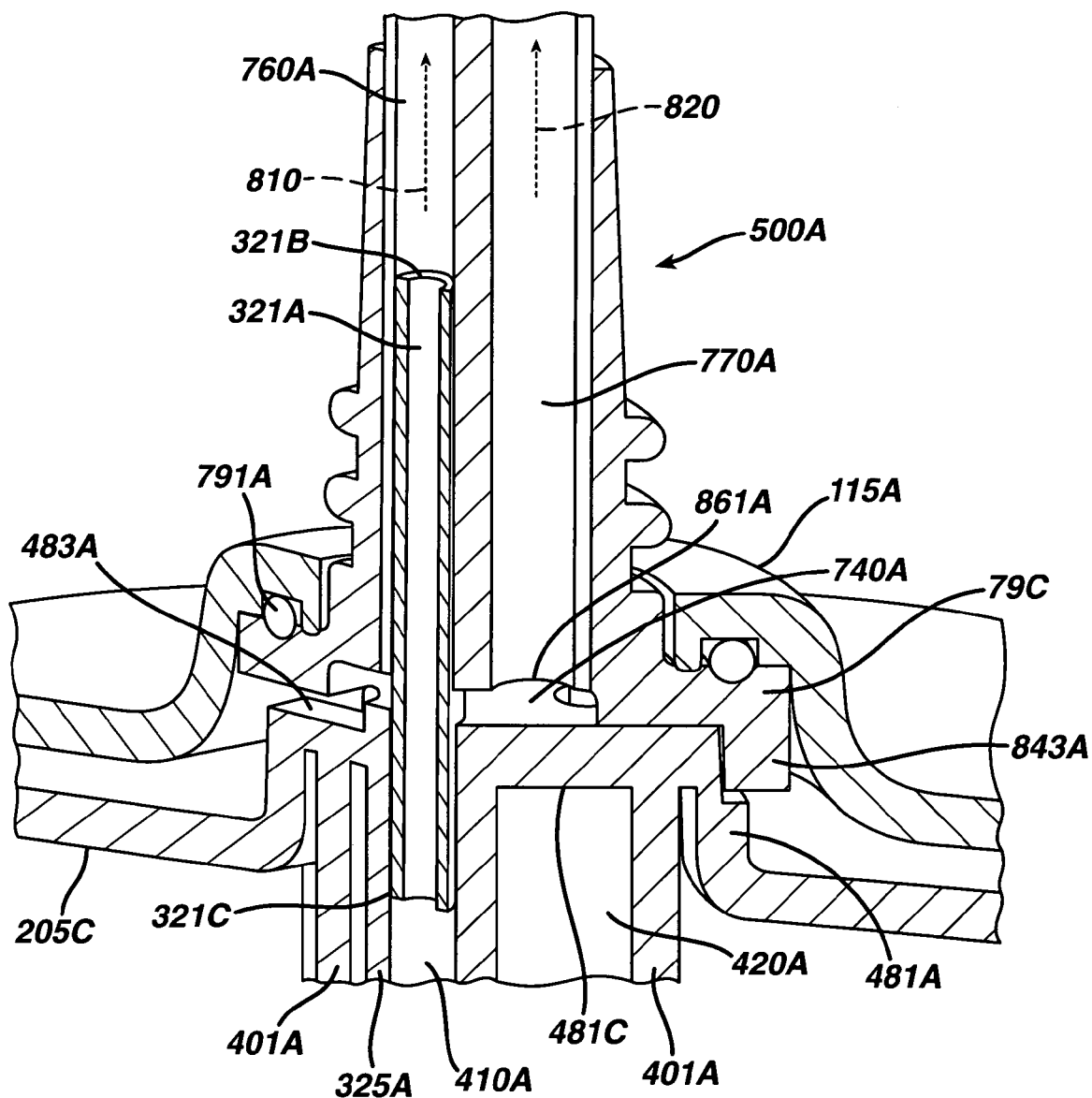

APPARATUS FOR THE CONTINUOUS SEPARATION OF BIOLOGICAL FLUIDS INTO COMPONENTS AND METHOD OF USING SAME

CROSS-REFERENCE TO RELATED APPLICATIONS

This application is a continuation-in-part application of U.S. patent application Ser. No. 10/375,629, filed Feb. 27, 2003, which claims the benefit of U.S. Provisional Application, Ser. No. 60/361,287, filed Mar. 4, 2002, both of which are hereby incorporated by reference in their entireties.

TECHNICAL FIELD OF THE INVENTION

The present invention generally relates to methods and apparatus for separating a fluid into its components, for example, a biological or sensitive fluid such as blood, and specifically to methods and apparatus that use centrifugal force to separate a fluid into its components by density so as to improve the component yield.

BACKGROUND ART

With the advance of medical sciences, it has become possible to treat a patient's blood in closed-loop processes, returning the patient's own treated blood back to him in one medical treatment. An example of such processes include external treatment methods for diseases in which there is a pathological increase of lymphocytes, such as cutaneous T-cell lymphoma or other diseases affecting white blood cells. In such methods, the patient's blood is irradiated with ultraviolet light in the presence of a chemical or an antibody. Ultraviolet light affects the bonding between the lymphocytes and the chemical or antibody that inhibits the metabolic processes of the lymphocytes.

During one of these medical treatments, a centrifuge bowl, such as, for example, a Latham bowl, as shown in U.S. Pat. No. 4,303,193, expressly incorporated by reference in its entirety herein, separates blood into red blood cells ("RBCs") and buffy coat. The Latham bowl is a blood component separator that has been used for some time in the medical apheresis market as well as in innovative medical therapies such as extracorporeal photopheresis (ECP). PCT Applications WO 97/36581 and WO 97/36634, and U.S. Pat. Nos. 4,321,919; 4,398,906; 4,428,744; and 4,464,166 provide descriptions of extracorporeal photopheresis, and are hereby expressly incorporated by reference in their entirety.

The Latham bowl efficiency is often measured by the white blood cell ("WBC") "yield," which is typically about 50%. Yield is defined as the percentage of cells collected versus the number processed. When compared to other types of whole blood separators, this high yield enables the Latham bowl separator to collect much larger volumes of WBCs while processing much less whole blood from the donor patient. However, a major drawback to the Latham bowl separator is that the separation process must be repeatedly stopped to remove the packed RBCs and plasma once they fill the inside of the bowl, creating a "batch-type" process. Although the Latham bowl separator has a high volume yield, the constant filling and emptying of this bowl wastes time; thus, the process is considered less efficient with respect to time. Additionally, the Latham bowl requires a rotating seal, which is expensive and difficult to manufacture.

An additional drawback of centrifugal processing apparatus has been their high cost of manufacture due to strict tolerances, rotating seals, and extensive manufacturing processes.

DISCLOSURE OF THE INVENTION

The present invention provided an apparatus for separating components of a fluid comprising: an outer housing with an upper housing end and a lower housing end, wherein said outer housing increases in diameter from said upper housing end to said lower housing end, said lower housing end having a housing floor and said housing upper end having a housing outlet, said outer housing adapted for rotation about a center axis; said outer housing containing a core in said interior volume; the core having an outer wall, an upper core end, and a lower core end; said core connected with said outer housing for rotation therewith; and providing a separation volume between said core and said outer housing; said core end having a lumen connector and a lumen connector top surface; a first lumen for providing fluid communication from the housing outlet through the lumen connector and then radially outward through the core to the fluid separation volume; a second lumen providing fluid communications from the housing outlet extending axially along center axis to housing floor; a connection sleeve which forms with the lumen connector a chamber and provide fluid communications between the housing outlet and the separation volume.

In another embodiment of the present invention is provided a method for separating components of a fluid into a higher density component and a lower density component comprising: providing a centrifuge bowl have a first bowl channel, a second bowl channel, and a bowl chamber; flowing said fluid from a source into said centrifuge bowl through said first bowl channel; rotating said centrifuge bowl about an axis; removing said higher density component from said bowl via said second bowl channel; and removing said lower density component from said bowl via said bowl chamber.

BRIEF DESCRIPTION OF THE DRAWINGS

The invention is described in detail with respect to the accompanying drawings, which illustrate an embodiment of the inventive apparatus, assemblies, systems, and methods.

FIG. 39A shows a cross sectional view of a connection sleeve in place with a lumen connector of the bowl of FIG. 38 along the line XX.

MODES FOR CARRYING OUT THE INVENTION

Features of the present invention are embodied in the permanent blood driving equipment, the disposable photopheresis kit, the various devices which make up the disposable kit, and the corresponding treatment process. The following written description is outlined as follows:

I. Disposable Photopheresis Kit
  A. Cassette for Controlling Fluid Flow
    1. Filter Assembly
  B. Irradiation Chamber
  C. Centrifuge Bowl
    1. Drive Tube
II. Permanent Tower System
  A Photoactivation Chamber
  B. Centrifuge Chamber
  C. Fluid Flow Control Deck
    1. Cassette Clamping Mechanism
    2. Self-Loading Peristaltic Pumps
  D. Infra-Red Communication
III. Photopheresis Treatment Process The above-outline is included to facilitate understanding of the features of the present invention. The outline is not limiting of the present invention and is not intended to categorize or limit any aspect of the invention. The inventions are described and illustrated in sufficient detail that those skilled in this art can readily make and use them. However, various alternatives, modifications, and improvements should become readily apparent without departing from the spirit and scope of the invention. Specifically, while the invention is described in the context of a disposable kit and permanent blood drive system for use in photopheresis therapy, certain aspects of the invention are not so limited and are applicable to kits and systems used for rendering other therapies, such as apheresis or any other extracorporeal blood treatment therapy.

I. Disposable Photopheresis Kit

Figure 1:
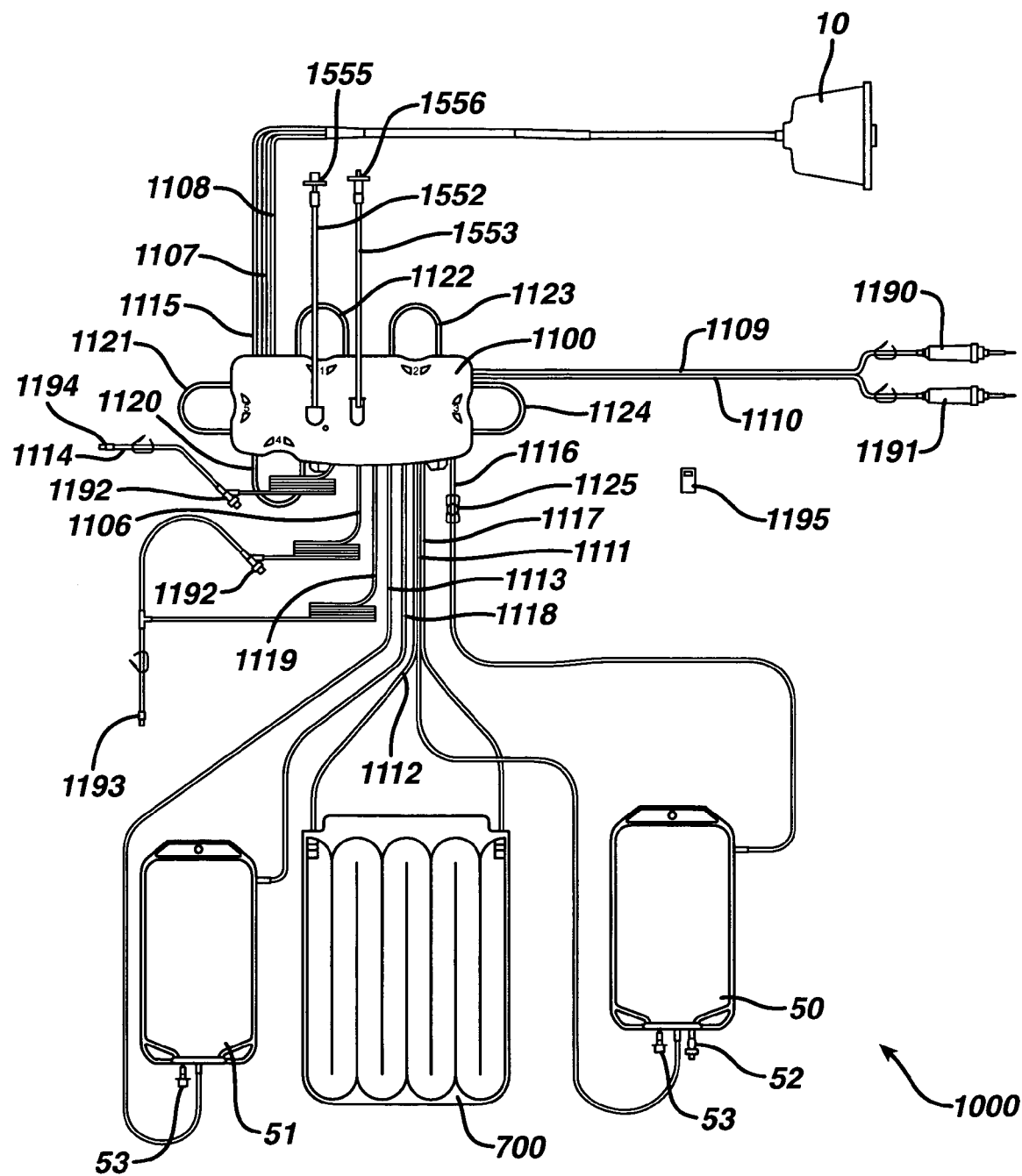
FIG. 1 is a schematic representation of an embodiment of a disposable kit for use in photopheresis therapy embodying features of the present invention.
Figure 17:
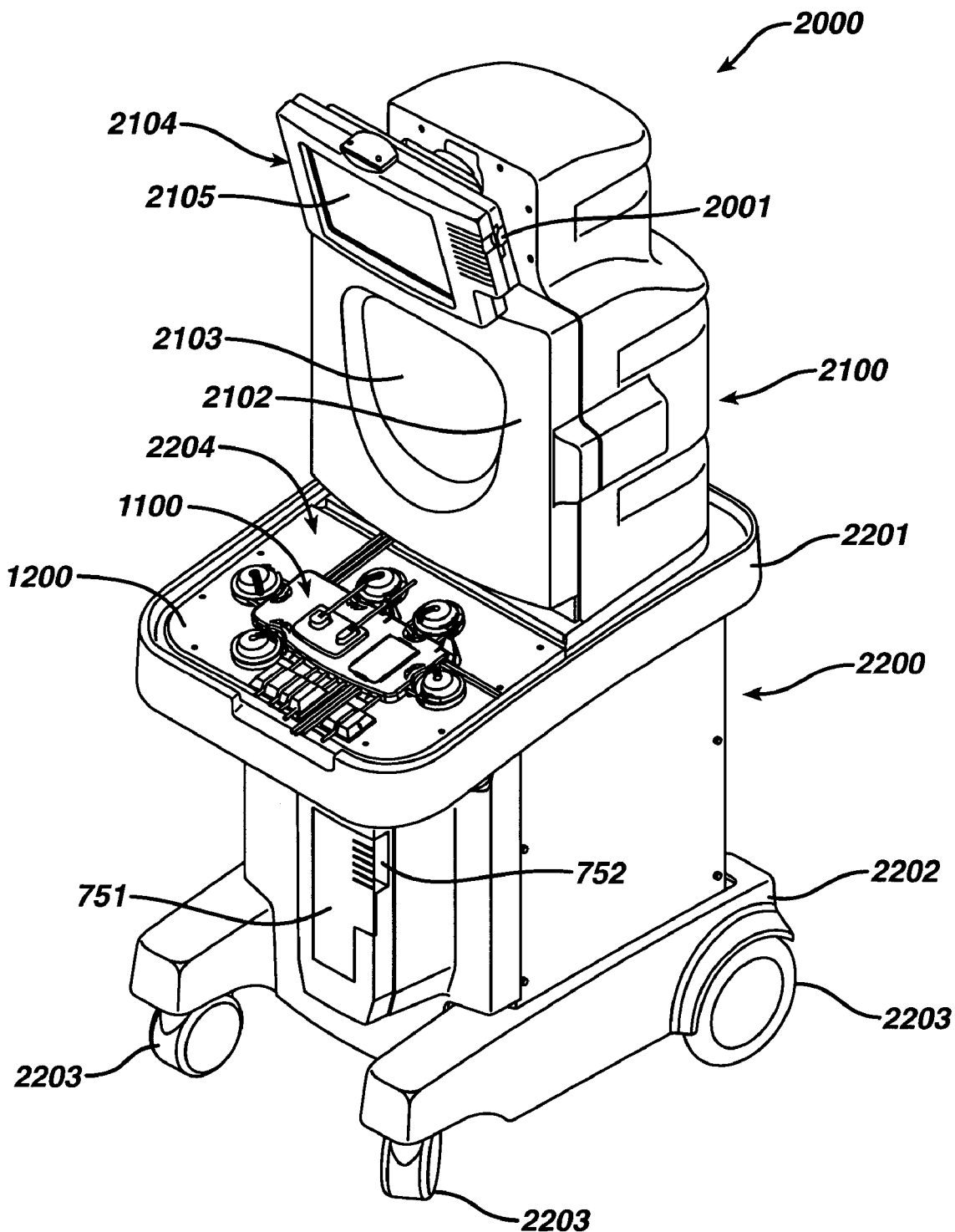
FIG. 17 is an elevated perspective view of an embodiment of a permanent tower system for use in conjunction with a disposable kit for facilitating a photopheresis therapy session.

FIG. 1 illustrates disposable photopheresis kit 1000 embodying features of the present invention. It is necessary that a new disposable sterile kit be used for each therapy session. In order to facilitate the circulation of fluids through photopheresis kit 1000, and to treat blood fluids circulating therethrough, photopheresis kit 1000 is installed in permanent tower system 2000 (FIG. 17). The installation of photopheresis kit 1000 into tower system 2000 is described in detail below.

Photopheresis kit 1000 comprises cassette 1100, centrifuge bowl 10, irradiation chamber700, hematocrit sensor 1125, removable data card 1195, treatment bag 50, and plasma collection bag 51. Photopheresis kit 1000 further comprises saline connector spike 1190 and anticoagulant connector spike 1191 for respectively connecting saline and anticoagulant fluid bags (not shown). Photopheresis kit 1000 has all the necessary tubing and connectors to fluidly connect all devices and to route the circulation of fluids during a photopheresis treatment session. All tubing is sterile medical grade flexible tubing. Triport connectors 1192 are provided at various positions for the introduction of fluids into the tubing if necessary.

Needle adapters 1193 and 1194 are provided for respectively connecting photopheresis kit 1000 to needles for drawing whole blood from a patient and returning blood fluids to the patient. Alternatively, photopheresis kit 1000 can be adapted to use a single needle to both draw whole blood from the patient and return blood fluids to the patient. However, a two needle kit is preferred because of the ability to simultaneously draw whole blood and return blood fluids to the patient. When a patient is hooked up to photopheresis kit 1000, a closed loop system is formed.

Figure 10:
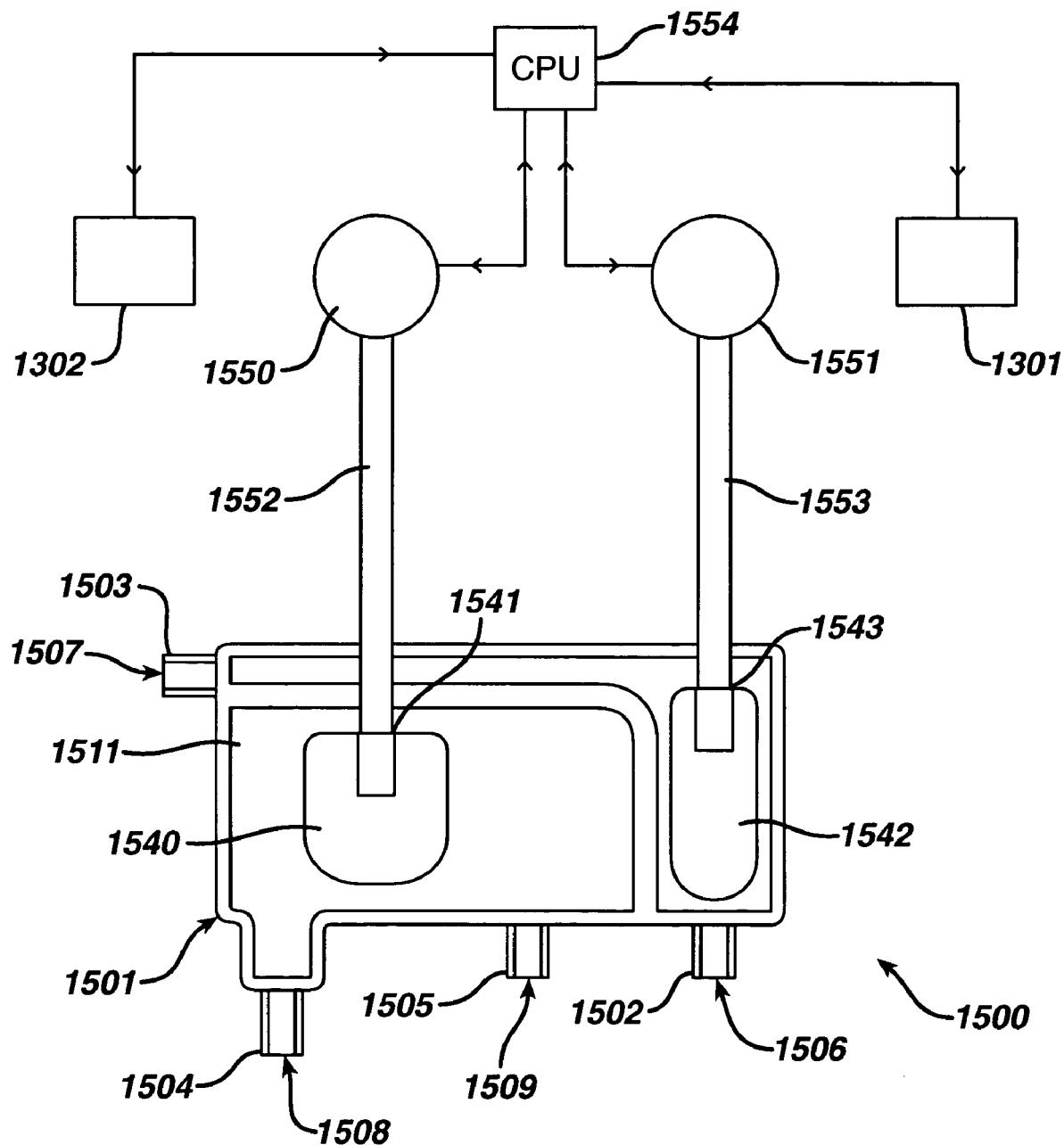
FIG. 10 is schematic representation of the filter assembly of FIG. 6 coupled to pressure sensors and a data processor.

Cassette 1100 acts both as a tube organizer and a fluid flow router. Irradiation chamber 700 is used to expose blood fluids to UV light. Centrifuge bowl 10 separates whole blood into its different components according to density. Treatment bag 50 is a 1000 mL three port bag. Straight bond port 52 is used to inject a photoactivatable or photosensitive compound into treatment bag 50. Plasma collection bag 51 is 1000 mL two port bag. Both treatment bag 50 and plasma collection bag 51 have a hinged cap spike tube 53 which can be used for drainage if necessary. Photopheresis kit 1000 further comprises hydrophobic filters 1555 and 1556 which are adapted to connect to pressure transducers 1550 and 1551 to filter 1500 via vent tubes 1552 and 1553 for monitoring and controlling the pressures within tubes connecting the patient (FIG. 10). Monitoring the pressure helps ensure that the kit is operating within safe pressure limits. The individual devices of photopheresis kit 1000, and their functioning, are discussed below in detail.

A. Cassette for Controlling Fluid Flow

Figure 2:
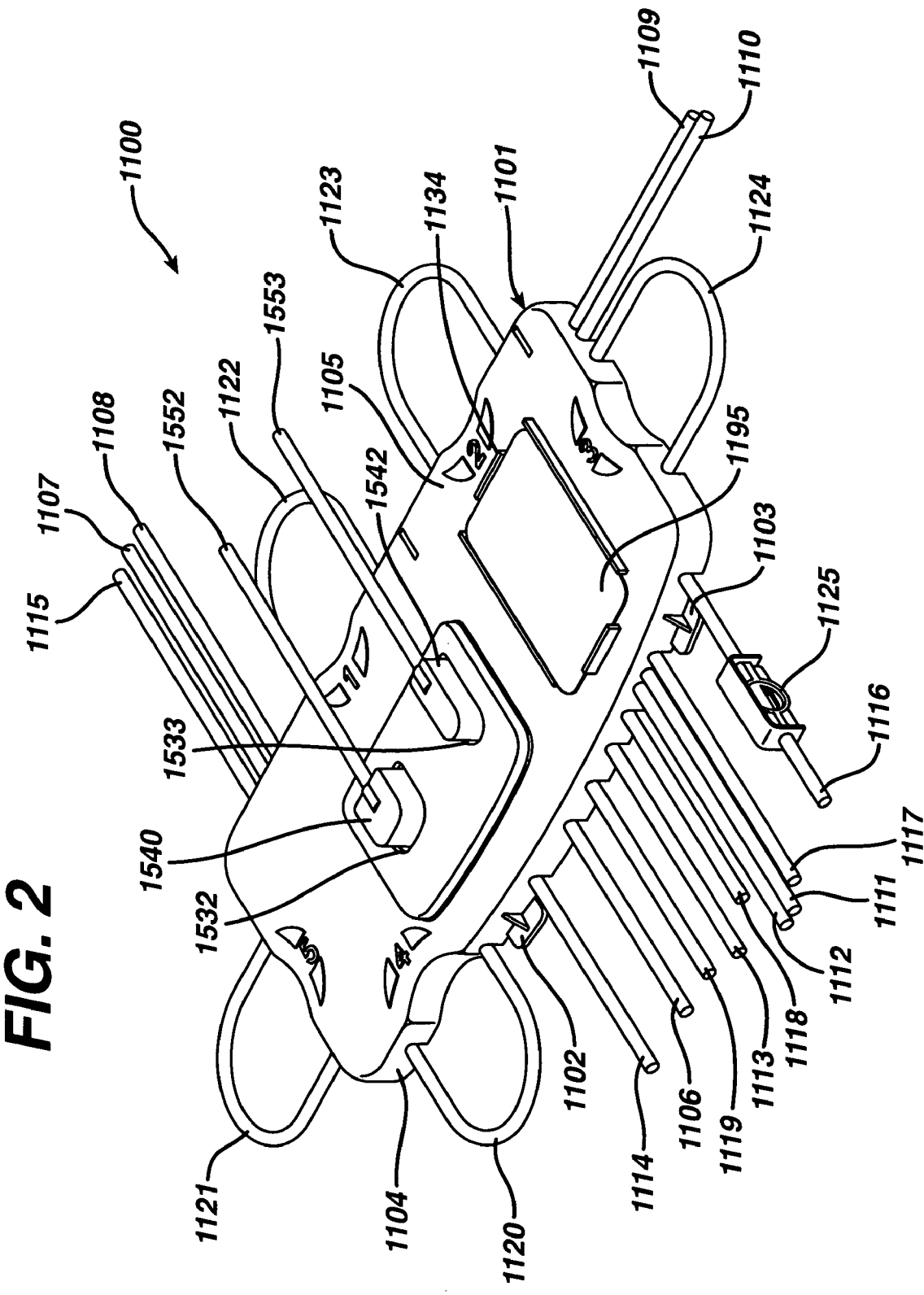
FIG. 2 is an elevated perspective view of an embodiment of a cassette for controlling fluid flow in the disposable photopheresis kit of FIG. 1.
Figure 25:
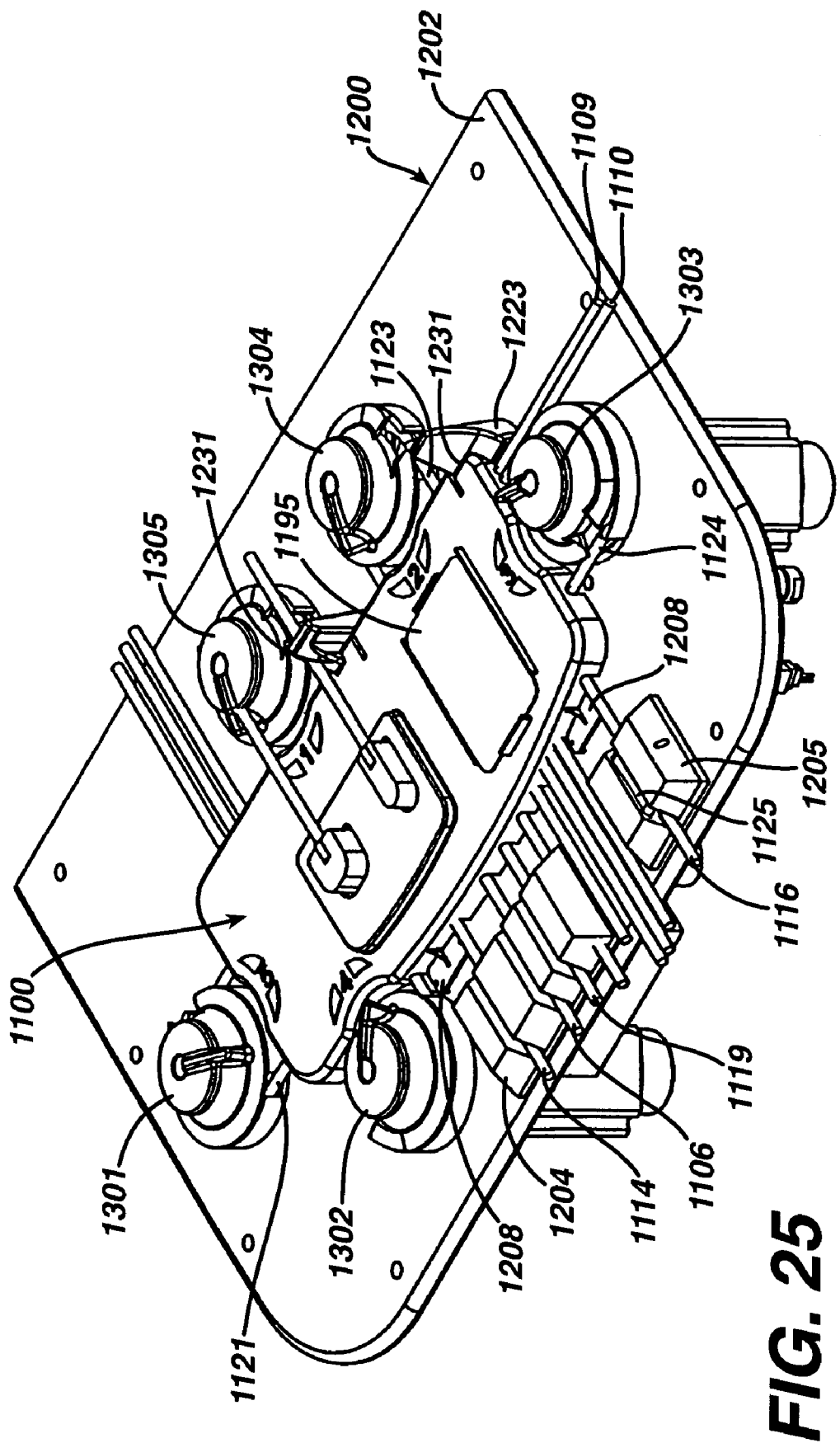
FIG. 25 is a top perspective view of the control deck of FIG. 22 with the cassette of FIG. 2 loaded thereon.

FIG. 2 shows a top perspective view of a disposable cassette 1100 for valving, pumping, and controlling the movement of blood fluids during a photopheresis treatment session. Cassette 1100 has housing 1101 that forms an internal space that acts as a casing for its various internal components and tubular circuitry. Housing 1101 is preferably made of hard plastic, but can be made of any suitably rigid material. Housing 1101 has side wall 1104 and top surface 1105. Side wall 1104 of housing 1101 has tabs 1102 and 1103 extending therefrom. During a photopheresis treatment, cassette 1100 needs to be secured to deck 1200 of tower system 2000, as is best illustrated in FIG. 25. Tabs 1102 and 1103 help position and secure cassette 1100 to deck 1200.

Figure 27:
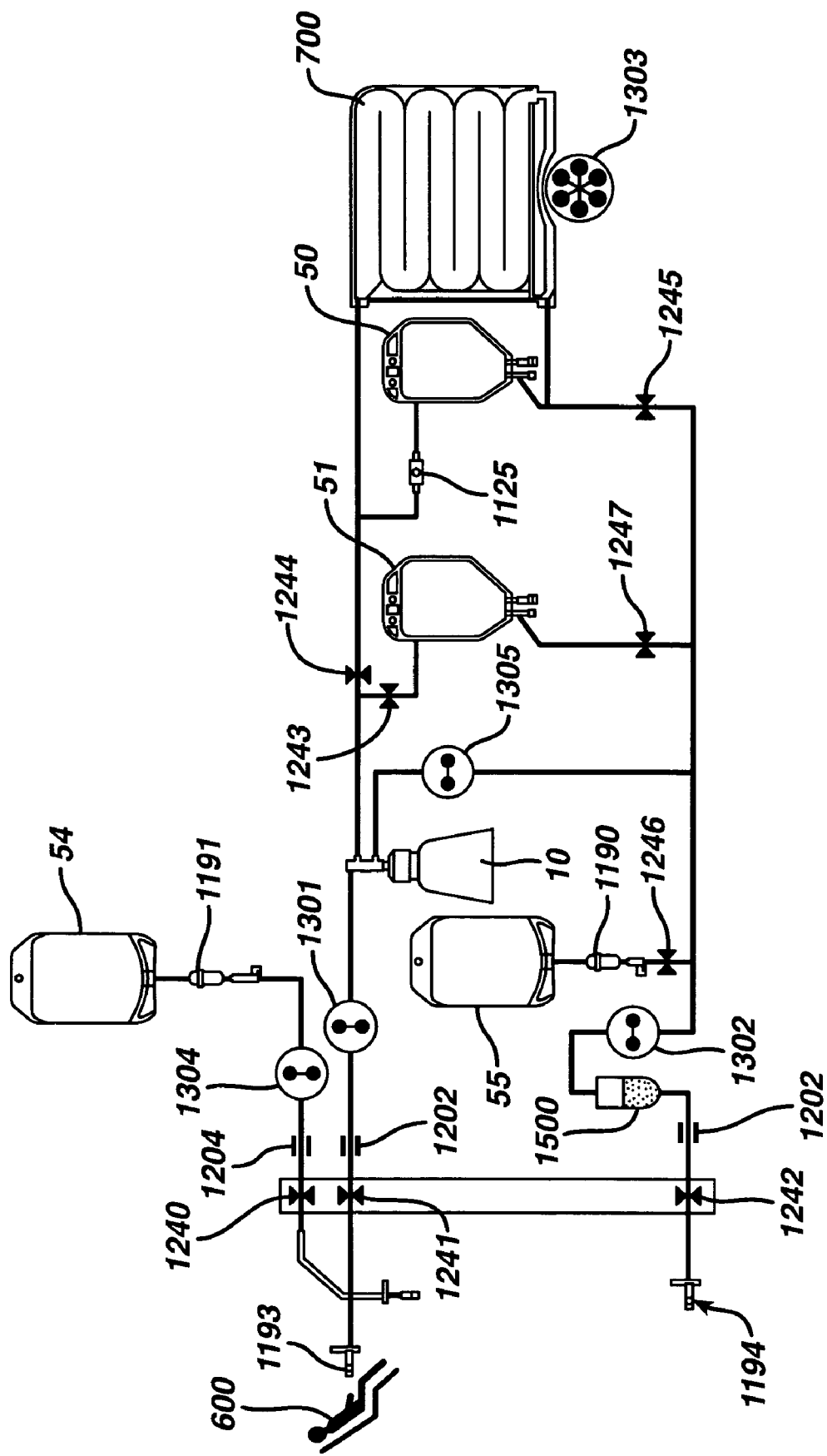
FIG. 27 is a schematic of an embodiment of the fluid flow circuit used in performing the treatment process of FIG. 26.

Cassette 1100 has fluid inlet tubes 1106, 1107, 1108, 1109, 1110, 1111, and 1112 for receiving fluids into cassette 1100, fluid outlet tubes 1114, 1115, 1116, 1117, 1118, and 1119 for expelling fluids from cassette 1100, and fluid inlet/outlet tube 1113 that can be used for both introducing and expelling fluids into and out of cassette 1100. These fluid input and output tubes fluidly couple cassette 1100 to a patient being treated, as well as the various devices of photopheresis kit 1000, such as centrifuge bowl 10, irradiation chamber700, treatment bag 50, plasma collection bag 51, and bags containing saline, anticoagulation fluid to form a closed-loop extracorporeal fluid circuit (FIG. 27).

Figure 4:
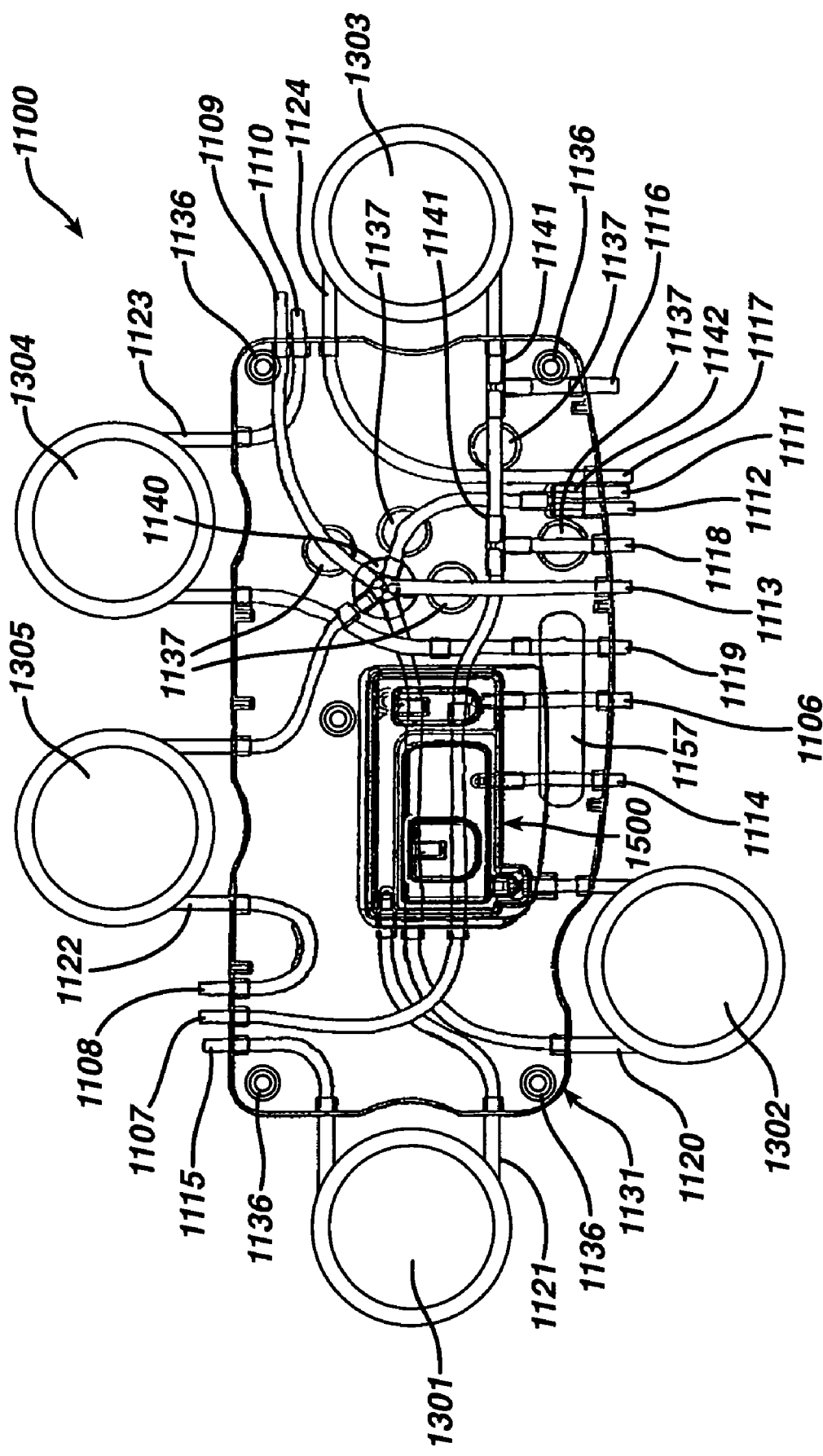
FIG. 4 is a top view of the cassette of FIG. 2 with the cover removed and showing internal tubular circuitry.

Pump tube loops 1120, 1121, 1122, 1123, and 1124 protrude from side wall 1104 of housing 1101. Pump tube loops 1120, 1121, 1122, 1123, and 1124 are provided for facilitating the circulation of fluids throughout photopheresis kit 1000 during therapy. More specifically, when cassette 1100 is secured to deck 1200 for operation, each one of said pump tube loops 1120, 1121, 1122, 1123, and 1124 are loaded into a corresponding peristaltic pump 1301, 1302, 1303, 1304, and 1305 (FIG. 4). Peristaltic pumps 1301, 1302, 1303, 1304, and 1305 drive fluid through the respective pump tube loops 1120, 1121, 1122, 1123, and 1124 in a predetermined direction, thereby driving fluid through photopheresis kit 1000 (FIG. 1) as necessary. The operation and automatic loading and unloading of peristaltic pumps 1301, 1302, 1303, 1304, and 1305 is discussed in detail below with respect to FIGS. 28-33.

Figure 3:
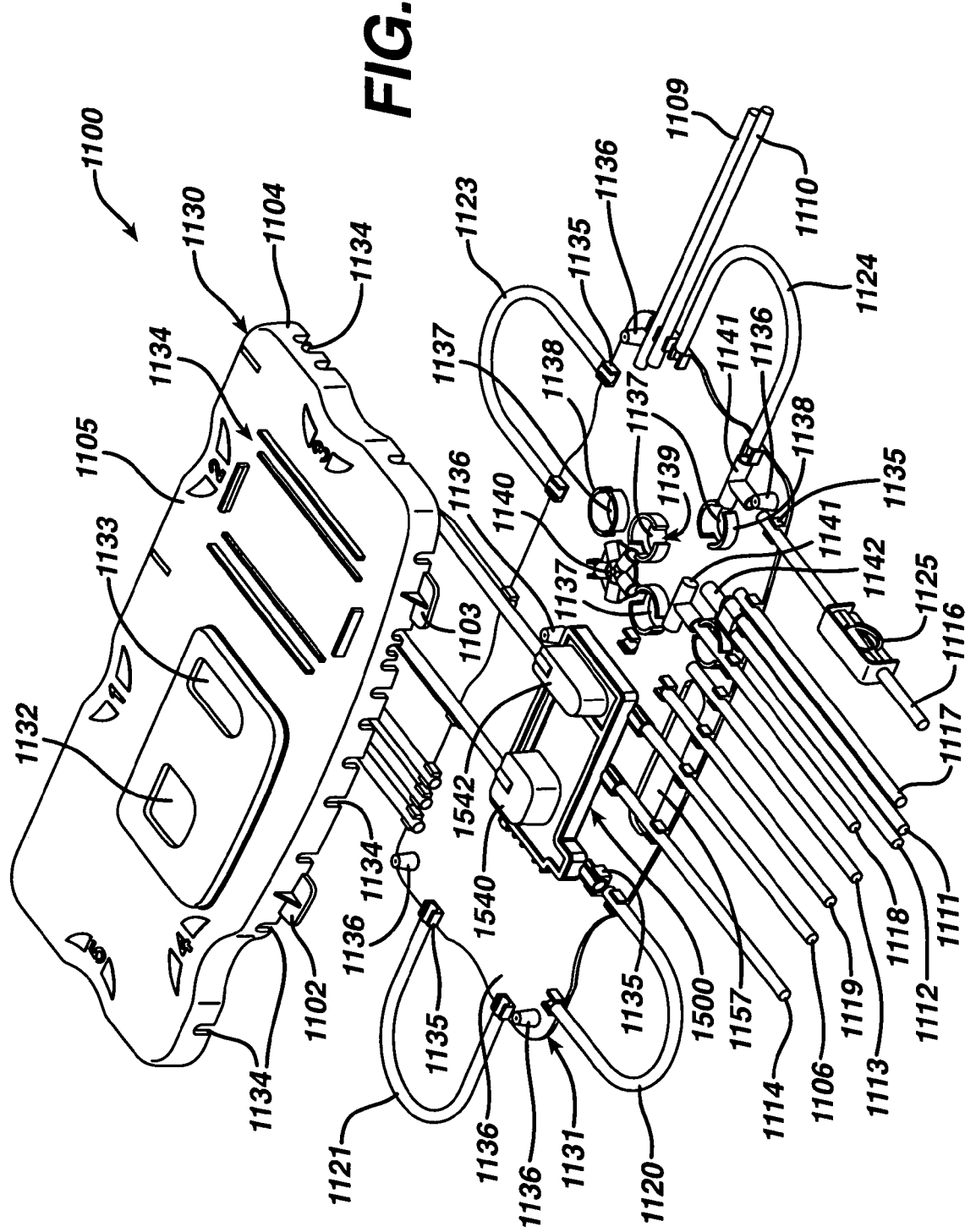
FIG. 3 is an exploded view of the cassette of FIG. 2.

Turning now to FIG. 3, cassette 1100 is shown with housing 1101 in an exploded state. For ease of illustration and description, the internal tubular circuitry within housing 1101 is not illustrated in FIG. 3. The internal tubular circuitry is illustrated in FIG. 4 and will be discussed in relation thereto. Cassette 1100 has filter assembly 1500 positioned therein and in fluid connection with inlet tube 1106, outlet tube 1114, and one end of each of pump tube loops 1120 and 1121. Filter assembly 1500 comprises vent chambers 1540 and 1542. Filter assembly 1500, and its functioning, is discussed in detail below with respect to FIGS. 6–10.

Figure 5:
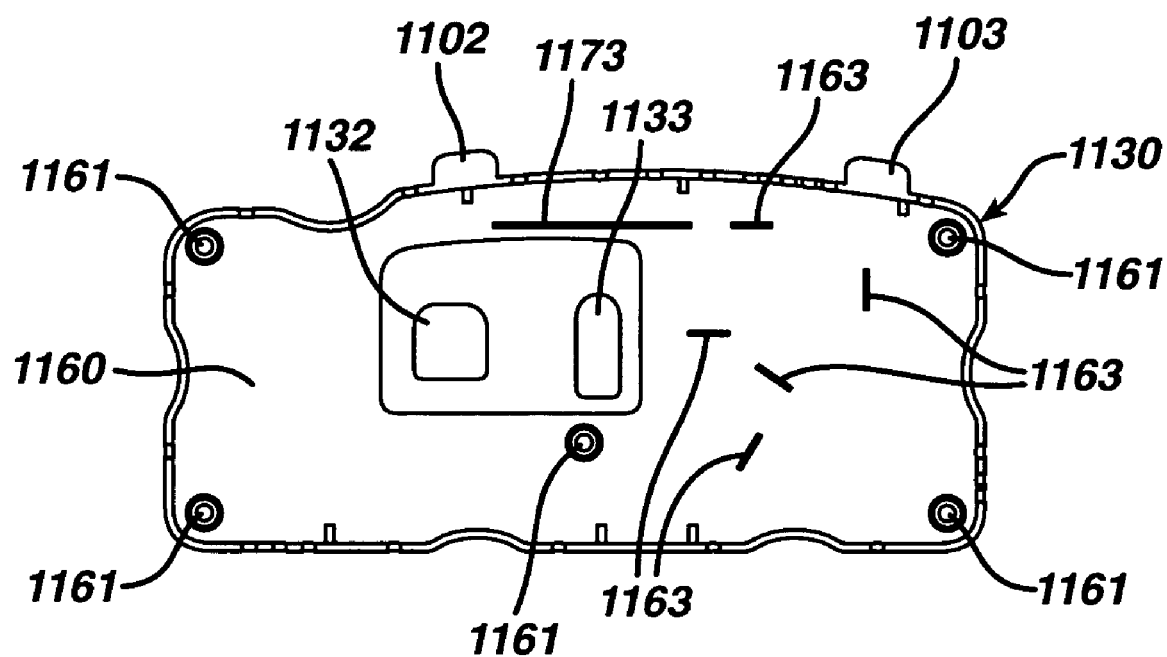
FIG. 5 is a bottom view of a cover of cassette of FIG. 2.

Housing 1101 comprises cover 1130 and base 1131. Cover 1130 has top surface 1105, a bottom surface 1160 (FIG. 5), and side wall 1104. Cover 1130 has openings 1132 and 1133 for allowing vent chambers 1540 and 1542 of filter assembly 1500 to extend therethrough. Side wall 1104 has a plurality of tube slots 1134 to allow the inlet tubes, outlet tubes, and pump loop tubes to pass into the internal space of housing 1101 for connection with the internal tubular circuitry located therein. Only a few tube slots 1134 are labeled in FIG. 3 to avoid numerical crowding. Tabs 1102 and 1103 are positioned on side wall 1104 so as not to interfere with tube slots 1134. Cover 1130 has occlusion bars 1162 and 1162A extending from bottom surface 1160 (FIG. 5). Occlusion bars 1162 and 1162A are preferably molded into bottom surface 1160 of cover 1130 during its formation.

Base 1131 has a plurality of U-shaped tube-holders 1135 extending upward from top surface 1136. U-shaped tube holders 1135 hold the inlet tubes, outlet tubes, pump loop tubes, filter assembly, and internal tubular circuitry in place. Only a few U-shaped holders 1135 are labeled in FIG. 3 to avoid numerical crowding. Preferably, a U-shaped holder 1135 is provided on base 1131 at each location where an inlet tube, an outlet tube, or a pump loop tube passes through a tube slot 1134 on side wall 1104. Male extrusions 1136 protrude from top surface 1136 of base 1131 for mating with corresponding female holes 1161 located on bottom surface 1160 of cover 1130 (FIG. 5). Preferably, a male protrusion 1136 is located at or near each of the four corners of base 1130 and near filter 1500. Male protrusions 1136 mate with the female holes 1161 to form a snap-fit and secure base 1131 to cover 1130.

Base 1131 further comprises a hub 1140. Hub 1140 is a five-way tube connector used to connect five tubes of the internal tubular circuitry. Preferably, three apertures 1137 are located near and surround three of the tubes leading into hub 1140. Hub 1140 acts as a centralized junction which can be used, in conjunction with compression actuators 1240–1247 (FIG. 22), to direct fluids through photopheresis kit 1000 and to and from the patient. In addition to hub 1140, appropriate tube connectors, such as T-connectors 1141 and Y-connector 1142, are used to obtain the desired flexible tubing pathways.

Figure 22:
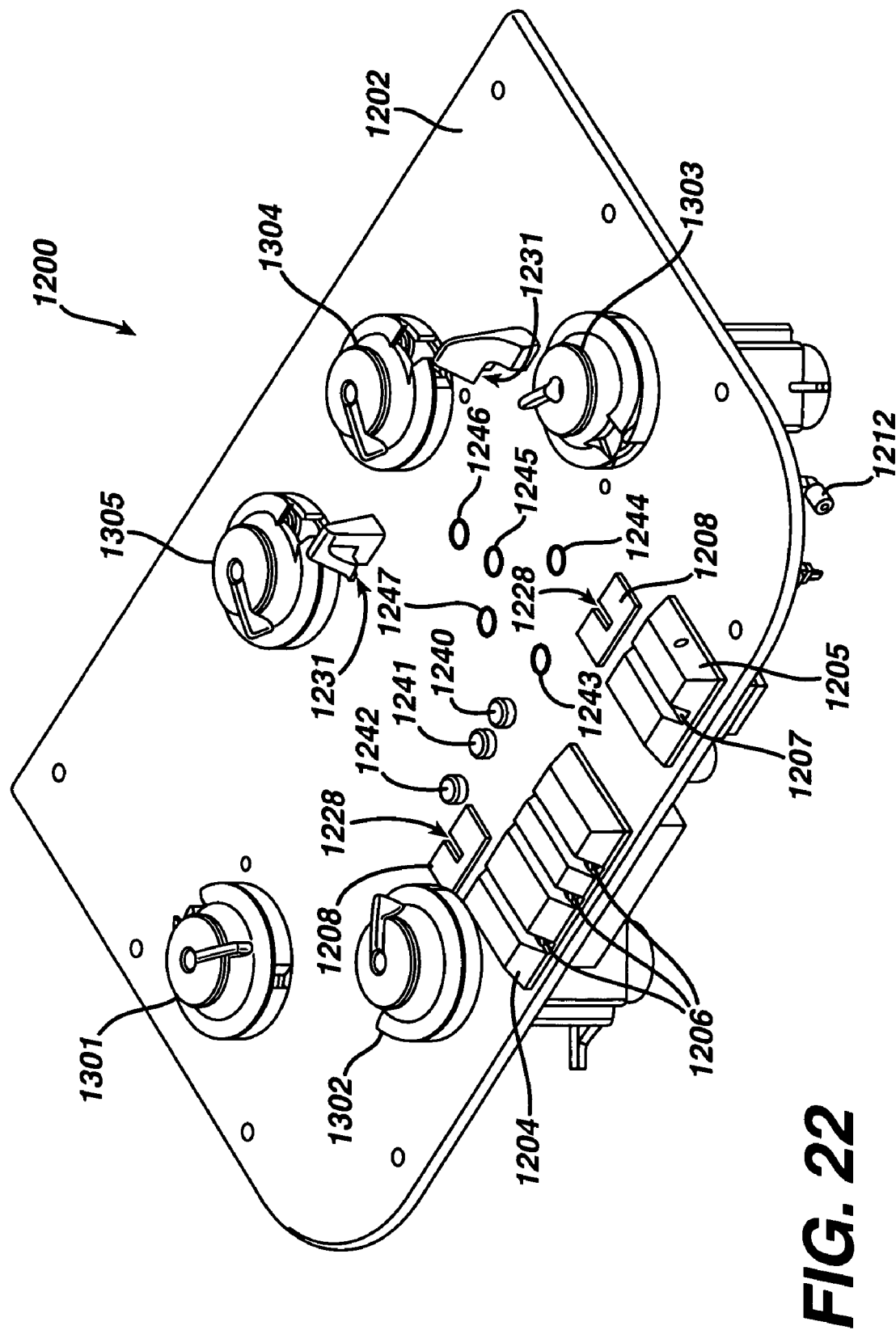
FIG. 22 is an elevated perspective view of an embodiment of the fluid flow control deck of the tower system of FIG. 17.

Five apertures 1137 are located on the floor of base 1130. Each aperture 1137 is surrounded by an aperture wall 1138 having slots 1139 for passing portions of the internal tubular circuitry therethrough. An elongated aperture 1157 is also provided on the floor of base 1131. Apertures 1137 are located on base 1131 to align with corresponding compression actuators 1243–1247 of deck 1200 (FIG. 22). Aperture 1157 is located on base 1131 to align with compression actuators 1240–1242 of deck 1200 (FIG. 22). Each aperture 1137 is sized so that a single compression actuator 1243–1247 can extend therethrough. Aperture 1157 is sized so that three compression actuators 1240–1242 can extend therethrough. Compression actuators 1240–1247 are used to close/occlude and open certain fluid passageways of the internal tubular circuitry in order to facilitate or prohibit fluid flow along a desired path. When it is desired to have a certain passageway open so that fluid can flow therethrough, the compression actuator 1240–1247 for that passageway is in a lowered position However, when it is desired to have a certain fluid passageway closed so that fluid can not flow therethrough, the appropriate compression actuator 1240–1247 is raised, extending the compression actuator 1240–1247 through aperture 1137 or 1157 and compressing a portion of the flexible tubular circuitry against bottom surface 1160 (FIG. 5) of cover 1130, thereby closing that passageway. Preferably, occlusion bars 1163 and 1173 (FIG. 5) are positioned on bottom surface 1160 to align with the compression actuators 1240–1247 so that the portion of flexible tubing being occluded is compressed against occlusion bar 1163 or 1173. Alternatively, the occlusion bar can be omitted or located on the compression actuators themselves.

It is preferable for cassette 1100 to have a unique identifier that can communicate with and relay information to permanent tower system 2000. The unique identifier is provided to ensure that the disposable photopheresis kit is compatible with the blood drive equipment into which it is being loaded, and that the photopheresis kit is capable of running the desired treatment process. The unique identifier can also be used as a means to ensure that the disposable photopheresis kit is of a certain brand name or make. In the illustrated example, the unique identifier is embodied as data card 1195 (FIG. 2) that is inserted into data card receiving port 2001 of permanent tower system 2000 (FIG. 17). Data card 1195 has both read and write capabilities and can store data relating to the treatment therapy performed for future analysis. The unique identifier can also take on a variety of forms, including, for example, a microchip that interacts with the blood drive equipment when the kit is loaded, a bar code, or a serial number.

Cover 1130 has data card holder 1134 for holding data card 1195 (FIG. 1). Data card holder 1134 comprises four elevated ridges in a segmented rectangular shape for receiving and holding data card 1195 to cassette 1100. Data card holder 1134 holds data card 1195 in place via a snap-fit (FIG. 2).

Referring now to FIGS. 1 and 4, the internal tubular circuitry of cassette 1100 will now be discussed. At least a portion of the internal tubular circuitry is preferably made of flexible plastic tubing that can be pinched shut by the exertion of pressure without compromising the hermetic integrity of the tube. Base 1131 of cassette 1100 is illustrated in FIG. 4 so that the internal tubular circuitry can be viewed. Inlet tubes 1107 and 1108 and outlet tube 1115 are provided for coupling cassette 1100 to centrifuge bowl 10 (FIG. 1). More specifically, outlet tube 1115 is provide for delivering whole blood from cassette 1100 to centrifuge bowl 10, and inlet tubes 1107 and 1108 are respectively provide for returning a lower density blood components and higher density blood components to cassette 1100 for further routing through photopheresis kit 1000. The lower density blood components can include, for example, plasma, leukocytes, platelets, buffy coat, or any combination thereof. The higher density components can include, for example, red blood cells. Outlet tube 1117 and inlet tube 1112 fluidly couple cassette 1100 to irradiation chamber 700. More specifically, outlet tube 1117 is provided for delivering an untreated lower density blood component, for example buffy coat, to irradiation chamber700 for exposure to photo energy, while inlet tube 1112 is provided for returning the treated lower density blood component to cassette 1100 for further routing.

Inlet tube 1111 and outlet tube 1116 couple treatment bag 50 to cassette 1100. Outlet tube 1116 is provided to deliver an untreated low density blood component, for example buffy coat, to treatment bag 50. Outlet tube 1116 has hematocrit ("HCT") sensor 1125 operably connected thereto to monitor for the introduction of a high density blood component, such as red blood cells. HCT sensor 1125 is a photo sensor assembly and is operably coupled to a controller. HCT sensor 1125 sends a detection signal to the controller when red blood cells are detected in outlet tube 1116 and the controller will take the appropriate action. Inlet tube 1111 is provided to return the untreated low density blood component from treatment bag 50 to cassette 1100 for further routing. Inlet tubes 1109 and 1110 are respectively connected to a saline and anticoagulant storage bags (not shown) via spikes 1190 and 1191 and are provided for delivering saline and an anticoagulant fluid to cassette 1100 for further routing to the patient.

Inlet/Outlet tube 1113 and outlet tube 1118 couple plasma collection bag 50 to cassette 1100. More specifically, outlet tube 1118 delivers a blood component, such as plasma, to plasma collection bag 51. Inlet/Outlet tube 1113 can be used to either deliver red blood cells to plasma collection bag 51 from cassette 1100 or return the blood component(s) that build up in plasma collection bag 51 to cassette 1100 for further routing. Inlet tube 1106 and outlet tubes 1119 and 1114 are coupled to a patient. Specifically, outlet tube 1114 is provided to return treated blood, saline, untreated blood components, treated blood components, and other fluids back to the patient. Inlet tube 1106 is provided for delivering untreated whole blood (and a predetermined amount of an anticoagulant fluid) from the patient to cassette 1100 for routing and treatment within photopheresis kit 1000. Outlet tube 1119 is specifically provided for delivering an anticoagulant fluid to inlet tube 1106. It is preferable that all tubing is disposable medical grade sterile tubing. Flexible plastic tubing is the most preferred.

Cassette 1100 has five pump tube loops 1120, 1121, 1122, 1123, and 1124 for driving blood fluids throughout cassette 1100 and photopheresis kit 1000. More specifically, pump tube loop 1121 loads into whole blood pump 1301 and respectively drives whole blood in and out of cassette 1100 via inlet tube 1106 and outlet tube 1115, passing through filter 1500 along the way. Pump loop tube 1120 loads into return pump 1302 and drives blood fluids through filter 1500 and back to the patient via outlet tube 1114. Pump loop tube 1122 loads into red blood cell pump 1305 and draws red blood cells from centrifuge bowl 10 and drives them into cassette 1100 via inlet line 1108. Pump loop tube 1123 loads into anticoagulant pump 1304 and drives an anticoagulant fluid into cassette 1100 via inlet tube 1124 and out of cassette 1100 to via outlet tube 1119, which connects with inlet tube 1106. Pump loop tube 1124 loads into recirculation pump 1303 and drives blood fluids, such as plasma, through treatment bag 50 and irradiation chamber 700 from cassette 1100.

Each of peristaltic pumps 1301–1305 are activated when necessary to perform the photopheresis treatment therapy according to an embodiment of the method of the present invention which is described below in relation to FIGS. 26–27. Peristaltic pumps 1301–1305 can be operated one at a time or in any combination. The pumps 1301–1305 work in conjunction with compression actuators 1240–1247 to direct fluids through desired pathways of photopheresis kit 1000. Apertures 1137 and 1157 are strategically located on base 1131 along the internal tubular circuitry to facilitate proper routing. Through the use of compression actuators 1240–1247, the fluids can be directed along any pathway or combination thereof.

1. The Filter Assembly

Figure 6:
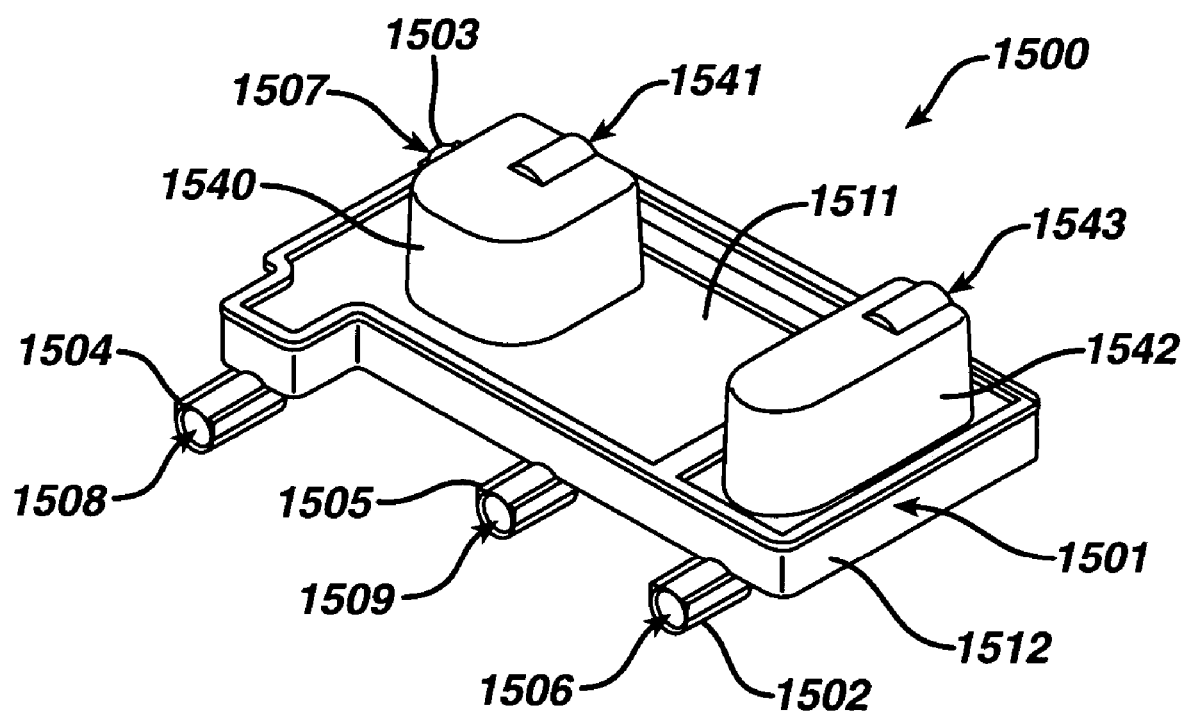
FIG. 6 is an elevated perspective view of an embodiment of a filter assembly.
Figure 7:
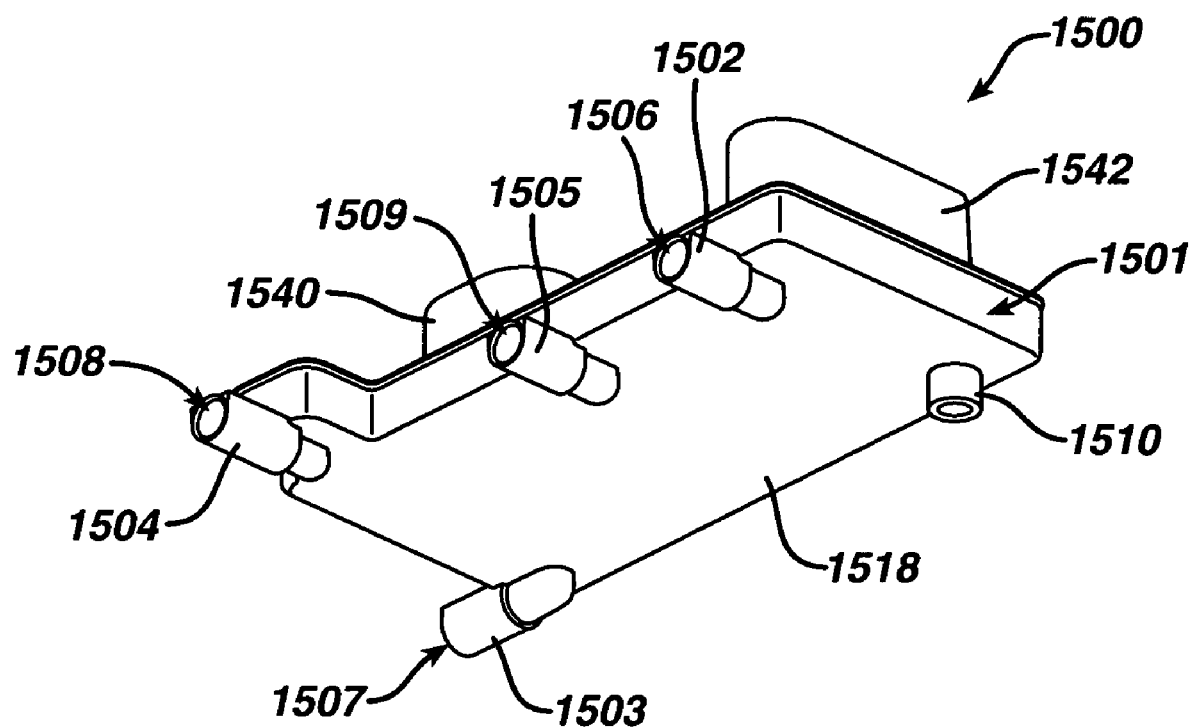
FIG. 7 is bottom perspective view of the filter assembly of FIG. 6.

Filter 1500, which is located within cassette 1100 as described above, is illustrated in detail in FIGS. 6–10. Referring first to FIGS. 6 and 7, filter 1500 is illustrated fully assembled. Filter 1500 comprises a filter housing 1501. Filter housing 1501 is preferably constructed of a transparent or translucent medical grade plastic. However, the invention is not so limited and filter housing 1501 can be constructed of any material that will not contaminate blood or other fluids that are flowing therethrough.

Filter housing 1501 has four fluid connection ports extruding therefrom, namely whole blood inlet port 1502, whole blood outlet port 1503, treated fluid inlet port 1504, and treated fluid outlet port 1505. Ports 1502–1505 are standard medical tubing connection ports that allow medical tubing to be fluidly connected thereto. Ports 1502–1505 respectively contain openings 1506, 1507, 1508 and 1509. Openings 1506, 1507, 1508 and 1509 extend through ports 1502, 1503, 1504 and 1505, forming fluid passageways into filter housing 1501 at the desired locations.

Ports 1502, 1503, 1504 and 1505 are also used to secure filter 1500 within cassette 1100. In doing so, ports 1502, 1503, 1504 and 1505 can engage U-shaped fasteners 1135 of cassette 1100 (FIG. 3). Filter housing 1501 also has a protrusion 1510 extending the bottom surface of housing floor 1518. Protrusion 1510 fits into a guide hole of base 1131 of cassette 1100 (FIG. 3).

Figure 8:
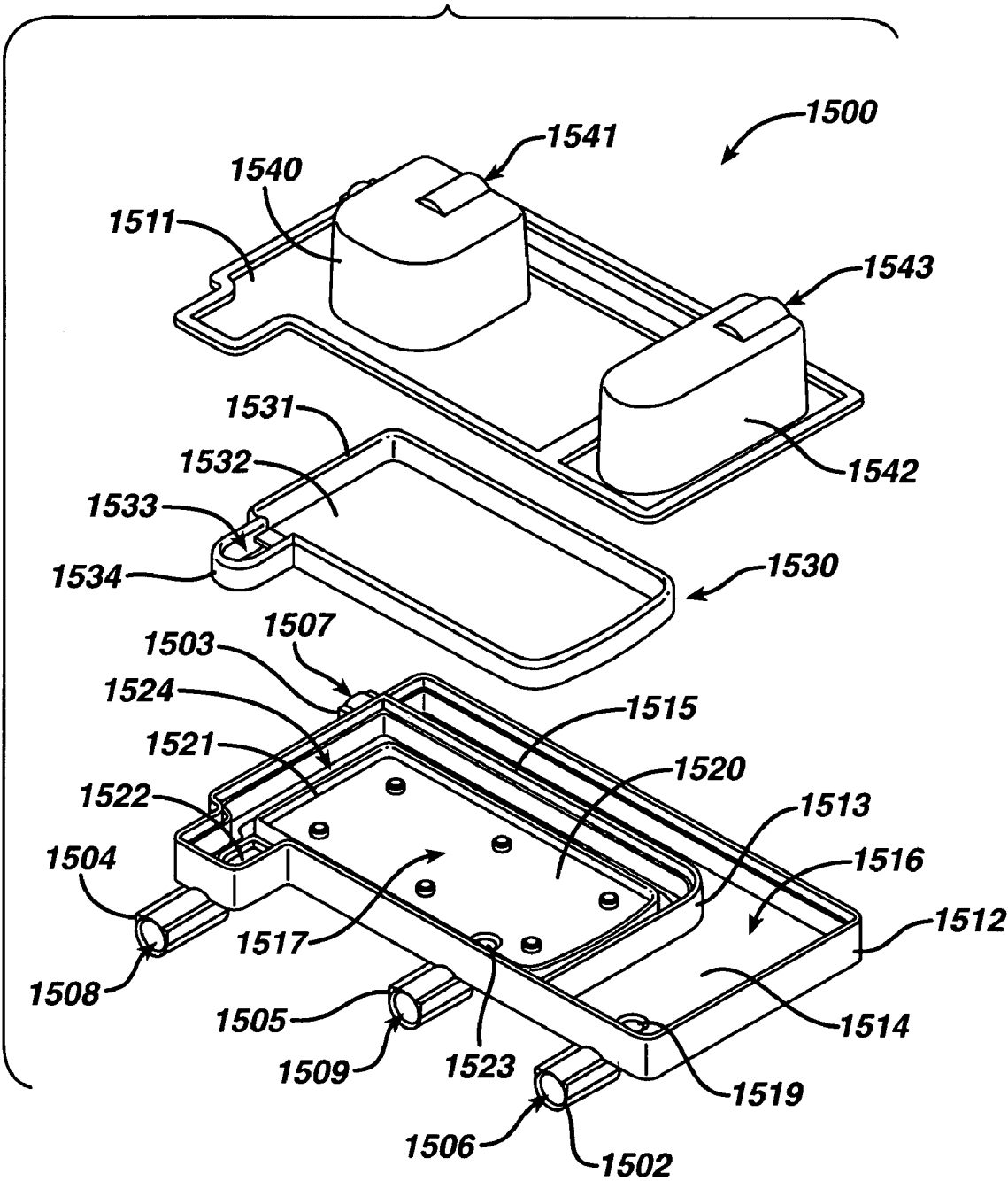
FIG. 8 is an exploded view of the filter assembly of FIG. 6.

Referring now to FIG. 8, filter 1500 is illustrated in an exploded state. Filter housing 1501 is a two-piece assembly comprising roof 1511 and base 1512. Roof 1511 is connected to base 1512 by any means known in the art, such as ultrasonic welding, heat welding, applying an adhesive, or by designing roof 1511 and base 1512 so that a tight fit results between the two. While filter housing 1501 is illustrated as a two-piece assembly, filter housing 1501 can be either a single piece structure or a multi-piece assembly.

Base 1512 has chamber separation wall 1513 extending upward from a top surface of housing floor 1518 (FIG. 7). When base 1512 and roof 1511 are assembled, top surface 1515 of chamber separation wall 1513 contacts the bottom surface of roof 1511, forming two chambers within the filter housing, whole blood chamber 1516 and filter chamber 1517. Fluid can not directly pass between whole blood chamber 1516 and filter chamber 1517.

Whole blood chamber 1516 is a substantially L-shaped chamber having floor 1514. Whole blood chamber 1516 has a whole blood inlet hole 1519 and a whole blood outlet hole (not illustrated) in floor 1514. Whole blood inlet hole 1519 and the whole blood outlet hole are located at or near the ends of the substantially L-shaped whole blood chamber 1516. Whole blood inlet hole 1519 forms a passageway with opening 1506 of inlet port 1502 so that a fluid can flow into whole blood chamber 1516. Similarly, the whole blood outlet hole (not illustrated) forms a passageway with opening 1507 of outlet port 1503 so that fluid can flow out of whole blood chamber 1516.

Filter chamber 1517 has floor 1520. Floor 1520 has elevated ridge 1521 extending upward therefrom. Elevated ridge 1521 is rectangular and forms a perimeter. While elevated ridge 1521 is rectangular in the illustrated embodiment, elevated ridge 1521 can be any shape so long as it forms an enclosed perimeter. The height of elevated ridge 1521 is less than the height of chamber separation wall 1513. As such, when roof 1511 and base 1512 are assembled, space exists between the top of elevated ridge 1521 and the bottom surface of roof 1511. Elevated ridge 1521 and chamber separation wall 1513 form a trench 1524 there between.

In order to facilitate fluid flow through filter chamber 1517, floor 1520 of filter chamber 1517 has treated fluid inlet hole 1522 and treated fluid outlet hole 1523. Treated fluid inlet hole 1522 is located exterior of the perimeter formed by elevated ridge 1521 and forms a passageway with opening 1508 of inlet port 1504 so that a fluid can flow into filter chamber 1517 from outside filter housing 1501. Treated fluid outlet hole 1523 is located interior of the perimeter formed by elevated ridge 1521 and forms a passageway with opening 1509 of outlet port 1505 so that a fluid can flow out of filter chamber 1517.

Filter 1500 further comprises filter element 1530. Filter element 1530 comprises frame 1531 having filter media 1532 positioned therein. Frame 1531 has a neck 1534 that forms a filter inlet hole 1533. Filter element 1530 is positioned in filter chamber 1517 so that frame 1531 fits into trench 1524 and neck 1534 surrounds treated blood inlet hole 1522. Filter inlet hole 1533 is aligned with treated fluid inlet hole 1522 so that incoming fluid can freely flow through holes 1522 and 1533 into filter chamber 1517. Frame 1531 of filter element 1530 forms a hermetic fit with elevated ridge 1521. All fluid that enters filter chamber 1517 through holes 1522 and 1533 must pass through filter media 1532 in order to exit filter chamber 1517 via treated fluid outlet hole 1523. Filter media 1532 preferably has a pore size of approximately 200 microns. Filter media 1532 can be formed of woven mesh, such as woven polyester.

Figure 9:
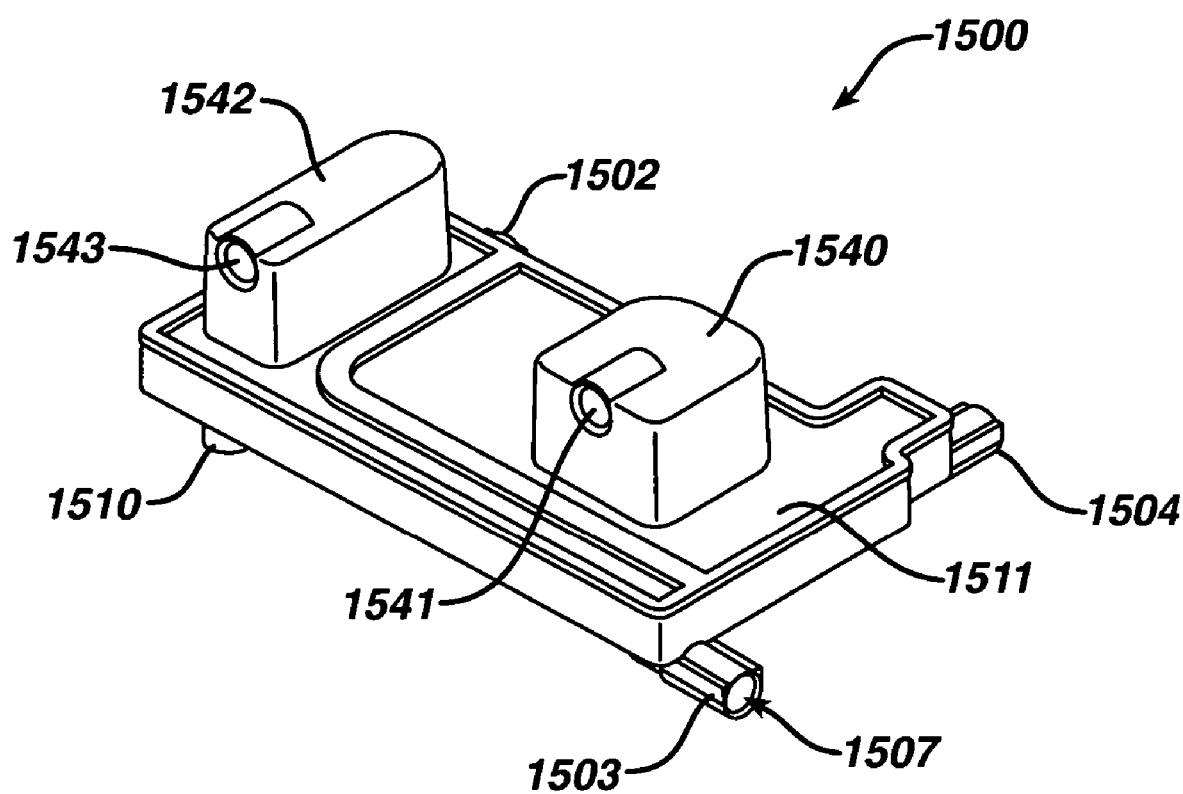
FIG. 9 is a rear perspective view of the filter assembly of FIG. 6.

Filter chamber 1517 further comprises filter vent chamber 1540 within roof 1511. Filter vent chamber 1540 has gas vent 1541 in the form of a hole (FIG. 9). Because gas vent 1541 opens into filter vent chamber 1540 which in turn opens into filter chamber 1517, gases that build-up within filter chamber 1517 can escape through gas vent 1541.

Similarly, whole blood chamber 1516 comprises blood vent chamber 1542 within roof 1511. Blood vent chamber 1541 has gas vent 1543 in the form of a hole. Because gas vent 1543 opens into blood vent chamber 1542 which in turn opens into whole blood chamber 1517, gases that build-up in whole blood chamber 1516 can escape via gas vent 1543.

FIG. 10 is a top view of filter 1500 having pressure sensors 1550 and 1551 connected to gas vents 1541 and 1543. Pressure sensors 1550 and 1551 are preferably pressure transducers. Pressure sensor 1550 is connected to gas vent 1541 via vent tubing 1552. Vent tubing 1552 fits into gas vent 1541 so as to form a tight fit and seal. Because gas vent 1541 opens into filter vent chamber 1540 which in turn opens into filter chamber 1517, the pressure in vent tubing 1552 is the same as in filter chamber 1517. By measuring the pressure in vent tubing 1552, pressure sensor 1550 also measures the pressure within filter chamber 1517. Similarly, pressure sensor 1551 is connected to gas vent 1543 via vent tubing 1553. Vent tubing 1553 fits into gas vent 1543 so as to form a tight fit and seal and pressure sensor 1551 measures the pressure within whole blood chamber 1516. Filter vent chamber 1540 and blood vent chamber 1542 extend through openings 1132 and 1133 of cassette 1100 when filter 1500 is positioned therein (FIG. 2). This allows the pressure within chambers 1516 and 1517 to be monitored while still protecting filter chamber 1500 and the fluid connections thereto.

Pressure sensors 1550 and 1551 are coupled to controller 1554, which is a properly programmed processor. Controller 1554 can be a main processor used to drive the entire system or can be a separate processor coupled to a main processor. Pressure sensors 1550 and 1551 produce electrical output signals representative of the pressure readings within chambers 1517 and 1516 respectively. Controller 1554 receives on a frequent or continuous basis data representing the pressure within chambers 1516 and 1517. Controller 1554 is programmed with values representing desired pressures within chambers 1516 and 1517. Controller 1554 continuously analyzes the pressure data it receives from pressure sensors 1550 and 1551 to determine whether the pressure readings are within a predetermined range from the desired pressure for chambers 1517 and 1516. Controller 1554 is also coupled to whole blood pump 1301 and return pump 1302. In response to the pressure data received from pressure sensors 1551 and 1550, controller 1554 is programmed to control the speed of whole blood pump 1301 and return pump 1302, thereby adjusting the flow rates through the pumps 1301 and 1301. Adjusting these flow rates in turn adjust the pressure within whole blood chambers 1516 and filter chamber 1517 respectively. It is in this way that the pressure within the lines drawing and returning blood to and from the patient is maintained at acceptable levels.

The functioning of filter 1500 during a photopheresis therapy session will now be discussed in relation to FIGS. 1, 6, and 10. While the functioning of filter 1500 will be described in detail with respect to drawing whole blood from a patient and returning a component of said whole blood back into the patient after it is treated, the invention is not so limited. Filter 1500 can be used in connection with almost any fluid, including red blood cells, white blood cells, buffy coat, plasma, or a combination thereof.

Whole blood pump 1601 draws whole blood from a patient who is connected to photopheresis kit 1000 via a needle connected to port 1193. The rotational speed of whole blood pump is set so that the pressure of the line drawing the whole blood from the patient is at an acceptable level. Upon being drawn from the patient, the whole blood passes into cassette 1100 via inlet tube 1106. Inlet tube 1106 is fluidly connected to inlet port 1502 of filter 1500. The whole blood passes through opening 1506 of inlet port 1502 and into L-shaped whole blood chamber 1516. The whole blood enters chamber 1516 through inlet hole 1519 which is located on floor 1514. As more whole blood enters chamber 1516, the whole blood spills along floor 1514 until it reaches the whole blood outlet hole (not illustrated) at the other end of L-shaped whole blood chamber 1516. As discussed above, the whole blood outlet whole forms a passageway with opening 1507 of outlet port 1503. The whole blood that is within chamber 1516 flows across floor 1514, through the whole blood outlet hole, into outlet port 1503, and out of filter 1500 through opening 1507.

As the whole blood passes through whole blood chamber 1516, gases that are trapped in the whole blood escape. These gases collect in blood vent chamber 1542 and then escape via gas vent 1543. Pressure sensor 1551 continuously monitors the pressure within blood chamber 1516 through vent tube 1553 and transmits corresponding pressure data to controller 1554. Controller 1554 analyzes the received pressure data and if necessary adjusts the speed of whole blood pump 1301, thereby adjusting the flow rate and pressure within chamber 1516 and inlet tube 1106. Controller 1554 adjust the pump speed to ensure that the pressure is within the desired pressure range.

The whole blood then exits filter 1500 through outlet port 1503 and passes out of cassette 1100 via outlet tube 1115. The whole blood is then separated into components and/or treated as described in detail below. Before being returned to the patient, this treated fluid (i.e. treated blood or blood components) must be filtered. Untreated fluids such as red blood cells also must be filtered and will subjected to the below filtering process. The treated fluid is fed into filter chamber 1517 through opening 1508 of inlet port 1504. Inlet port 1504 is fluidly connected to pump loop tube 1120. The treated fluid enters filter chamber 1517 through inlet hole 1522 and passes through filter inlet hole 1533 of filter element 1530. The treated fluid fills filter chamber 1517 until it spills over frame 1531 of filter element 1530, which is secured to elevated ridge 1521. The treated fluid passes through filter media 1532. Filter media 1532 removes contaminants and other undesired materials from the treated fluid while at the same facilitating the release of trapped gases from the treated fluid. The treated fluid that passes through filter media 1532 gathers on floor 1520 of filter chamber 1517 within the perimeter formed by elevated ridge 1521. This treated fluid then passes into treated fluid outlet hole 1523 and out of filter 1500 through opening 1506 of outlet port 1502. The treated fluid is then returned to the patient via outlet tube 1114, which is fluidly connected to outlet port 1502. The treated fluid is driven through filter chamber 1517 and outlet tube 1114 by return pump 1302.

Gases that are trapped in the treated fluid escape and collect in filter vent chamber 1540 as the treated fluid flows through filter chamber 1517. These gases then escape filter 1500 via gas vent 1541. Pressure sensor 1550 continuously monitors the pressure within filter chamber 1517 through vent tube 1552 and transmits corresponding pressure data to controller 1554. Controller 1554 analyzes the received pressure data and compares it to the desired pressure value and range. If necessary, controller 1554 adjusts the speed of return pump 1302, thereby adjusting the flow rate and pressure within chamber 1517 and outlet tube 1114.

B. Irradiation Chamber

Figure 11:
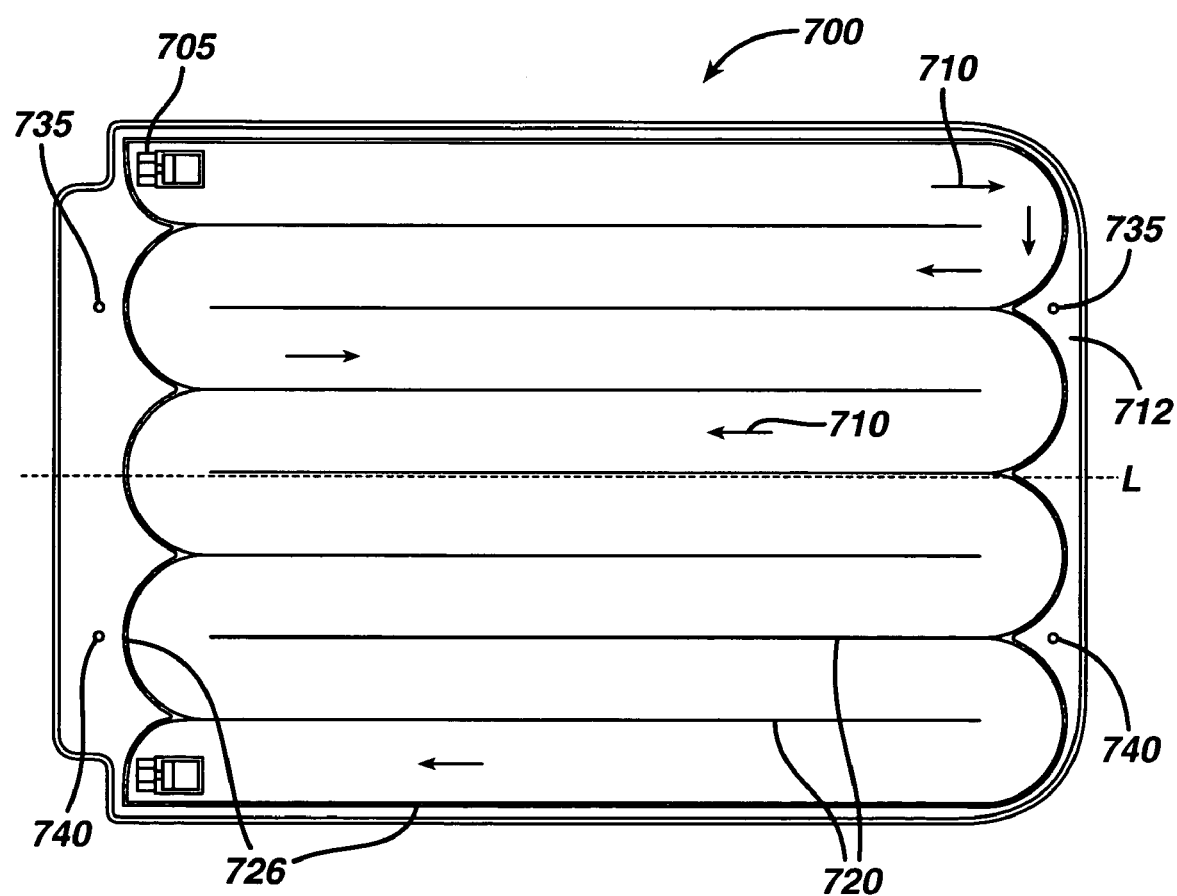
FIG. 11 is a front view of an irradiation chamber.

FIGS. 11–16 illustrate irradiation chamber700 of photopheresis kit 1000 in detail. Referring first to FIG. 11, irradiation chamber 700 is formed by joining two plates, a front and a back plate having a thickness of preferably about 0.06 in. to about 0.2 in., which are preferably comprised of a material ideally transparent to the wavelength of electromagnetic radiation. In the case of ultraviolet A radiation, polycarbonate has been found most preferred although other materials such as acrylic may be employed. Similarly, many known methods of bonding may be employed and need not be expanded on here.

The first plate 702 has a first surface 712 and a second surface 714. In a preferred embodiment the first plate 702 has a first port 705 on a first surface 712, in fluid communications with the second surface 714. The second surface 714 of the first plate 702 has a raised boundary 726A defining an enclosure. The boundary 726A preferably extends substantially perpendicular from the second surface 714 (i.e. about 80–100 degrees). Extending from the second surface 714 (preferably substantially perpendicularly) are raised partitions 720A. The boundary 726A surrounds the partitions 720A. One end of each partition 720A extends and contacts the boundary 726A.

The second plate 701 has a first surface 711 and a second surface 713. In a preferred embodiment the second plate 701 preferably has a second port 730 on a first surface 711, in fluid communications with the second surface 713. The second surface 713 of the back plate 701 has a raised boundary 726B defining an enclosure. The boundary 726B preferably extends substantially perpendicular from the second surface 713 (i.e. about 80–100 degrees). Extending from the second surface 713 (preferably substantially perpendicular) are raised partitions (720B). The boundary 726B surrounds the partitions 720B. One end of each partition 720A extends and contacts one side of boundary (726B).

The joining of the second surfaces of the first and second plates results in a fluid tight junction between boundaries 726A and 726B thereby forming boundary 726. Partitions 720A and 720B are also joined forming a fluid tight junction thereby forming partition 720. The boundary 726 forms an irradiation chamber 700 and together with the partitions 720 provides a pathway 710 having channels 715 for conducting fluid. The pathway maybe serpentine, zig-zag, or dovetailed. Currently preferred is a serpentine pathway.

Figure 12:
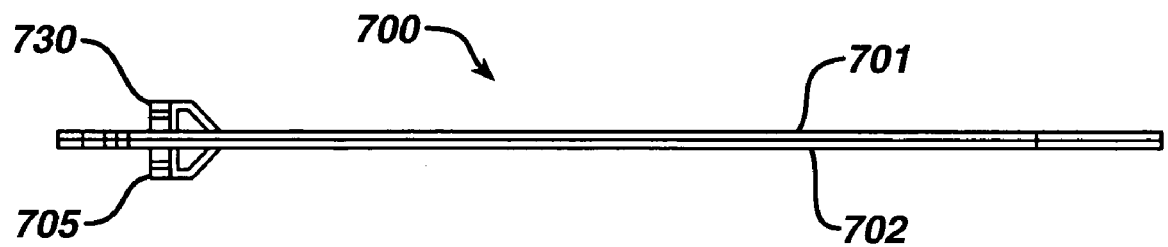
FIG. 12 is a side longitudinal view of the irradiation chamber of FIG. 11.

With reference to FIGS. 11 and 12, irradiation chamber 700 comprises a serpentine pathway 710 for conducting patient fluid, such as buffy coat or white blood cells, from inlet port 705 to outlet port 730, i.e., the serpentine pathway 710 is in fluid communication with inlet port 705 of front plate 702 and outlet port 730 of back plate 701. Patient fluid is supplied from cassette 1100 to inlet port 705 via outlet tube 1117. After photoactivation and passing through serpentine pathway 710, the treated patient fluid is returned to cassette 1100 via inlet tube 1112 (FIGS. 1 and 4). The patient fluid is driven by recirculation pump 1303. Self-shielding effects of the cells is reduced while the cells are photoactivated by irradiation impinging upon both sides of irradiation chamber 700.

FIG. 11 shows pin 740 and recess 735 which align the two plates of irradiation chamber prior to being joined together in a sealing arrangement by RF welding, heat impulse welding, solvent welding or adhesive bonding. Joining of the plates by adhesive bonding and RF welding is more preferred. Joining of the front and back plates by RF welding is most preferred as the design of the raised partitions 720 and perimeter 725 minimizes flashing and allows for even application of RF energy. Locations of pin 740 and recess 735 may be inside serpentine pathway 710 or outside of serpentine pathway 710. FIG. 2 also shows a view of an irradiation chamber with axis L. Rotation of chamber 700 180 degree about axis L gives the original configuration of the irradiation chamber. The irradiation chamber of the present invention has $C_2$ symmetry about axis L.

Figure 13:
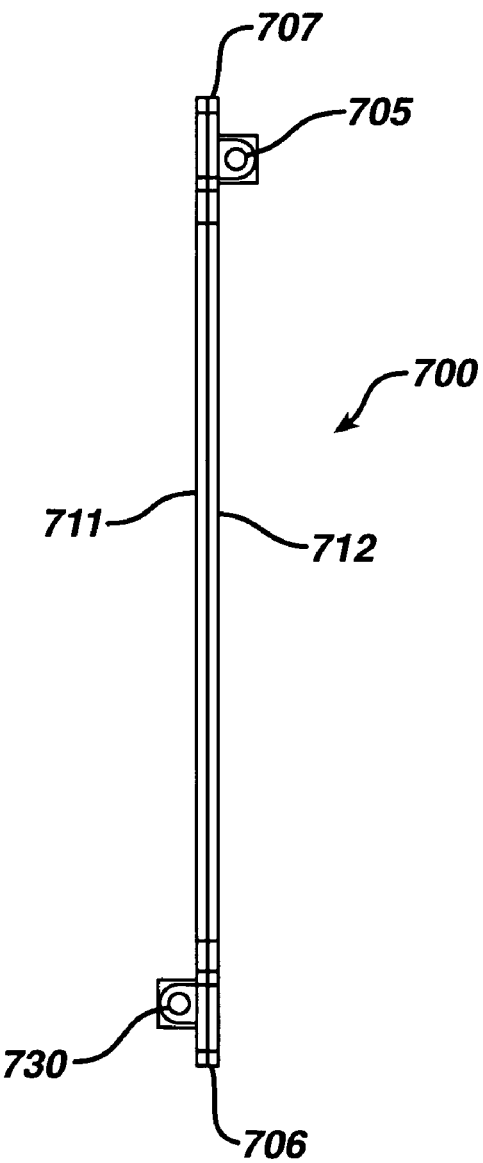
FIG. 13 is a side transverse view of the irradiation chamber of FIG. 11
Figure 16:
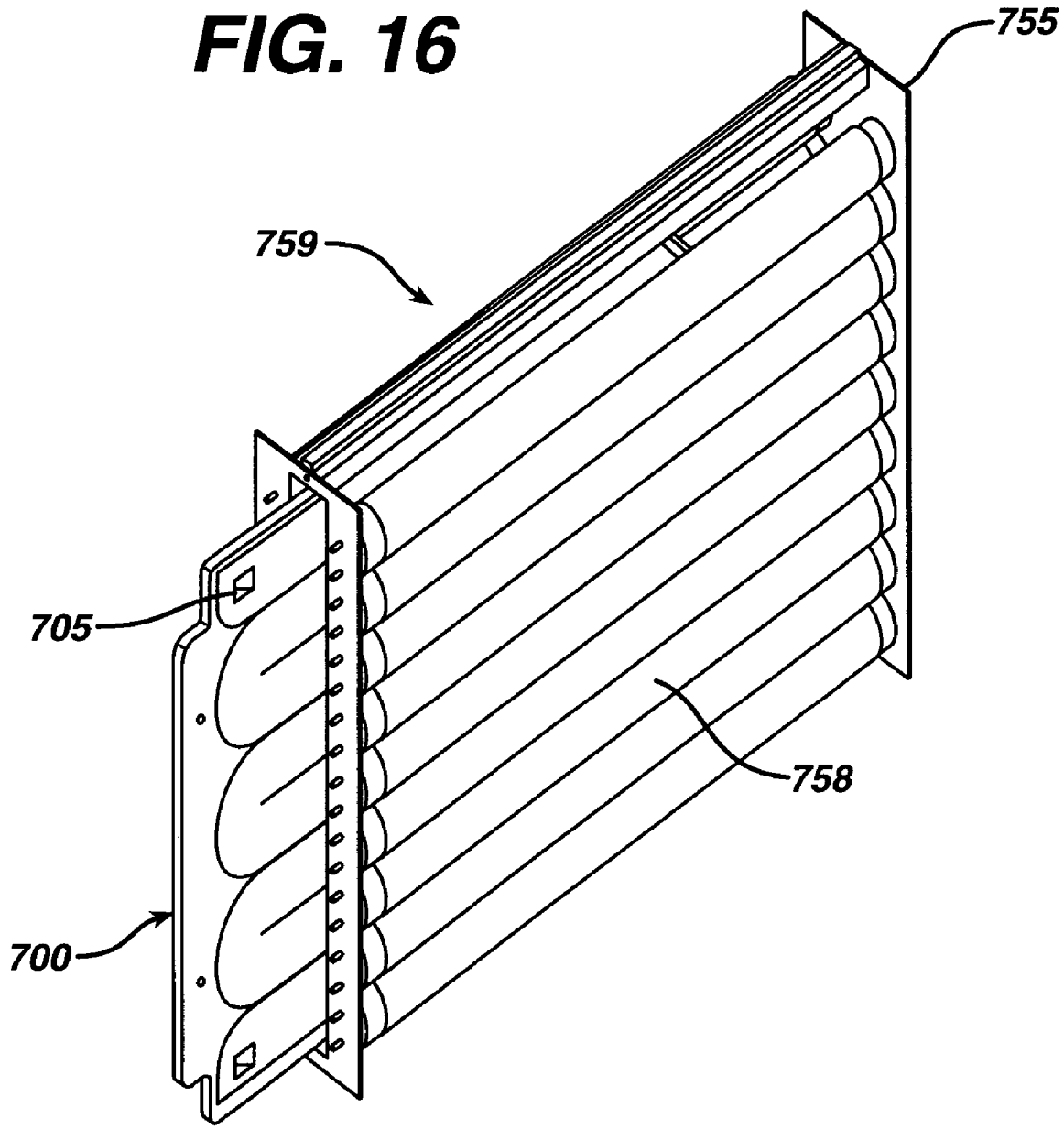
FIG. 16 is a perspective view of the irradiation chamber of FIG. 11 positioned within a UVA light assembly.

Referring to FIGS. 11, 13, and 16, the leukocyte enriched blood, plasma, and priming solution are delivered through inlet port 705 of front plate 702 of irradiation chamber 700 into channel 715. The channel 715 in the irradiation chamber 700 is relatively "thin" (e.g. on the order of approximately 0.04" as distance between two plates) in order to present large surface area of leukocyte rich blood to irradiation and reduce the self-shielding effects encountered with lower surface area/volume ratios. The cross section shape of channel 715 is substantially rectangular (e.g. rectangular, rhomboidal or trapezoidal) which has as its long side the distance between partition 720 and the distance between the plates as its short side. The shape of the cross section is designed for optimal irradiation of cells passing through channel 715. While a serpentine pathway 710 is preferred in order to avoid or minimize stagnant areas of flow, other arrangements are contemplated.

Figure 18:
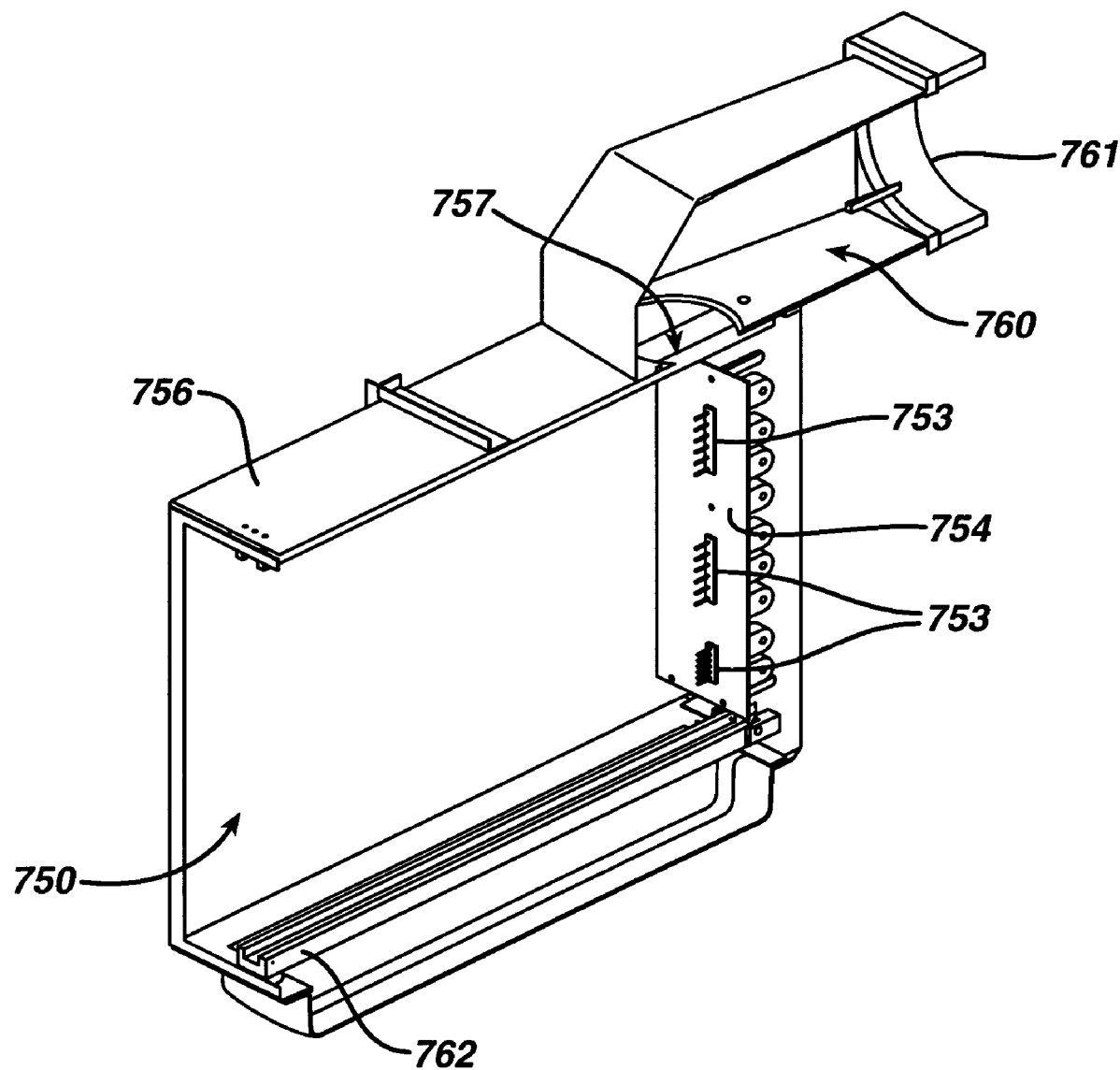
FIG. 18 is a cross-sectional view of an embodiment of the photoactivation chamber, without a UVA light assembly, used in the tower system of FIG. 17.

The irradiation chamber 700 allows efficient activation of photoactivatable agents by irradiation from a light array assembly, such as the PHOTOSETTE®'s two banks of UVA lamps (758) for activation (FIG. 16). The irradiation plate and UVA light assembly (759) are designed to be used in a setting where edge 706 is oriented downward and edge 707 points upward. In this orientation, fluids entering input port 705 can exit from outlet port 730 with the aid of gravity. In the most preferred embodiment, irradiation of both sides of the irradiation chamber takes place concurrently while still permitting facile removal of the chamber. UVA light assembly 759 is located within UV chamber 750 of permanent tower system 2000 (FIGS. 17 and 18).

The irradiation chamber's fluid pathway loops to form two or more channels in which the leukocyte-enriched blood is circulated during photoactivation by UVA light. Preferably, irradiation chamber 700 has between 4 to 12 channels. More preferably, the irradiation chamber has 6 to 8 channels. Most preferably, the irradiation chamber has 8 channels.

Figure 14:
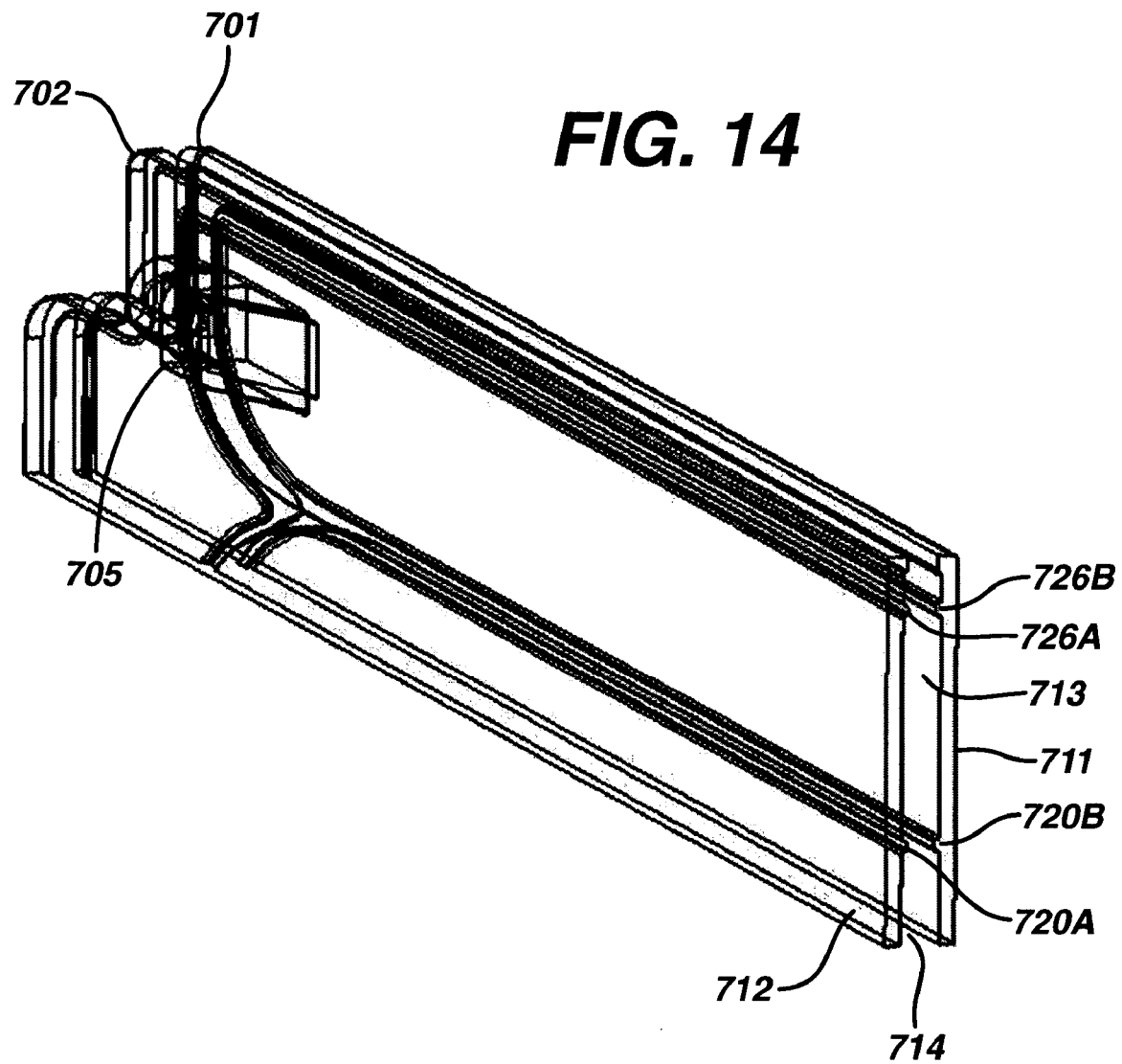
FIG. 14 is a cut-away view of a section of the first plate and the second plate prior to being joined together to form the irradiation chamber of FIG. 11.

FIG. 14 shows cut-away views of the irradiation chamber. The channels 715 of serpentine pathway 710 are formed by the joining of raised partition 720 and perimeter 726 of the plates.

The irradiation chamber of the present invention can be made from a biocompatible material and can be sterilized by known methods such as heating, radiation exposure or treatment with ethylene oxide (ETO).

The method of irradiating cells using irradiation chamber 700 during extracorporeal treatment of cells with electromagnetic radiation (UVA) to be used in the treatment of a patient (such as to induce apoptosis in the cells and administer the cells into the patient) will now be discussed. Preferably the cells treated will be white cells.

In one embodiment of this method, a photoactivatable or photosensitive compound is first administered to at least a portion of the blood of a recipient prior to the extracorporeal treatment of the cells. The photoactivatable or photosensitive compound may be administered in vivo (e.g., orally or intravenously). The photosensitive compound, when administered in vivo may be administered orally, but also may be administered intravenously and/or by other conventional administration routes. The oral dosage of the photosensitive compound may be in the range of about 0.3 to about 0.7 mg/kg., more specifically, about 0.6 mg/kg.

When administered orally, the photosensitive compound may be administered at least about one hour prior to the photopheresis treatment and no more than about three hours prior to the photopheresis treatment. If administered intravenously, the times would be shorter. Alternatively, the photosensitive compound may be administered prior to or contemporaneously with exposure to ultraviolet light. The photosensitive compound may be administered to whole blood or a fraction thereof provided that the target blood cells or blood components receive the photosensitive compound. A portion of the blood could first be processed using known methods to substantially remove the erythrocytes and the photoactive compound may then be administered to the resulting enriched leukocyte fraction. In one embodiment, the blood cells comprise white blood cells, specifically, T-cells.

The photoactivatable or photosensitive compound may, in the case of some psoralens, be capable of binding to nucleic acids upon activation by exposure to electromagnetic radiation of a prescribed spectrum, e.g., ultraviolet light.

Photoactive compounds may include, but are not limited to, compounds known as psoralens (or furocoumarins) as well as psoralen derivatives such as those described in, for example, U.S. Pat. No. 4,321,919 and U.S. Pat. No. 5,399,719. The photoactivatable or photosensitive compounds that may be used in accordance with the present invention include, but are not limited to, psoralen and psoralen derivatives; 8-methoxypsoralen; 4,5'8-trimethylpsoralen; 5-methoxypsoralen; 4-methylpsoralen; 4,4-dimethylpsoralen; 4–5'-dimethylpsoralen; 4'-aminomethyl-4,5',8-trimethylpsoralen; 4'-hydroxymethyl-4,5',8-trimethylpsoralen; 4',8-methoxypsoralen; and a 4'-(omega-amino-2-oxa) alkyl-4,5',8-trimethylpsoralen, including but not limited to 4'-(4-amino-2-oxa) butyl-4,5',8-trimethylpsoralen. In one embodiment, the photosensitive compound that may be used comprises the psoralen derivative, amotosalen (S-59) (Cerus, Corp., Concord, Calif.). See, e.g., U.S. Pat. Nos. 6,552,286; 6,469,052; and 6,420,570. In another embodiment, the photosensitive compound that may be used in accordance with the invention comprises 8-methoxypsoralen.

Methoxsalen is a naturally occurring photoactive substance found in the seed of the Ammi majus (umbelliferae plant). It belongs to a class of compounds known as psoralens or furocoumarins. The chemical name is 9-methoxy-7H-furo[3,2-g][1]-benzopyran-7-one. The formulation of the drug is a sterile liquid at a concentration of 20 mcg/mL in a 10 mL vial. See http://www.therakos.com/TherakosUS/pdf/uvadexpi.pdf. Toxicology studies of extracorporeal photopheresis and different dosages of UVADEX® and ultraviolet light in beagle dogs is located in the investigator's brochure.

Next, the portion of the subject's blood, recipient's blood, or the donor's blood to which the photoactive compound has been administered is treated by subjecting the portion of the blood to photopheresis using ultraviolet light. The photopheresis treatment may be carried out using long wavelength ultraviolet light (UVA) at a wavelength within the range of 320 to 400 nm. Such a range is not limiting, however, but is merely provided as an example. The exposure to ultraviolet light during the photopheresis treatment may have a duration of sufficient length to deliver, for example, about 1–2 J/cm$^2$ to the blood.

The photopheresis step is carried out in vitro by installing irradiation chamber 700 into photoactivation chamber 750 of permanent tower system 2000 (FIGS. 17 and 18). In one embodiment, when the photopheresis step is carried out in vitro, at least a fraction of the treated blood is returned to the subject, recipient, or donor. The treated blood or the treated enriched leukocyte fraction (as the case may be) may then be administered back to the subject, recipient, or donor.

The photopheresis process consists of three phases including: 1) the collection of a buffy-coat fraction (leukocyte-enriched), 2) irradiation of the collected buffy coat fraction, and 3) reinfusion of the treated white blood cells. This process will be discussed below in greater detail. Generally, whole blood is centrifuged and separated in centrifuge bowl 10. A total of approximately 240 ml of buffy coat and 300 ml of plasma are separated and saved for UVA irradiation.

Figure 15:
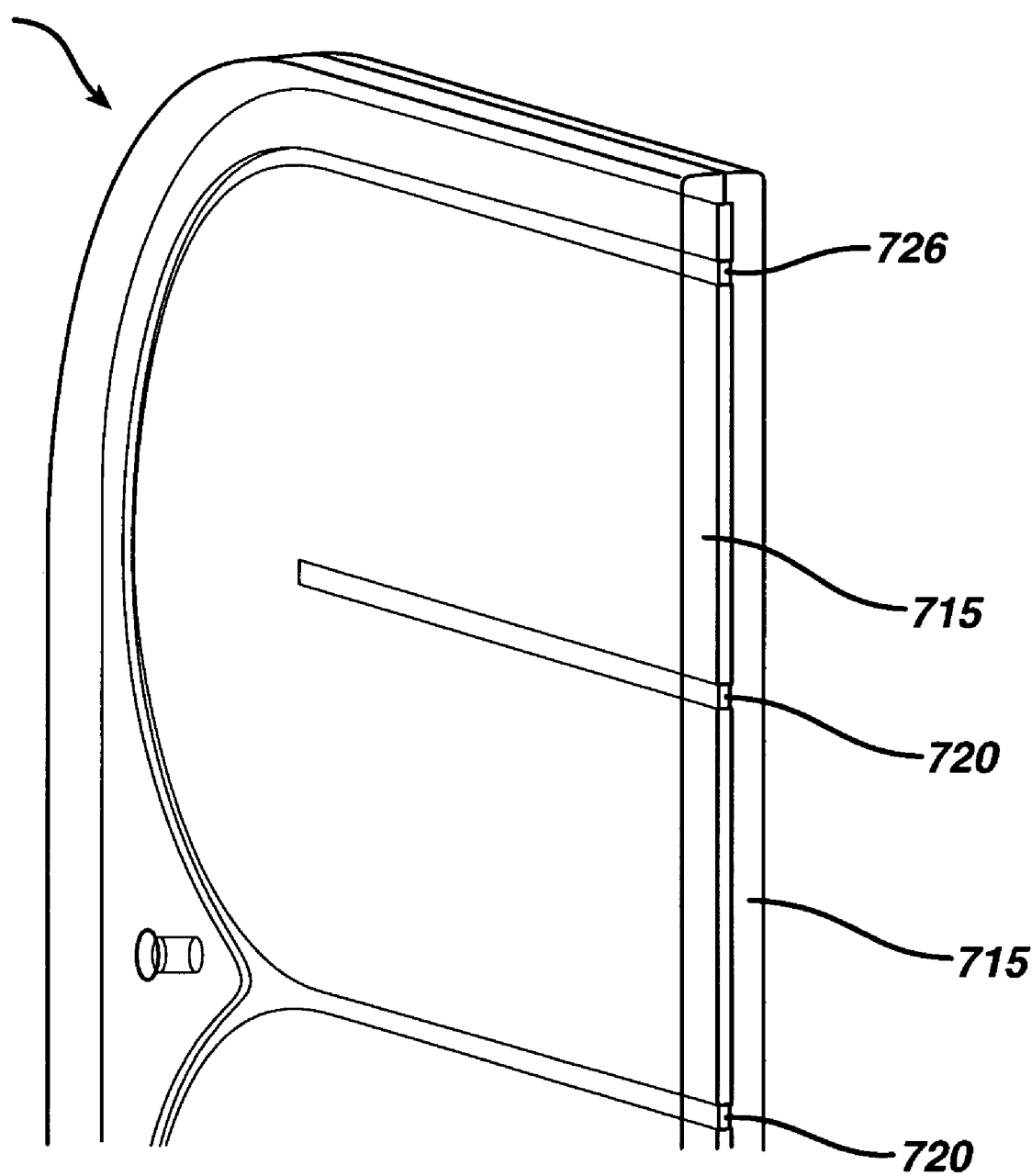
FIG. 15 is a cut-away dimensional end view of the irradiation chamber of FIG. 11.

The collected plasma and buffy coat are mixed with heparinized normal saline and UVADEX®. (water soluble 8-methoxypsoralin). This mixture flows in a 1.4 mm thick layer through the irradiation chamber of the present invention. The irradiation chamber 700, is inserted in photoactivation chamber 750 of tower system 2000 between two banks of UVA lamps of the PHOTOSETTE® (FIG. 15). PHOTOSETTE® UVA lamps irradiate both sides of this UVA-transparent irradiation chamber 700, permitting exposure to ultraviolet A light, yielding an average exposure per lymphocyte of 1–2 J/cm$^2$. Following the photoactivation period, the cells are removed from the irradiation chamber 700.

In a preferred embodiment of the present invention the cells are removed by the action of gravity and any cells remaining in the chamber are displaced from the chamber with additional fluid selected from the group consisting of saline, plasma, and combinations thereof. For patients who are small such as children (e.g. under 30 kg) or patients whose vascular system is easily overloaded with fluids the amount of additional fluid used to was the irradiation chamber will preferably be not more than 2× the volume of the chamber, preferably not more than 1× the volume of the chamber, more preferably not more than 0.5× the volume of the chamber 0.25× the volume of the chamber. The treated cells volume is reinfused to the patient.

For a description of similar photopheresis systems and methods, see U.S. patent application Ser. No. 09/480,893, which is expressly incorporated herein by reference. Also useful herein are the methods and systems described in U.S. Pat. Nos. 5,951,509; 5,985,914; 5,984,887, 4,464,166; 4,428,744; 4,398,906; 4,321,919; PCT Publication Nos. WO 97/36634; and WO 97/36581, all of which are entirely expressly incorporated herein by reference.

The effective amount of light energy that is delivered to the biological fluids may be determined using the methods and systems described in U.S. Pat. No. 6,219,584, which is entirely expressly incorporated herein by reference. Indeed, the application of ECP to the various diseases described herein may require an adjustment of the amount of light energy to optimize the treatment process.

Furthermore, the photosensitizing agent used in the ECP process may be removed prior to returning the treated biological fluid to the patient. For example, Methoxsalen (UVADEX®) is utilized in the ECP process. Methoxsalen belong to a group of compounds known as psoralens. The exposure to methoxsalen or other psoralens may cause undesirable effects on the subject, recipient, or donor such as phototoxicity or other toxic effects associated with psoralen and their decomposition products. Therefore, the psoralen, psoralen derivatives, or psoralen decomposition products that may remain in the biological fluid may be removed after UV exposure. A process for the removal of psoralen biological fluids is described in U.S. Pat. No. 6,228,995, which is entirely expressly incorporated herein by reference.

C. Centrifuge Bowl

In a specific embodiment, the present invention relates to methods and apparatus that separate fluid components, such as, for example, the components of a biological fluid by density or weight. Biological fluids encompass fluids that comprise, exist in, or are used in, or delivered to living organisms. Indeed, biological fluids may comprise bodily fluids and their components, such as blood cells, plasma, and other fluids that comprise biological components, including living organisms such as bacteria, cells, or other cellular components. Biological fluids may also comprise whole blood or specific whole blood components, including red blood cells, platelets, white blood cells, and precursor cells. In particular, it may be desirable to remove blood from a patient for treatment, such as for example, extracorporeal treatment. It is to be understood, however, that the present invention is adaptable to use with various centrifugal processing apparatus, and the specific example given herein is merely for illustrative purposes. Other uses for the separation techniques and apparatus may include other medical processes such as dialysis, chemotherapy, platelet separation and removal, and separation and removal of other specific cells. Additionally, the present invention may be used to separate other types of fluids that include a wide variety of non-medical uses, such as, for example, oil and fluid component separation. All components used in the present invention should not adversely affect biological fluids or render them unsuitable for their intended uses, such as those described herein and may be made of any suitable material compatible with uses described herein including, but not limited to plastics, such as polycarbonate, methyl methacrylate, styrene-acrylonitrile, acrylic, styrene, acrylonitrile or any other plastic. Where parts of the present invention are indicated to be attached together and form a fluid tight seal any appropriate conventional means of joining the parts may be used including but not limited to, adhesives, ultrasonic welding or RF welding.

The present invention has several advantages over centrifuges what use conventional Latham bowl. The Latham bowl in the UVAR® XTS™ system has one inlet port that allows whole blood to come into the bowl and one outlet port that allows plasma and buffy coat to come out. Having only two ports limits the volume of buffy coat that can be collected per cycle. Each cycle involves filling the bowl with whole blood; 2) spinning the bowl to separate whole blood into plasma, buffy coat, and red blood cells; 3) collecting buffy coat for treatment, 4) bringing the bowl to rest; and 5) returning collected plasma and red blood cells. This buffy coat collection method may be characterized as being "batch-like" as the volume of buffy coat required for irradiation treatment can only be collected after several cycles of buffy coat collection. The limited volume of collected buffy coat per cycle results from the accumulated red blood cells remained inside the bowl. Thus the accumulated red blood cells that can only be emptied at the end of a buffy coat collection cycle is an inherent limitation of the Latham Bowl.

The bowl of the instant invention has three separate fluid conduits that can be used as an inlet port and two outlet ports. The additional fluid conduits allows for 1) reduce patient treatment time by having continuous spinning during the entire buffy coat collection process without having to stop spinning the bowl for removal of accumulated red blood cells; 2) treat small blood volume patients; by having collected red blood cells returned to patients continuously, these patients may be more amenable to medical treatments requiring the use of the buffy coat or fractions thereof such as extracorporeal photopheresis; 3) better separation of different components of fractions of cells within the buffy coat due to the increased spinning or rotation time and 4) the ability to separate high density red blood cells fractions from whole blood. This centrifuge bowl also provides the opportunity for reduced treatment time for any medical procedure requiring buffy coat fractions to be collected from patients that are substantially free of red blood cells, such as extra corporeal photopheresis.

Figure 35:
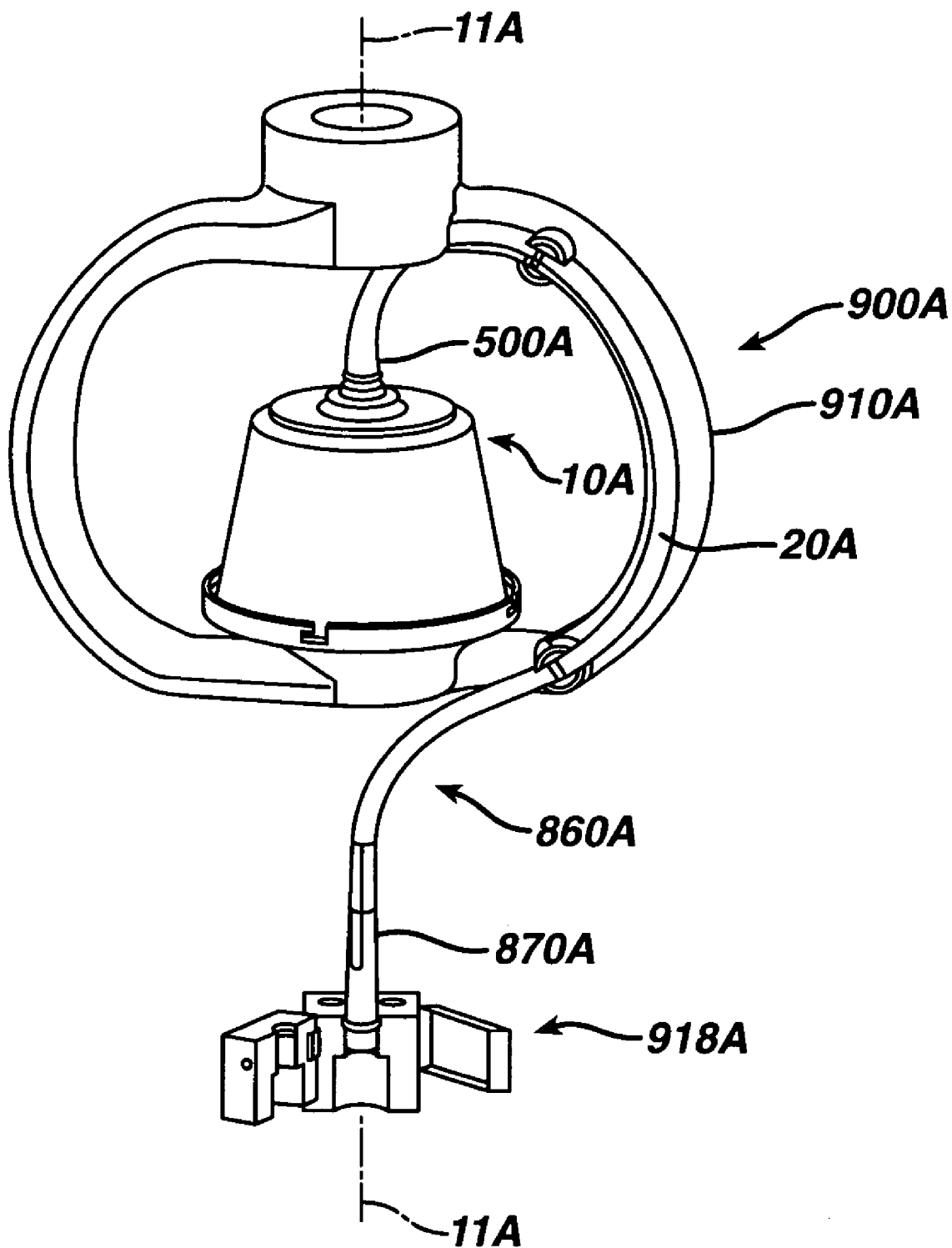
FIG. 35 illustrates an embodiment of a centrifuge bowl and a rotating frame.
Figure 36:
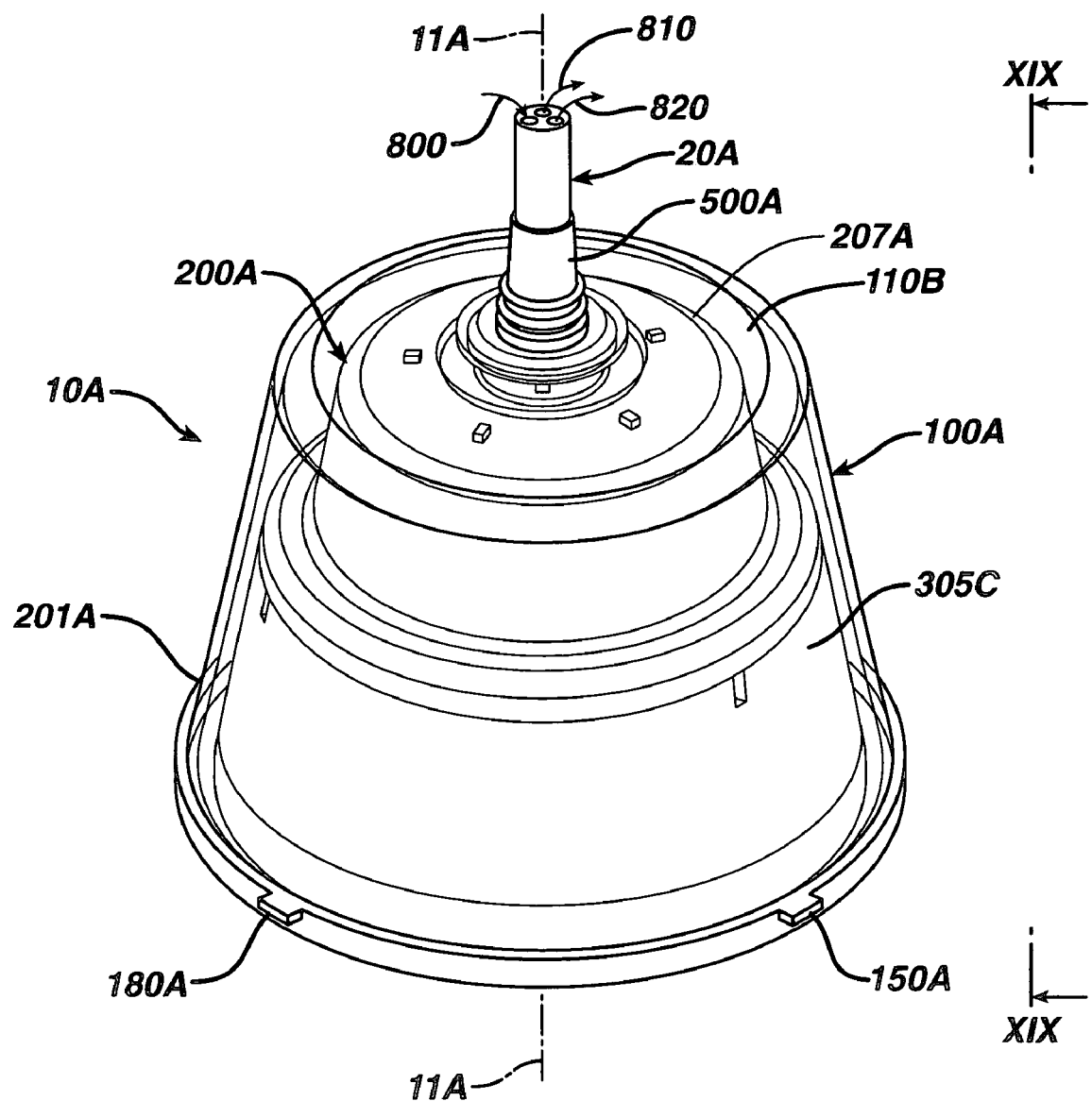
FIG. 36 is a dimensional view of the bowl of FIG. 35.

To achieve the objects in accordance with the purpose of the present invention, as embodied and broadly described herein, FIGS. 35 and 36 depict specific embodiments of the present invention. The embodiment depicted in FIG. 35 comprises a centrifuge bowl 10A, conduit assembly 860A, frame 910A and stationary restraint 918A. The centrifuge bowl 10A is in fluid communications with external conduit 20A of conduit assembly 860A. Lower sleeve end 832A (FIG. 46) of connection sleeve 500A is secured to bowl 10A. Upper sleeve end 831A of connection sleeve 500A is secured to external conduit 20A, connecting the external conduit 20A to bowl 10A and providing fluid communications from external conduit 20A to bowl 10A. The fluid communications enables fluid 800 to be supplied through external conduit 20A to the bowl 10A. Similarly this fluid communications also enables separated fluid components 810 and 820 to be removed from bowl 10A through external conduit 20A. Bowl 10A and frame 910A are adapted to be rotated around center axis 11A.

Referring to FIG. 36, bowl 10A comprises outer housing 100A, connection sleeve 500A, top core 200A, bottom core 201A, and housing floor 180A. Outer housing 100A may be constructed of any suitable biocompatible material as previously described for the purpose of the illustration in FIG. 36 the outer housing 100A is constructed of clear plastic so that cores 200A and 201A are visible there through. Outer housing 100A is attached to a housing floor 180A, which in turn comprises protrusions 150A for locking bowl 10A into a rotational device such as rotational device 900A. Bowl 10A is preferably simplified in construction and is easy to manufacture by molding or other known manufacturing processes, such that it may be disposable or used for a limited number of treatments, and is most preferably capable of containing about 125 ml of fluid, such fluid possibly being pressurized. In alternative embodiments, the volume capacity of the bowl may vary depending upon the health of the patient and his or her allowable extracorporeal volume. The volume capacity of the bowl may also vary depending upon the use of the bowl or the particular treatment for which the bowl is utilized. Additionally, to avoid contamination of biological fluids, or exposure of persons involved in the processing operation to the fluids, the transfer operations are preferably carried out within a sealed flow system, possibly pressurized, preferably formed of flexible plastic or similar material which can be disposed of after each use.

Figure 37:
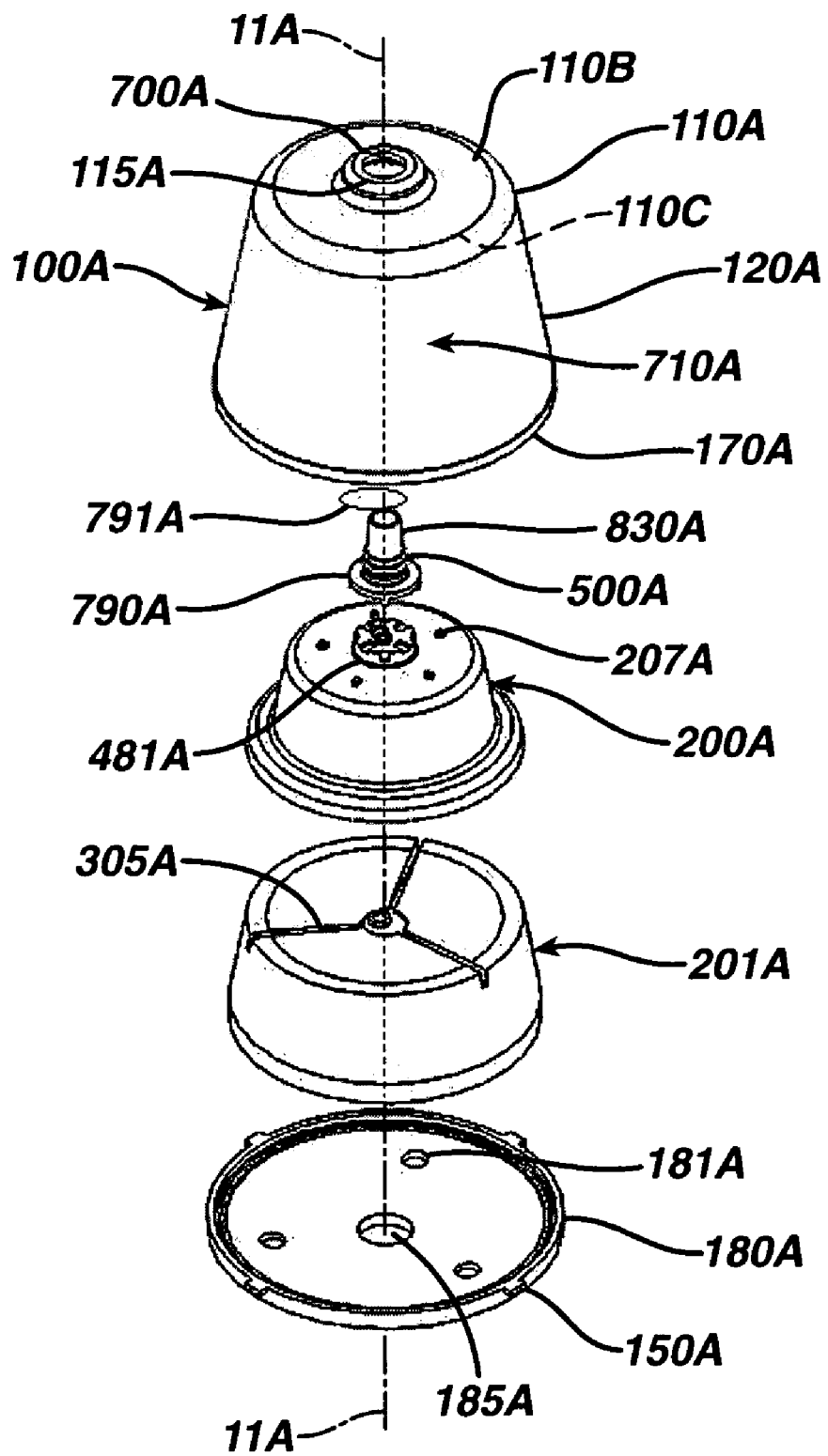
FIG. 37 is an exploded view of the bowl of FIG. 36.

As is illustrated in FIGS. 36 and 37, the outer housing 100A is substantially conical having an upper housing end 110A, an outer housing wall 120A and a lower housing end 190A. Outer housing 100A may be made of plastic (such as those plastics listed previously), or any other suitable material. Upper housing end 110A has an outer surface 110B, inner surface 110C and housing outlet 700A providing a passage between said surfaces. Preferably the upper housing will also have a neck 115A formed about the housing outlet 700A. The housing outlet 700A and neck 115A are sized to allow body 830A of the connection sleeve 500A to pass through while retaining sleeve flange 790A, which extends from the body 830A of connection sleeve 500A. In one embodiment of the present invention an o-ring 791A may be inserted between the sleeve flange 790A and inner surface 110C of the housing end 110A to ensure a fluid tight seal is provided. In an alternative embodiment of the present invention illustrated in FIG. 53, a second sleeve flange 790B extends from the body 830A of connection sleeve 500B distal to the sleeve flange 790A. Both sleeve flange 790A and 790B being adapted to fit within neck 115A and retain o-ring 791A therebetween. A fluid tight seal is provided in this embodiment by the o-ring contacting body 830A and inner surface 110C of the housing end 110A adjacent to the neck 115A. However, connection sleeve 500A can be secured to bowl 10A by any suitable means, including for example, a lip, groove, or tight fit and adhesive with a component of bowl 10A. The outer housing wall joins the upper housing end 110A and lower housing end 190A. Lower housing end 190A is attached to a housing floor 180A of greater diameter than upper end 110A. Housing floor 180A is adapted to mate with the lower housing end 190A and provide a fluid tight seal therewith. Any conventional means may be used to secure the lower housing end 190A to the housing floor 180A, including but not limited to, adhesives, ultrasonic welding or RF welding. Housing floor 180A may have an indentation 185A that is used to collect denser fluid 810. The diameter of outer housing 100A increases from upper housing end 110A to lower housing end 190A.

Figure 51:
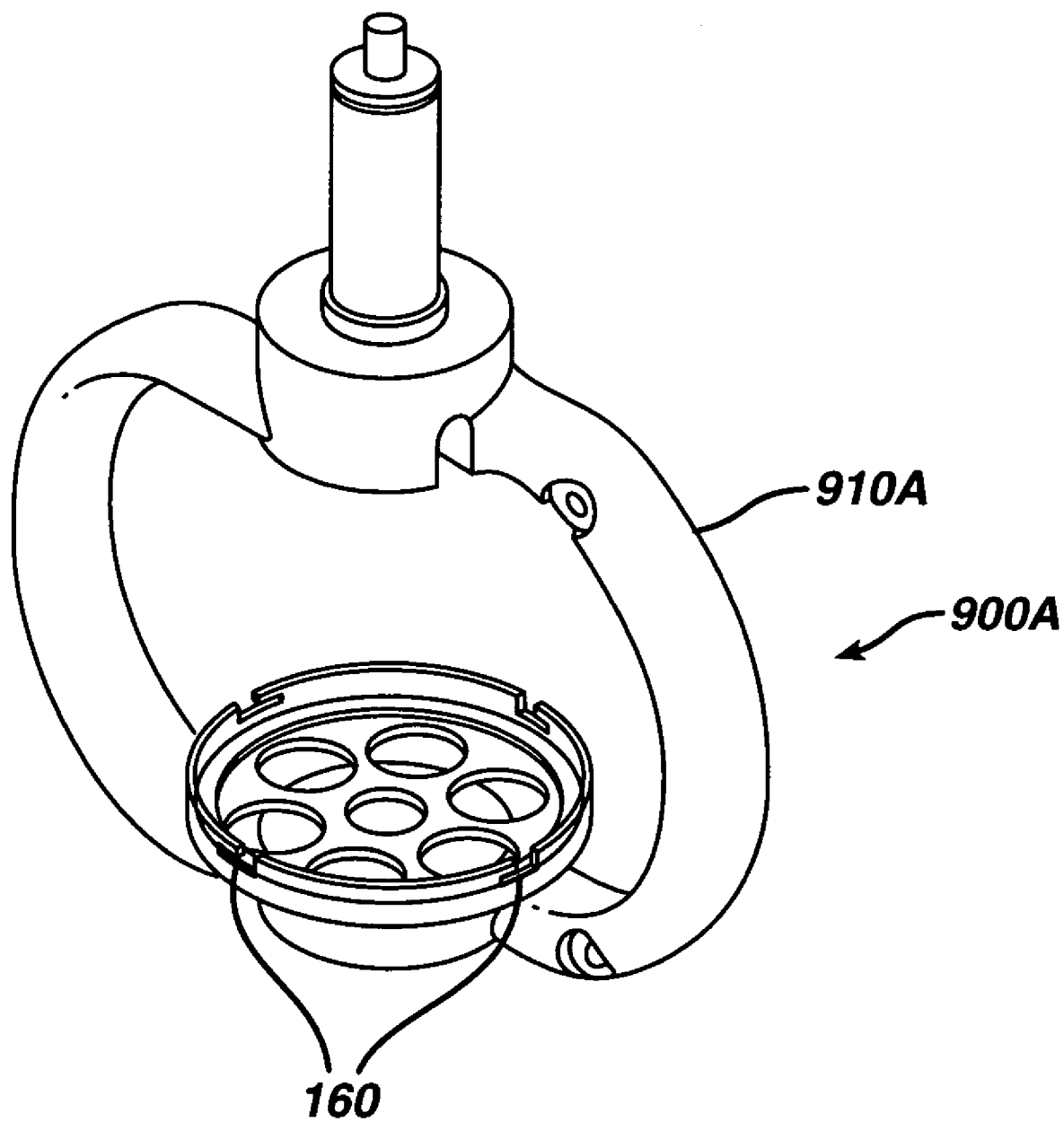
FIG. 51 illustrates a dimensional view of the rotating frame of FIG. 35.
Figure 52:
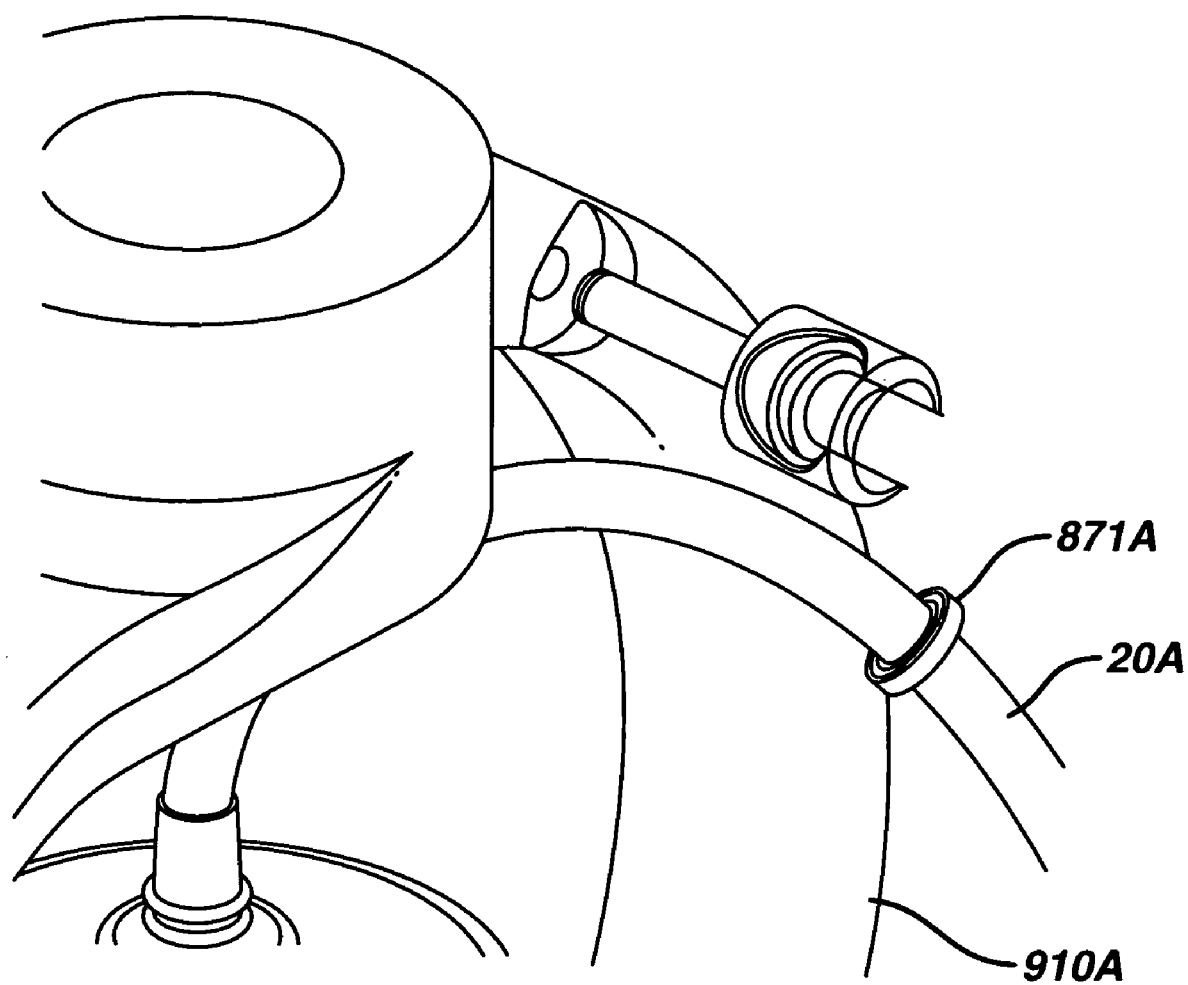
FIG. 52 is an enlarged view of a holder for an external conduit.

Outer housing 100A is adapted to rotatably connect to a rotational device 900 (FIG. 35), such as for example, a rotor drive system or a rotating bracket 910. The rotatable connection may, for example, be a bearing that allows free rotation of bowl 10A. Outer housing 100A preferably has a locking mechanism. The locking mechanism may be one or more protrusions 150A designed to interact with corresponding indentations in a centrifuge container or any other suitable interconnect or locking mechanism or equivalent known in the art. The locking mechanism may also comprise a key slot 160 (FIG. 51).

Referring to FIG. 37, outer housing 100A and the base 180A define an interior volume 710A in which cores 200A and 201A will fit when bowl 10A is assembled. When fully assembled, cores 200A and 201A are fully within interior volume 710A of outer housing 100A, occupying a coaxial volume of interior volume 710A about axis 11A.

Figure 38:
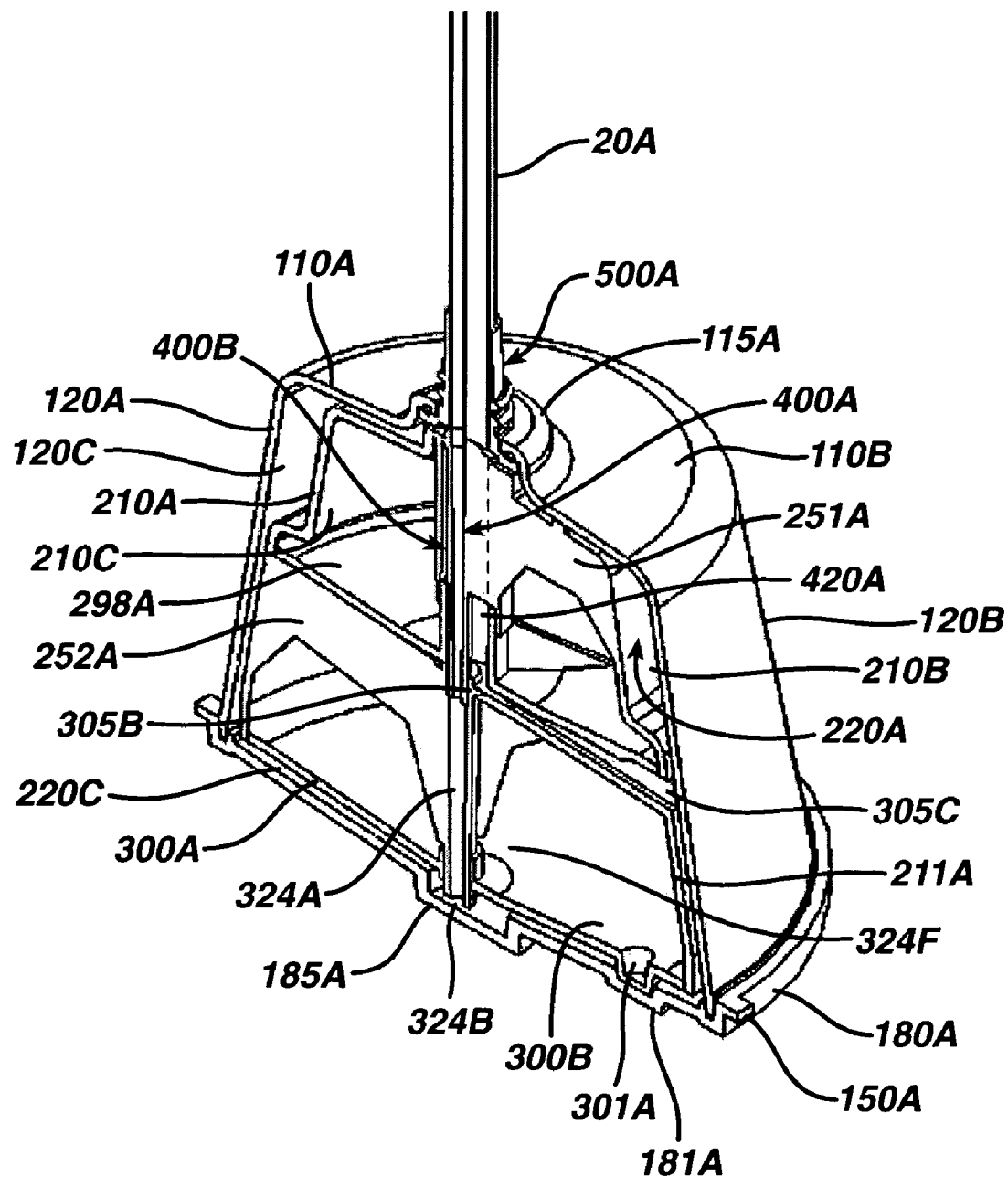
FIG. 38 shows a cross sectional view of the bowl of FIG. 36 along the line XIX—XIX.
Figure 40:
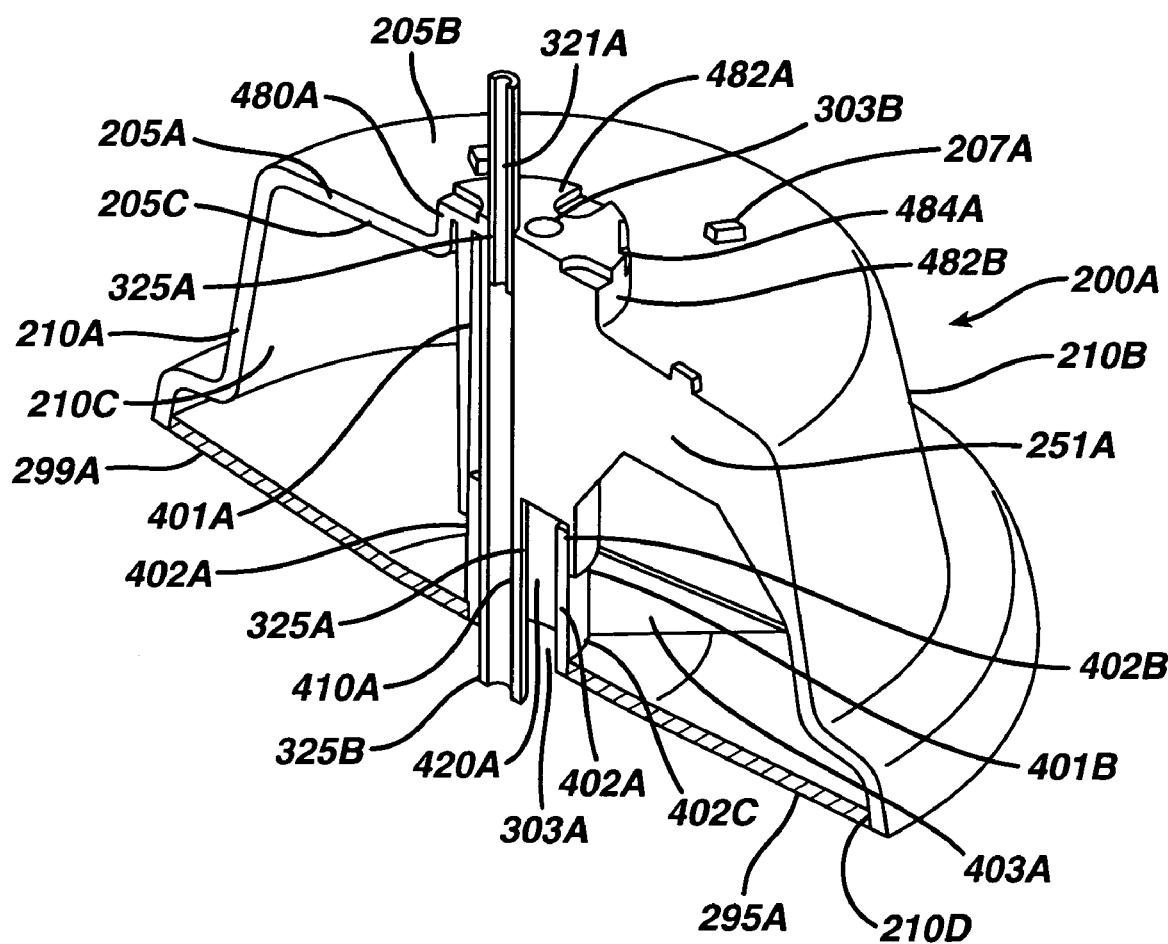
FIG. 40 shows a cross sectional view of the top core of the bowl of FIG. 37.
Figure 44:
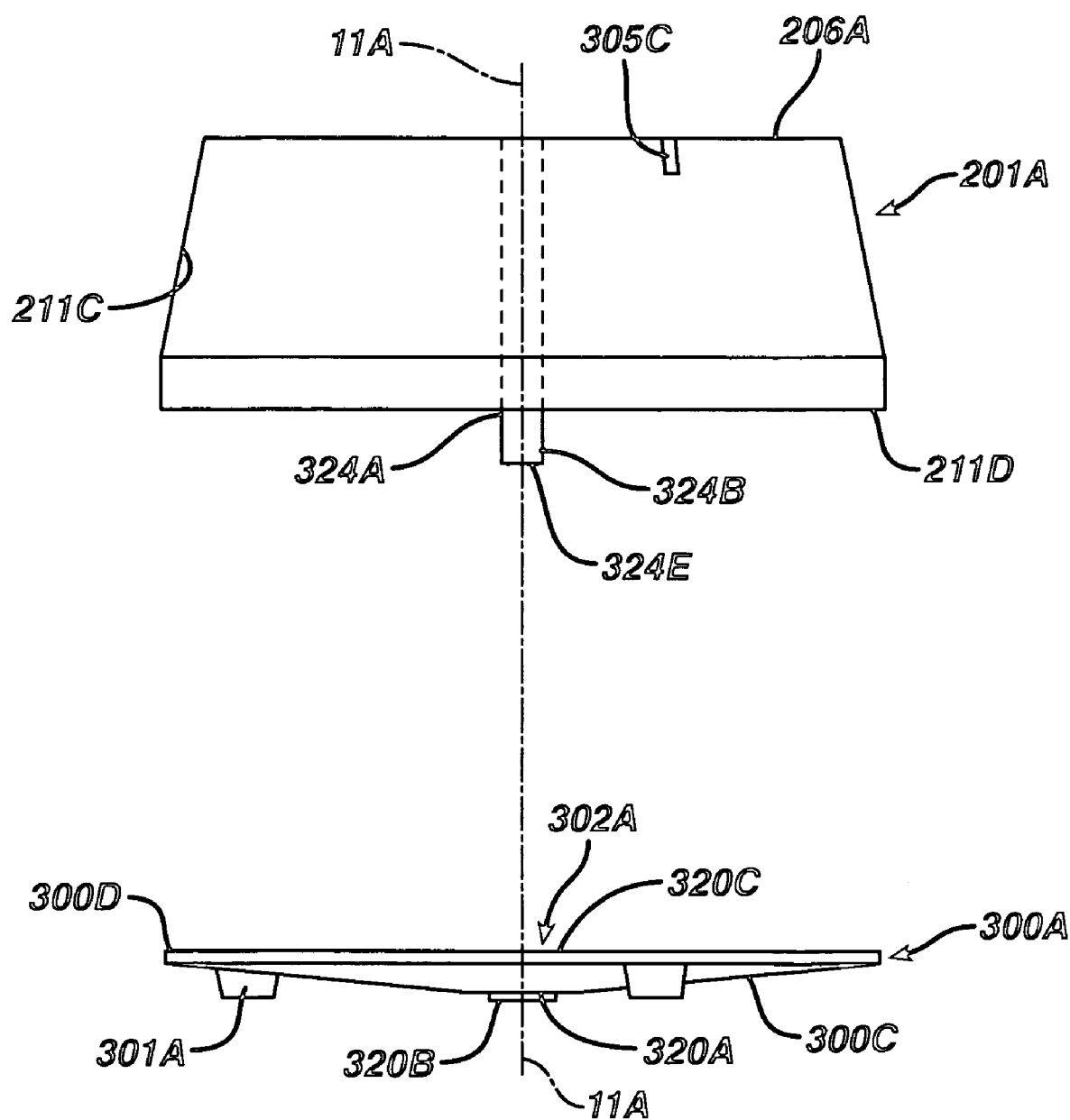
FIG. 44 shows an exploded side view of the bottom core and a lower plate of FIG. 43A.

Referring to FIGS. 38, 40 and 44, the top core 200A and bottom core 201A are substantially conical and respectively have upper core ends 205A, 206A; outer core walls 210A, 211A; and lower core ends 295A, 296A. The cores 200A, 201A occupy coaxial volumes of interior volume 710A of bowl 10A and forming separation volume 220A between upper end 205A and outer wall 210A of top core 200A and outer wall 211A and lower core end 296A of bottom core 201A and outer housing 100A. Separation volume 220A is that space of interior volume 710A that is between cores 200A and 201A and outer housing 100A.

Figure 41:
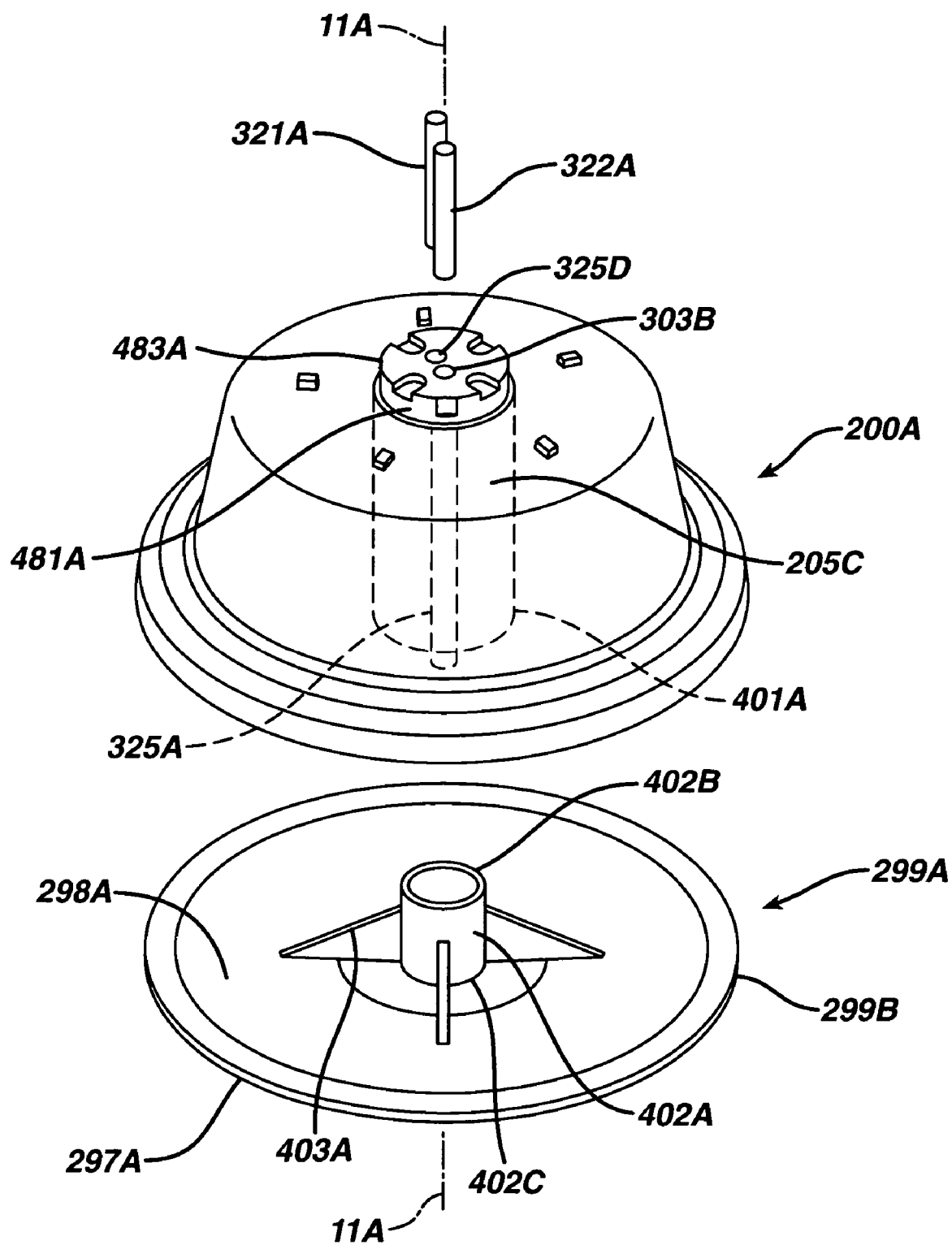
FIG. 41 shows a dimensional view of the top core and upper plate of FIG. 37.
Figure 42:
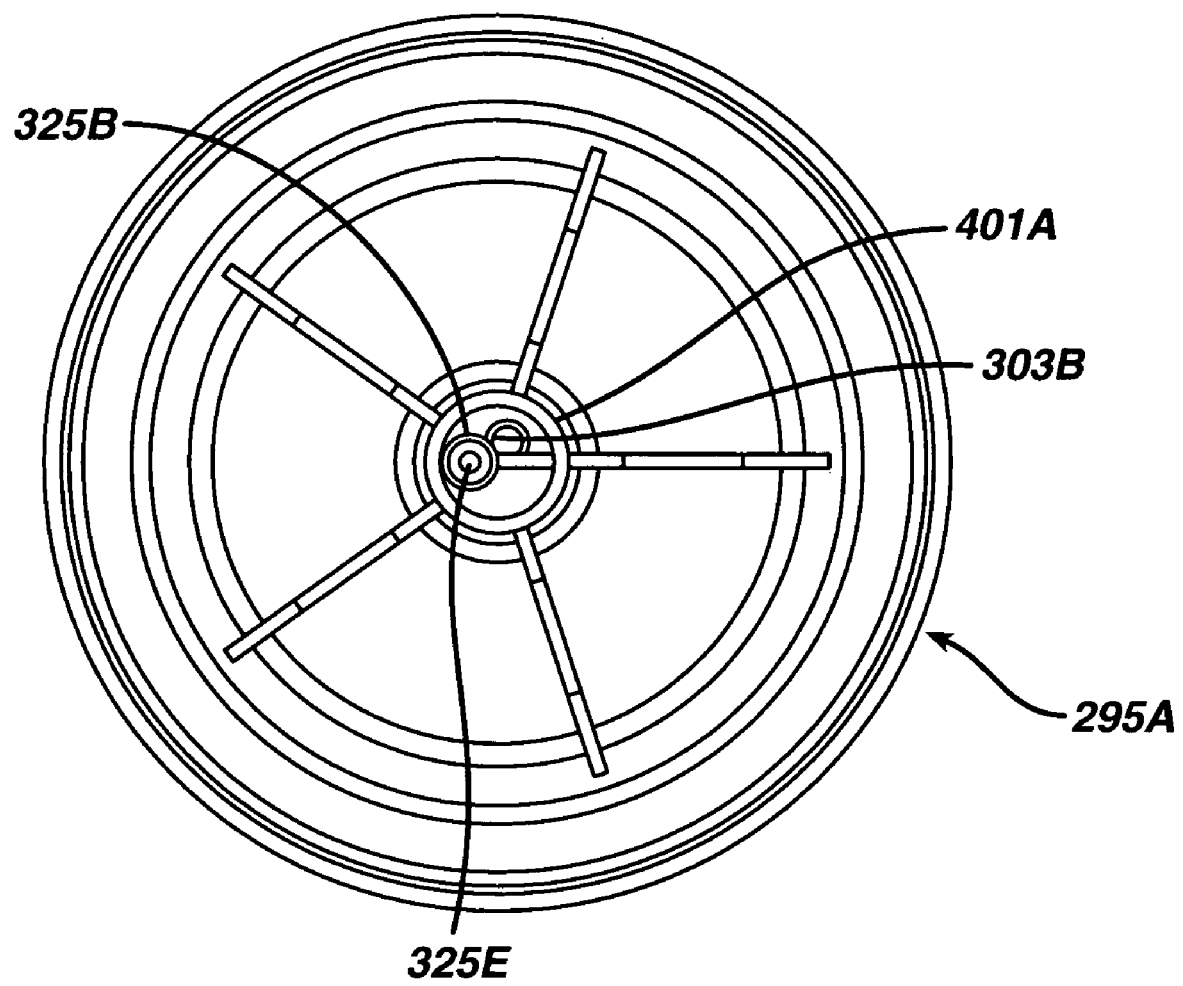
FIG. 42 shows a bottom view of the top core of FIG. 41.

As depicted in FIGS. 40 and 41 top core 200A comprises upper core end 205A and a lower core end 295A that are joined by outer core wall 210A. The outer core wall 210A having an outer surface 210B and inner wall surface 210C and a lower edge 210D. The diameter of top core 200A preferably increases from upper core end 205A to lower core end 295A. Upper core end 205A also comprises an outer surface 205B and an inner surface 205C. Centrally located about center axis and extending perpendicularly from the upper surface 205B is lumen connector 481A. Lumen connector 481A has a top surface 482A and a wall surface 482B. Top surface 482A has two passages 303B and 325D that provide fluid communications through the upper core end 205A with second bowl channel 410A and first bowl channel 420A respectively. Second bowl channel 410A is a conduit that has a conduit wall 325A that extends perpendicularly from the inner surface 481C of lumen connector 481A.

Figure 39B:
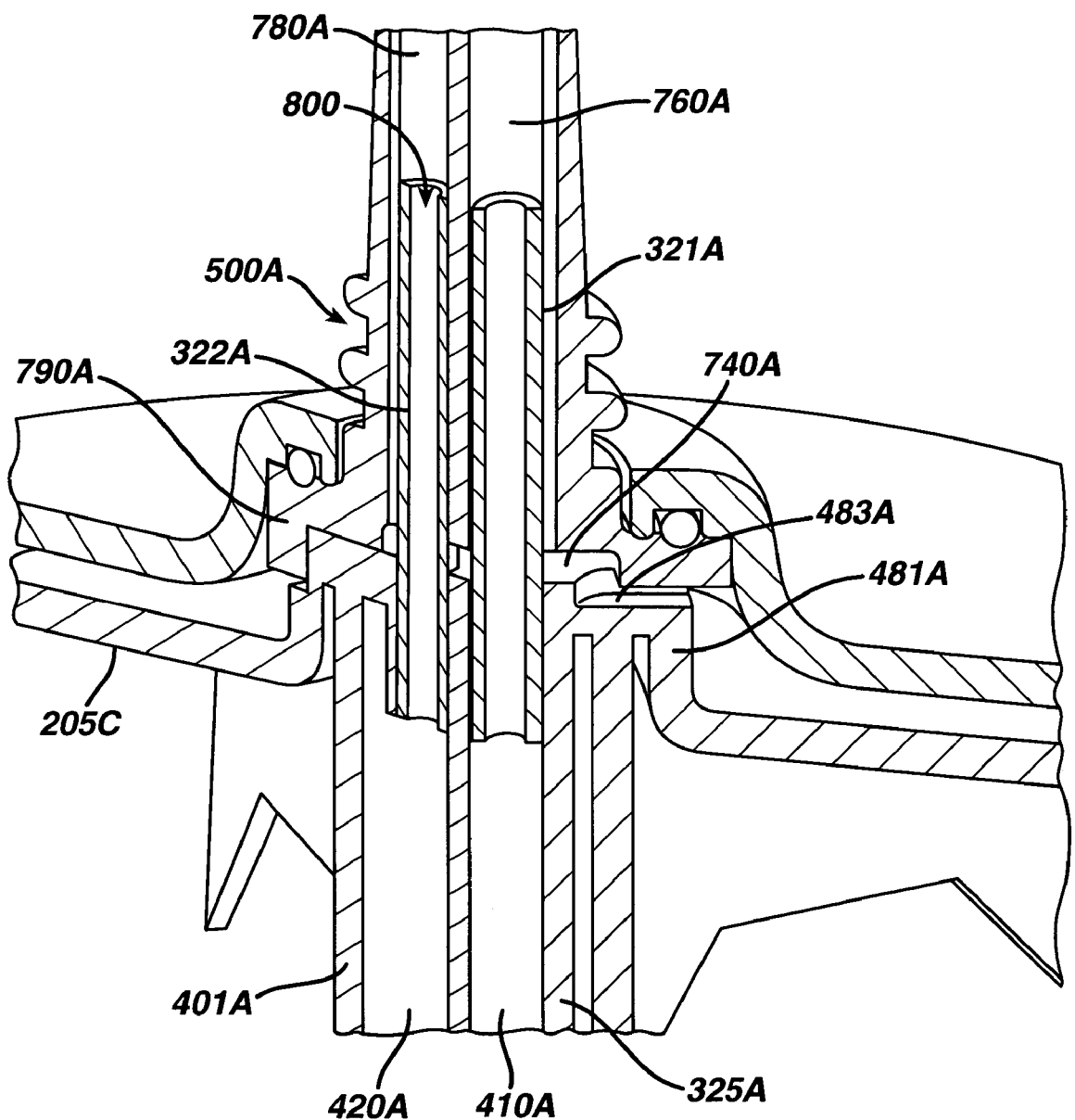
FIG. 39B shows another cross sectional view of a connection sleeve in place with a lumen connector of the bowl of FIG. 38.

As shown on FIGS. 39B, 39A and 40, second bowl channel 410 has fluid communication with conduit channel 760A through conduit 321A having a first end 321B and a second end 321C that is adapted to fit into passage 325D of lumen connector 481A. In operation conduit channel 760A of external conduit 20A has fluid communication with bowl channel 410A. First bowl channel 420A is a second conduit that has a channel wall 401A that extends substantially perpendicularly from inner surface 481C of the lumen connector 481A. As shown in FIGS. 39A, 39B and 40, first bowl channel 420A has fluid communication with conduit channel 780A of external conduit 20A through hollow cylinder 322A having a first end 322B and a second end 322C adapted to fit opening 303B top surface 482A. As is illustrated in one embodiment of the present invention, second bowl channel 410A is disposed within first bowl channel 420A. In an alternative embodiment of the present invention illustrated in FIG. 53, conduit wall 325A may be composed of upper part 325F and lower part 325G and be fused with channel walls 401A and 402A.

Top surface 482A also has indentation 483A which provides fluid communications with chamber 740A. When assembled, chamber 740A is defined by lumen mounting recess 851A less the volumes occupied by hollow cylinders 321A and 322A in the connection junction of connection sleeve 500A and lumen connector 481A. Chamber 740A has fluid communication with conduit channel 770A and with separation volume 220A near neck 115A through indentation 483A. Thus indentation 483A forms a passageway for the removal of second separated fluid component 820 through bowl chamber 740A. Optionally present on the outer surface 205B are a plurality of spacers 207A which extend from the outer surface and contact the inner surface 110C of the upper housing end 110A to ensure fluid communications between the separation volume 220A and the passageway formed by the indentations 483A.

Figure 53:
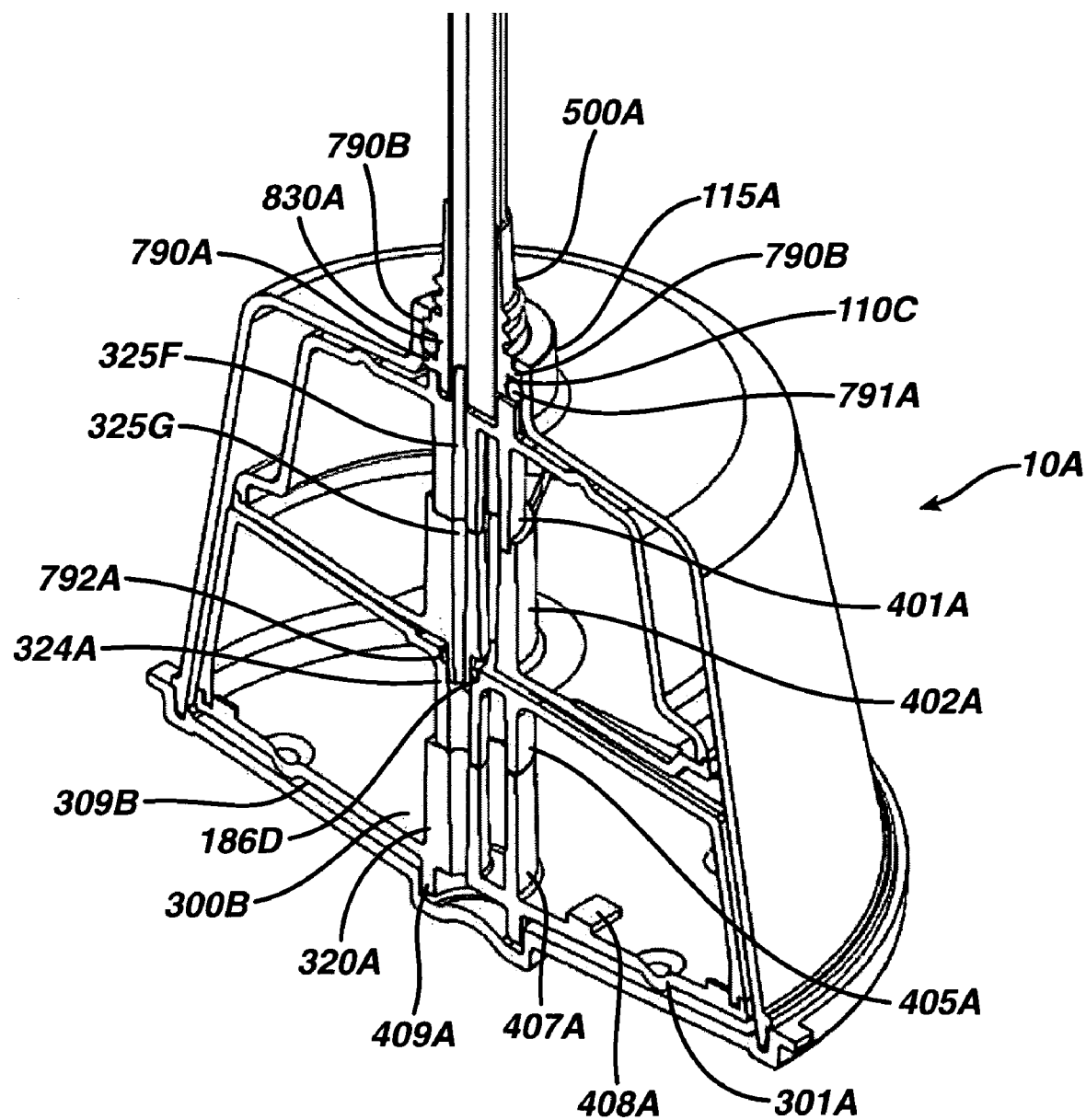
FIG. 53 shows an alternative embodiment of the bowl with the cross-section taken similarly to that shown in FIG. 38.
Figure 54:
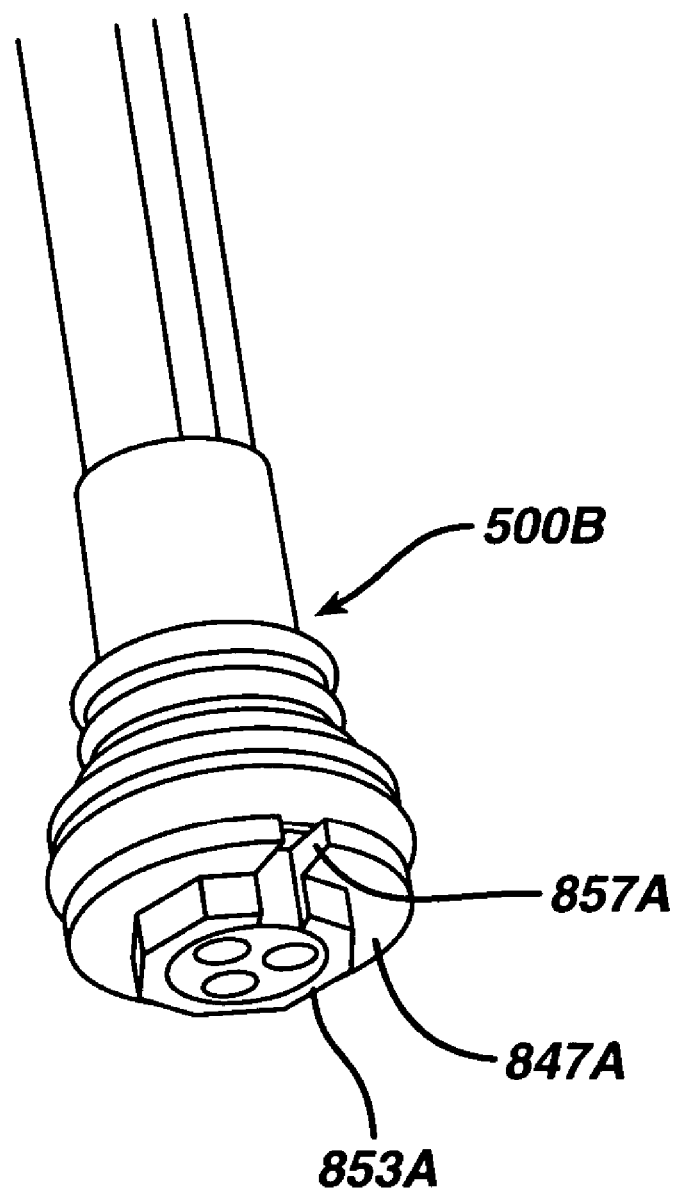
FIG. 54 shows an alternative embodiment of the top core.
Figure 55:
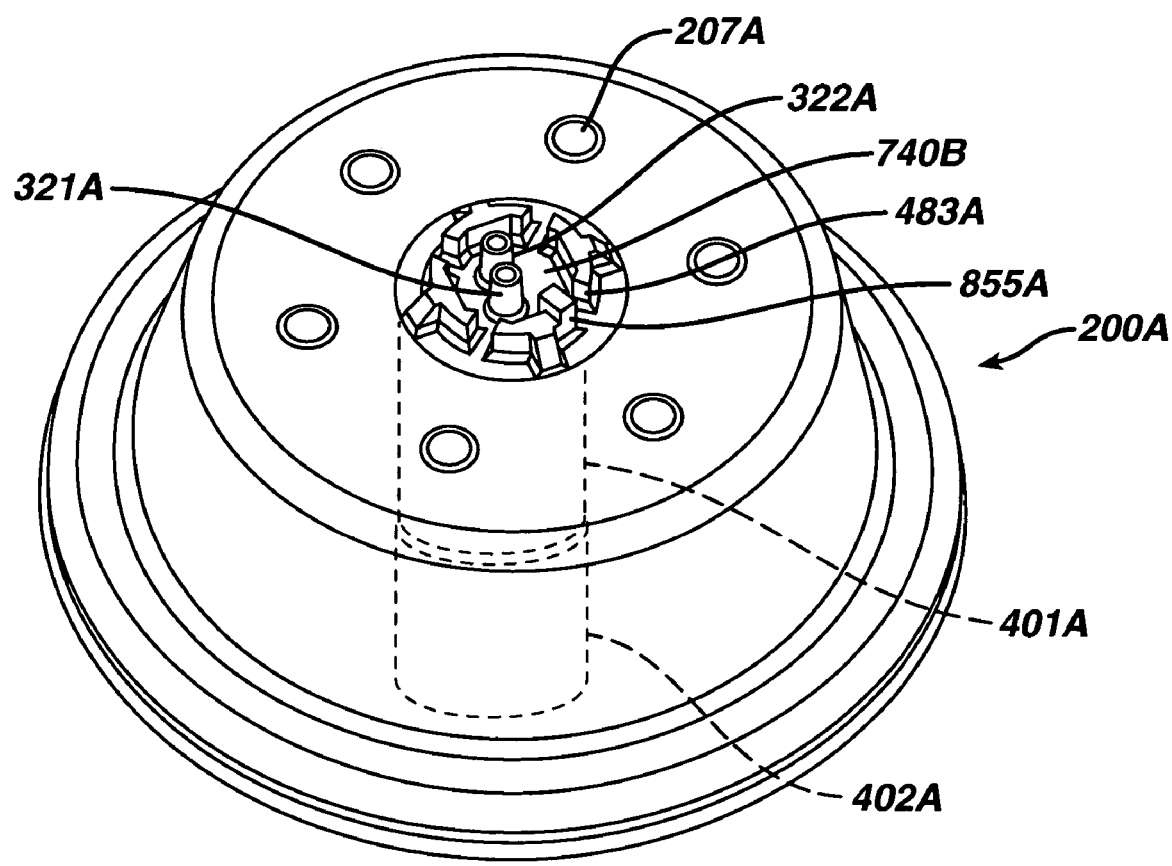
FIG. 55 shows an alternative embodiment of the connection sleeve.

In an alternative embodiment illustrated in FIGS. 53, 54 and 55, conduits 321A and 322A may be affixed to openings 325D and 303B in the top surface 482A of the lumen connector 481 A. Additionally, indentations 483A may form a plurality channels in the lumen connector 481A and be adapted to form chamber 740B when connected to connection sleeve 500A or 500B. Chamber 740B is adapted to have one or more surfaces 742A that can mate with the male end 853A of the connection sleeve 500A (male end 853A surrounds end 861 of external conduit 20A). To facilitate the correct orientation of the connection sleeve 500A to the lumen connector 481A the shape of the male end 853A and chamber 740B may be nonsymmetrical or as is illustrated in FIGS. 53, 54 and 55 a guide 855A may be provided which extends from the top surface of the lumen connector 481A and is adapted to fit within opening 857A of the sleeve flange 790A.

Referring back to FIG. 40, the lower core end 295A comprises an upper plate 299A having a top surface 298A, a bottom surface 297A, and an edge 299B that attaches and makes direct contact with lower edge 210D of the outer core wall 210A. The edge 299B of the upper plate 299A is adapted to be joined with lower edge 210D of outer core wall 210A and form a fluid tight seal therewith. Extending perpendicularly from the top surface 298A of upper plate 299A is a channel wall 402A, having an upper end 402B and a lower end 402C and surrounds opening 303A which is substantially in the center of upper plate 299A. A number of fins 403A, attached to the outside surface of channel wall 402A and top surface 298A, supports lumen wall 402A. The channel wall 402A is adapted to mate with channel wall 401A forming a fluid tight seal and providing lumen 400A. First bowl channel 420A is in fluid communications with conduit channel 780A of external conduit 20A through conduit 322A. Opening 303A provides fluid communications from lumen 400A to separation volume 220A as will be further discussed. First bowl channel 420A also surrounds second bowl channel 410A.

Figure 43A:
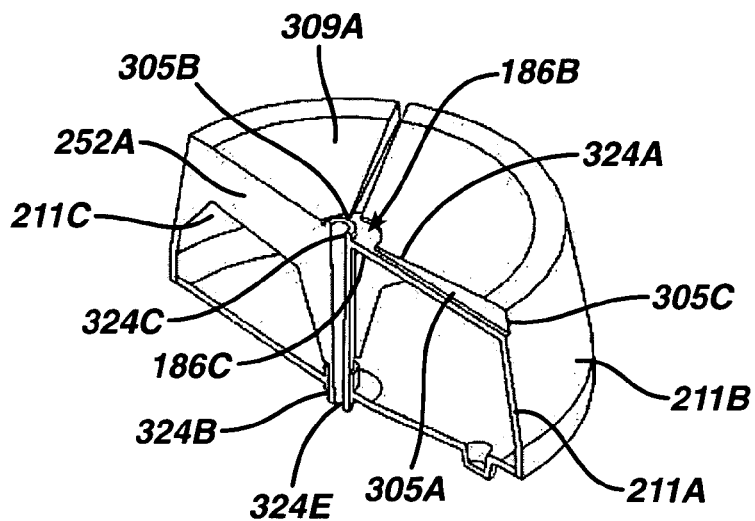
FIG. 43A shows a dimensional exploded view of the bottom core and a lower plate of the bowl of FIG. 37.
Figure 43B:
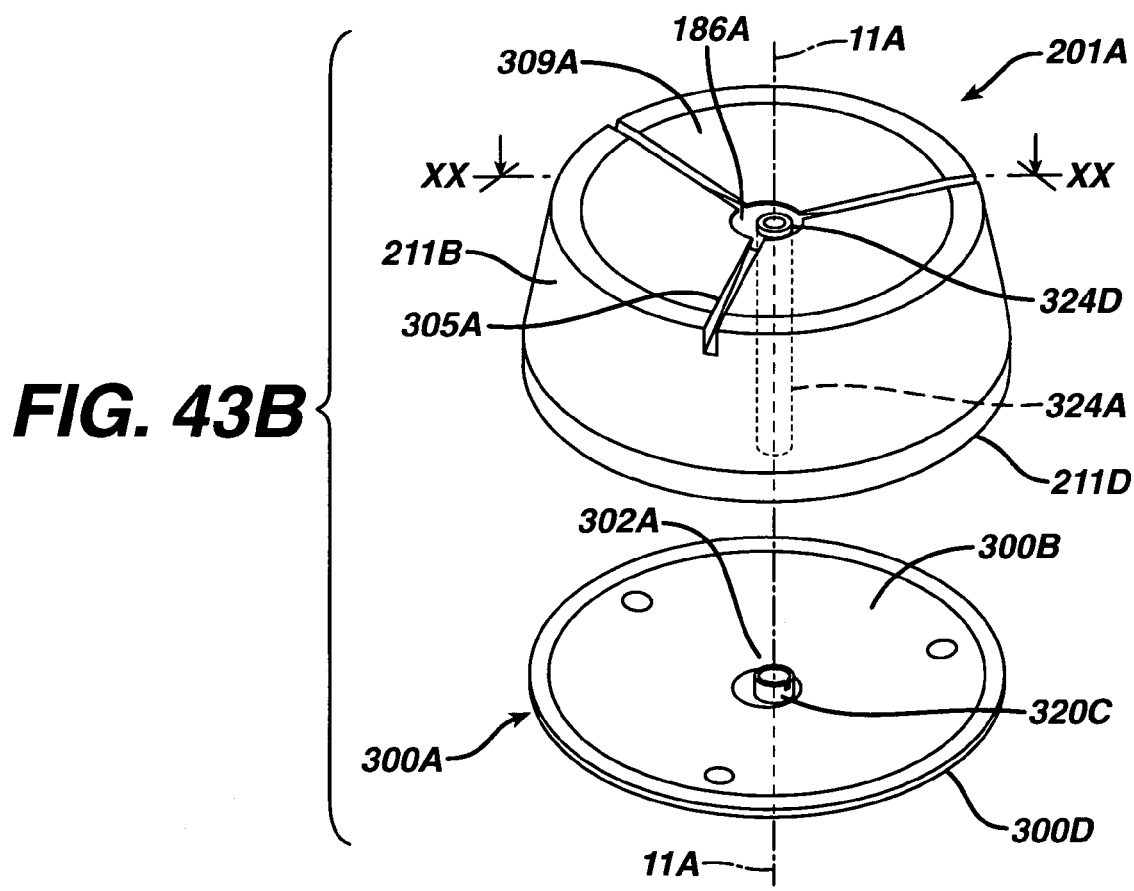
FIG. 43B shows an dimensional cross section view of the bottom core and a lower plate of the bowl of FIG. 43A attached together.

Referring to FIGS. 43A, 43B and 44, bottom core 201A comprises an upper core end 206A, a outer core wall 211A and a lower core end 296A. The outer core wall 211A having an outer surface 211B, an inner wall 211C and lower edge 211D. The diameter of bottom core 201A preferably increases from upper core end 206A to lower core end 296A. Bottom core 201A also has a top surface 309A and a bottom surface 309B. Top surface 309A has an indentation 186A (preferably generally circular) substantial in the center of the surface 309A of the upper core end 206A. The indentation 186A has an upper surface 186B and an inner surface 186C. The upper surface 186B of the indentation 186A has therein an opening 324D which extends through to the inner surface 186C. In an alternative embodiment of the present invention illustrated in FIG. 53, the upper surface 186B, may also have a recess a186D adapted to receive an o-ring and form a fluid type seal around the lower end of 325B of conduit wall 325A. Extending perpendicularly from inner surface 186C around said opening 324D is conduit wall 324A having a distal end 324B. On the top surface 309A extending from the indentation 186A to the outer surface 211B of the outer core wall 211A are one or more channels 305A. The top surface 309A may be horizontal or slope upward or downward from indentation 186A. If top surface 309A slopes upward or downward from indentation 186A to core end 206A, one skilled in the art would be able to adjust the shapes of upper plate 299A and upper core end 295A accordingly. Channels 305A may have an even depth through out the length of the channel 305A. However, channel 305A may slope downward or upward radially from the center. One skilled in the art would see that if top surface 309A slopes upward or downward and channel 305A has a constant depth, then channel 305A slopes upward or downward accordingly.

Referring to FIG. 38, the bottom surface 297A of upper plate 299A is in direct contact with the top surface area 309A of bottom core 201A when completely assembled. This contact forms a fluid tight seal between the two surface areas forming an opening 305B from the indentation 186A to channel 305A. A second opening 305C from channel 305A is formed in the outer surface 211B of outer core wall 211A. The opening 305B provides fluid communications from indentation 186A through channel 305A and opening 305C to separation volume 220A (FIGS. 38 and 40). Thus fluid 800 flows through conduit channel 780A and subsequently passes through first bowl channel 420A. From first bowl channel 420A, fluid 800 then goes to through channel 305A to the separation volume 220A.

Referring to FIGS. 43A and 44, the lower core end 296A has a lower plate 300A, which has a top surface 300B, a bottom surface 300C and outer edge 300D. Extending from the bottom surface 300C of the lower plate 300 are one or more protrusions 301A. The outer edge 300D is adapted to be attached to the lower edge 211D of the outer core wall 211A and provide a fluid tight seal therewith. Positioned above housing floor 180A, lower plate 300A is circular and curves upward radially from its center (illustrated in FIG. 44). Alternatively, lower plate 300A can be flat. As shown in FIG. 38 when positioned above housing floor 180A, a volume 220C exists between lower plate 300A and housing floor 180A. This volume 220C is in fluid communication with separation volume 220A. Lower plate 300A may be made of plastic or any other suitable material. Additionally, extending substantially perpendicularly from the lower surface 300C of lower plate 300A is a conduit 320A. Conduit 320A has a first end 320B that extends into the space 220C between lower plate 300A and housing floor 180A and a second end 320C that extends above the top surface 300B of lower plate 300A. The diameter of conduit 320A is adapted to have a tight fit with conduit wall end 324B. The volume inside conduit walls 324A and 325A comprises a lumen 400B. The volume defined by lower plate 300A, inner surface 211C, and ceiling 253A of bottom core 201A, excluding second bowl channel 410A, may comprise of air or a solid material (See FIGS. 43B and 44).

In an alternative embodiment of the present invention as illustrated in FIG. 53, support walls 405A and 407A may be optionally present. Support wall 405A extends perpendicularly from bottom surface 309B. Support wall 407A extends perpendicularly from the top surface 300B of lower plate 300A and connects with support wall 405A when the bottom core 201A is assembled. Conduit wall 324A may be connected to conduit 320A to form a fluid tight seal and conduits 324A, 320A may be fused respectively with supports walls 405A and 407A. Additionally present extending from the bottom surface 300C of lower plate 300A are one or more orientation spacers 409A that mate within indentation 185A.

As will be readily apparent to one of ordinary skill in the art, the bowl 10A will need to be balanced about center axis 11A. Accordingly, weights may be added as part of the device as is appropriate to facilitate the balancing of the bowl 10A such as weight 408A illustrated in FIG. 53.

Referring to FIG. 38, bowl 10A is adapted so that outer housing 100A, cores 200A and 201A, lower plate 300A and upper plate 299A, housing floor 180A, external conduits 20A and connection sleeve 500A, and lumens 400A and 400B are in connection and rotate together. Housing floor 180A of outer housing 100A comprises recesses 181A on its top surface and these recesses are shaped to fit protrusion 301A of lower plate 300A. As shown, lower plate 300A has round protrusion 301A on its bottom surface 300C to restrict movement of lower plate 300A with respect to housing floor 180A. When assembled, each single protrusion 301A on the bottom surface of lower plate 300A forms a tight fit with recess 181A on housing floor 180A. Thus, when outer housing 100A is rotated, external conduit 20A and connection sleeve 500A, top core 200A, upper plate 299A, bottom core 201A, lower plate 300A, housing floor 180A, and lumens 400A and 400B will rotate therewith.

As illustrated in FIG. 38 lumen 400A allows whole blood 800 to come into bowl 10A via a first bowl channel 420A. First bowl channel 420A provides a passageway for inflow of fluid 800 through lumen 400A to indention 186A and then to the separation volume 220A through channel 305A. Lumen 400A is located inside top core 200A. Lumen 400A has a height from upper lumen end 480A and lower lumen end 402C. Lumen 400A is formed by the connection of channel wall 401A extending from the inner surface 481C of lumen connector 481A and channel wall 402A extending from the top surface 298A of upper plate 299A. Channel wall 401A is supported by a plurality of fins 251A which are attached to the inner wall surface 210C of the outer core wall 210A and inner surface 205C of the upper core end 205A, and channel wall 402A is supported by a plurality of fins 403A (FIG. 40). It can readily be seen that height of lumen 400A can be adjusted by changing the sizes and shapes of core 200A, channel wall 401A, channel wall 402A, conduit wall 325A, and the height of conduit wall 324A.

As illustrated in FIG. 38, lumen 400A, from upper lumen end 480A to lower lumen end 402C, encloses an inner lumen 400B. Lower lumen end 402C has an opening 303A which is in fluid communication with separation volume 220A through a number of channel 305A. In the illustrated embodiment lumen 400A comprises first bowl channel 420A. Second bowl channel 410A is located inside first bowl channel 420A of the top core 200A and is enclosed therein from lumen end 480A and to lumen 402C. Furthermore, second bowl channel 410A forms a passageway through lumen 400B from below lower plate 300A for the removal of a first separated fluid component 810 that gathers in indentation 185A of housing floor 180A. Second bowl channel 410A extends from housing floor 180A of outer housing 100A through lumen 400B and to conduit channel 760A of external conduit 20A.

Referring FIG. 38 (shown without conduit 321C), inner lumen 400B allows red blood cells 810 to exit bowl 10A via a second bowl channel 410A that provides fluid communication from the housing floor above indentation 185A to opening 324E. Inner lumen 400B has an upper conduit end 325C and a lower conduit end 324B and comprises two conduit walls 324A and 325A which are connected in a fluid tight manner and form second bowl channel 410A that has a smaller diameter than and is separate and distinct from first bowl channel 420A. Conduit wall 325A is supported by a fin 251A that extends through channel wall 401A and attaches to conduit wall 325A. Unlike lumen 400A which has one end near indentation 186A, lumen 400B extends beyond indentation 186A and through bottom plate 300A. The first conduit wall 325A has an upper end 325C which has an opening 325D on the top surface 482A of lumen connector 481A and a lower end 325B having an opening 325E adapted to fit tightly with upper end 324C of conduit wall 324A. Upper end 324C of conduit wall 324A is higher than indentation 186A and has an opening 324D. Conduit wall 324A also has end lower end 324B and is supported by a plurality of fins 252A. Lower end 324B having opening 325E is adapted to connect to conduit 320A having opening 302A located near the center of lower plate 300A. The connection of openings 325E and 302A provide fluid communication between lumen 400B and the space 220C between lower plate 300A and housing floor 180A. The space 220C between lower plate 300A and housing floor 180A in turn has fluid communication with separation volume 220A.

Conduit 320A provides a tight fit with lower end 324B, providing support for second bowl channel 410A. Each bowl channel 420A and 410A may be made of any type of flexible or rigid tubing (such as medical tubing) or other such device providing a sealed passageway, possibly for pressurized or unpressurized fluid flow, and which preferably can be disposable and sterilizable, i.e., of simple and efficient manufacture.

1. Drive Tube

As illustrated in FIGS. 39A and 39B, conduit assembly 860A is attached to bowl 10A via connection sleeve 500A which is attached onto the first end 861A of external conduit 20A having a first conduit channel 780A, a second conduit channel 760A, and a third conduit channel 770A. Each conduit channel has fluid communication with a first bowl channel 420A, a second bowl channel 410A, and a bowl chamber 740A. The three conduit channels are equally spaced 120° apart and equal in diameter in external conduit 20A (See FIG. 50). When fluidly connect to external conduit 20A and bowl 10A, conduit channel 780A is fluidly connected with first bowl channel 420A for inflowing fluid 800 from external conduit 20A into bowl 10A for separation. Similarly, second conduit channel 760A fluidly connects to second bowl channel 410A for removing first separated fluid component 810 from bowl 10A into external conduit 20A. Finally, third conduit channel 770A connects to bowl chamber 740A for removing second separated fluid component 820 from bowl 10A.

Figure 45:
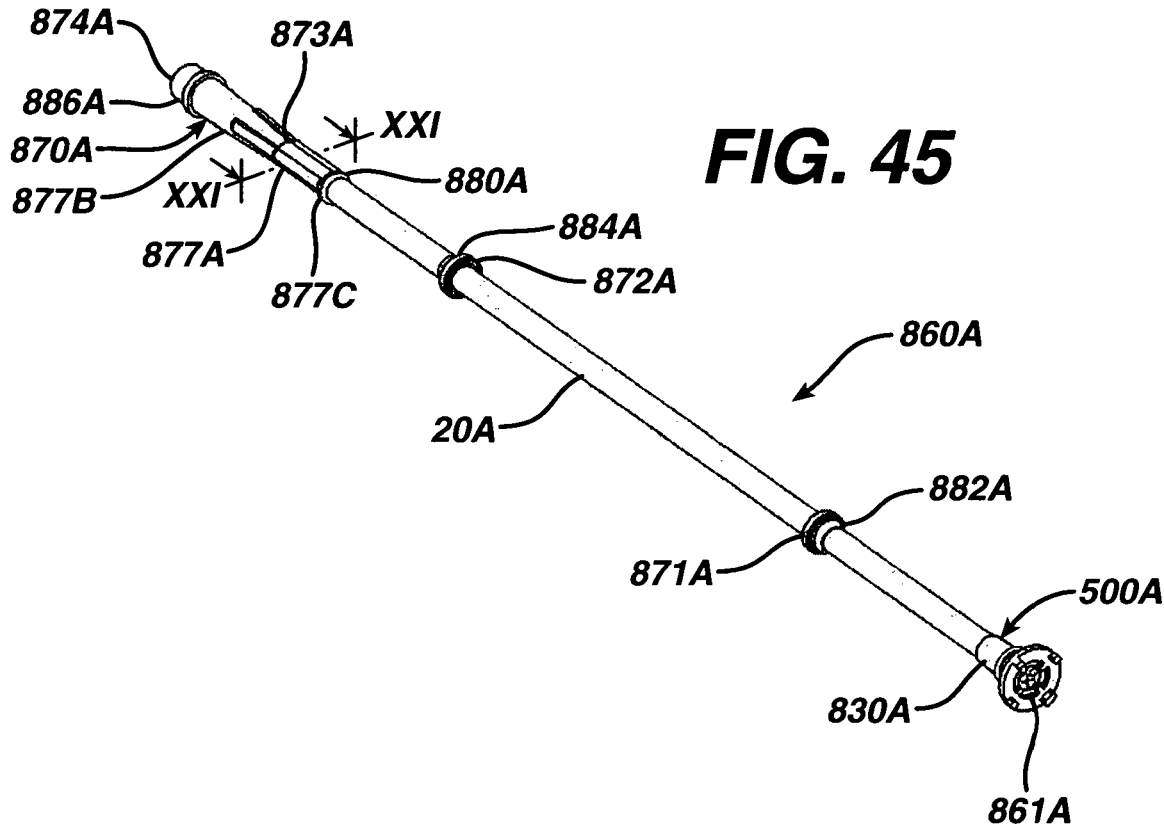
FIG. 45 shows a dimensional view of another embodiment of a conduit assembly.

As is illustrated in FIG. 45, external conduit 20A has a connection sleeve 500A on the first end 861A and an anchor sleeve 870A on the second end 862A of external conduit 20A. Optionally present between the connection sleeve 500A and the anchor sleeve 870A on external conduit 20A are a first shoulder 882 and a second shoulder 884 which extend perpendicularly from the external conduit 20A and are of a larger diameter. Between the connection sleeve 500A and anchor sleeve 870A (or if present the first and second shoulder 882, 884) are a first and second bearing rings 871A and 872A. External conduit 20A, anchor sleeve 870A, and connection sleeve may be prepared from the same or different biocompatible materials of suitable strength and flexibility for use in this type of tubing in a centrifuge (one such preferred material is HYTREL®). The connection sleeve 500A and the anchor sleeve 870A may be attached through any suitable means such as adhesives, welding etc., however, for ease of manufacture it is preferred that the connection sleeve 500A and the anchor sleeve 870A be overmolded to the external conduit 20A.

Figure 48:
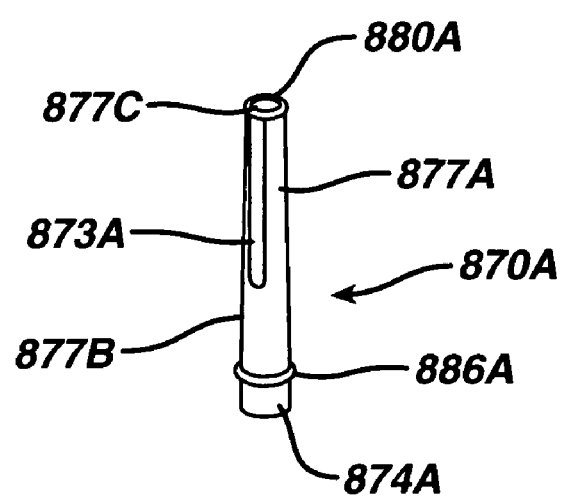
FIG. 48 shows a dimensional view of an anchor end of the present invention.
Figure 49:
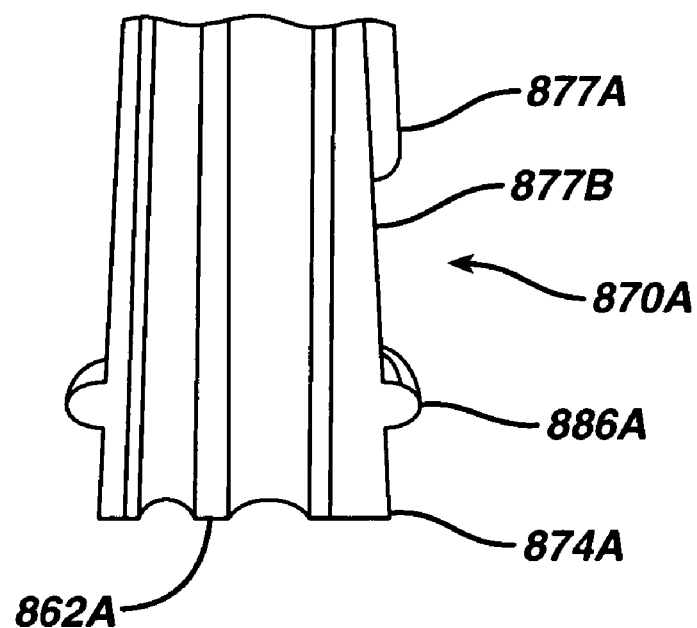
FIG. 49 shows a lateral cross-sectional view of an anchor end.
Figure 50:
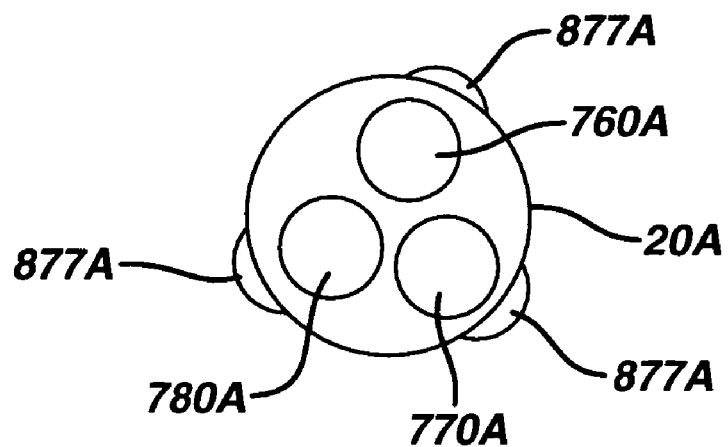
FIG. 50 shows a horizontal cross-sectional view of an anchor end taken along line XXI.

Referring to FIGS. 45, 48 and 49 anchor sleeve 870A comprises a body 877B having a first anchor end 873A and second anchor end 874A. Anchor sleeve 870A is attached to second conduit end 862A of external conduit 20A (preferably by overmolding) and increases in diameter from first collar 873A to the collar 874A. Spaced distally from second end 874A is a collar 886A, which extends perpendicularly from body 877B and of a larger diameter than the body 877B of the anchor sleeve 870A. A plurality of ribs 877A having a first rib end 877B between the collar 886A and second anchor end 873A and a second rib end 877C extending beyond the first anchor end 873A are attached to the body 877B. The second rib ends 877C are joined together by a ring 880A, which is also attached to external conduit 20A. The ribs 877A run parallel to the external conduit 20A and are preferably placed over the region where conduit channels 760A, 770A, and 780A, are closest to the surface of the external conduit 20A (FIG. 50). The regions where the conduit channels 760A, 770A and 780A are closest to the outside diameter of external conduit 20A unless reinforced tend to fail during high speed rotation. Having ribs parallel with the conduit channels beyond the anchor sleeve end 873A provides reinforcement to this region and prevents conduit failure at high speed rotation. In one aspect, the ribs prevent the buckling of the external conduit 20A in this region and act as structural elements to transfer the torsional stress to the anchor sleeve 870A.

Figure 46:
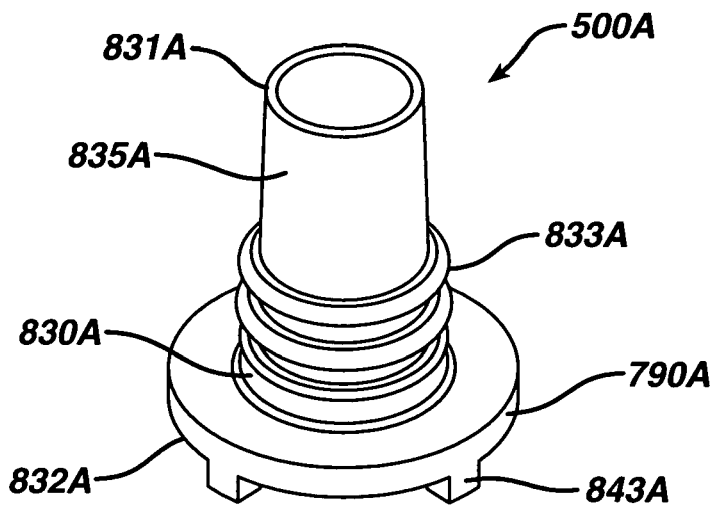
FIG. 46 shows a dimensional view of the connection sleeve of FIG. 45.
Figure 47:
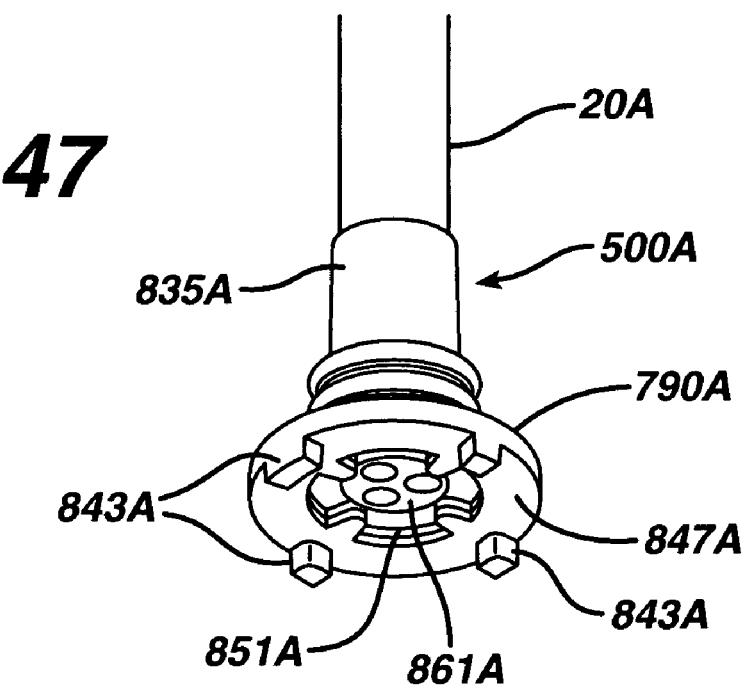
FIG. 47 shows a dimensional view of one end of conduit assembly of FIG. 45.

Connection sleeve 500A comprises body 830A having an upper sleeve end 831A and lower sleeve end 832A (FIGS. 46 and 47). Lower sleeve end 832A has sleeve flange 790A and a plurality of protrusions 843A, which are sized to engage indentations 484A on the wall surface 482A of lumen connector 481A. When the bowl 10A is assembled, a fluid tight seal may be provided by placing o-ring 791A around body 830A and compressing the o-ring 791A between flange 790A and housing 100A. Upper sleeve end 831A is adapted to be secured to external conduit 20A. Referring to FIG. 46, 39A and 39B, connection sleeve 500A is secured to bowl 10A by means of sleeve flange 790A and is adapted to fluidly connect conduit channels 780A, 760A, 770A of external conduit 20A to bowl channels 420A and 410A, and chamber 740A of bowl 10A. When assembled, connection sleeve 500A is mounted to lumen connector 481A (FIGS. 39A and 39B).

Connection sleeve 500A preferably increases in diameter from upper sleeve end 831A to lower sleeve end 832A and is overmolded to first conduit end 861A of external conduit 20A. Connection sleeve 500A connects bowl 10A to external conduit 20A without use of a rotatable seal, which would otherwise normally be located between bowl 10A and connection sleeve 500A. The seal-less connection between bowl 10A and connection sleeve 500A may occur as explained above or alternatively through use of, for example, an O-ring, a groove, or lip, grommet-type connection, welding, or a tight fit with or without adhesive in either bowl 10A or connection sleeve 500A.

As illustrated in FIG. 46 and 39B, sleeve flange 790A has a bottom surface 847A that contacts with top surface 482A of lumen connector 481A forming a tight seal. However, lumen connector 481A has a plurality of indentation 483A that provides for fluid communication between separation chamber 220A and bowl chamber 740A, which, in turn has fluid communication with conduit channel 770A. Bowl chamber 740A is defined by lumen mounting recess 851A and top surface 482A of lumen connector 481A, excluding the space occupied by hollow cylinders 321A and 322A. A plurality of protrusions 843A on the bottom surface 847A of sleeve flange 790A engages and slides into indentations 484A on the wall surface 482B of lumen connector 481A, thus providing a tight fit.

Connection sleeve 500A helps to secure external conduit 20A to bowl 10A, thus fluidly connecting external conduit 20A to bowl 10A. This fluid connection enables fluid 800 to be supplied through external conduit 20A to bowl 10A. Similarly, this fluid connection also enables separated fluid components b, 820 to be removed from bowl 10A through external conduit 20A.

External conduit 20A has an approximately constant diameter which helps to reduce the rigidity. An excessively rigid external conduit 20A will heat up and fail more quickly. Additionally, a constant diameter conduit is cheap/easy to manufacture, allows easy experimentation with connection sleeve 500A and anchor sleeve 870A sizes, and allows bearing rings 871A, 872A to be easily slid thereon. Preferably the movement of bearings 871A and 872A will be constrained by first and second shoulders 882A and 884A. External conduit 20A may be made of any type of flexible tubing (such as medical tubing) or other such device providing a sealed passageway for the flow of fluids, which may be pressurized, into or out of a reservoir of any sort, and which preferably can be disposable and sterilizable.

II. Permanent Tower System

FIG. 17 illustrates tower system 2000. Tower system 2000 is the permanent (i.e., non-disposable) piece of hardware that receives the various devices of photopheresis kit 1000, such as, cassette 1100, irradiation chamber 700, and centrifuge bowl 10 (FIG. 1). Tower system 2000 performs the valving, pumping, and overall control and drive of fluid flow through disposable photopheresis kit 1000. Tower system 2000 performs all of the necessary control function automatically through the use of a properly programmed controller, for example a processor or IC circuit, coupled to all of the necessary components. While a new disposable kit must be discarded after each photopheresis therapy session, tower system 2000 is used over and over again. Tower system 2000 can be modified to perform a number of extracorporeal blood circuit treatments, for example apheresis, by properly programming the controller or by changing some of its components.

Tower system 2000 has a housing having an upper portion 2100 and a base portion 2200. Base portion 2200 has a top 2201 and a bottom 2202. Wheels 2203 are provided at or near the bottom 2202 of base portion 2200 so that tower system 2000 is mobile and can easily be moved from room to room in a hospital setting. Preferably, the front wheels 2203 are pivotable about a vertical axis to allow ease in steering and maneuvering tower system 2000. Top 2201 of base portion 2200 has a top surface 2204 having control deck 1200, best illustrated in FIG. 22, built therein (see FIG. 22). In FIG. 17, cassette 1100 is loaded onto control deck 1200. Base portion 2200 also has hooks (not illustrated), or other connectors, to hang plasma collection bag 51 and treatment bag 50 therefrom. Such hooks can be located anywhere on tower system 2000 so long as their positioning does not interfere with the functioning of the system during therapy. Base portion 2200 has photoactivation chamber 750 (FIG. 18) located behind door 751. Additional hooks (not illustrated) are provided on tower system 2000 for hanging saline and anticoagulant bags. Preferably, these hooks are located on upper portion 2100.

Photoactivation chamber 750 (FIG. 18) is provided in base portion 2200 of tower system 2000 between top 2201 and bottom 2202 behind door 751. Door 751 is hingedly connected to base portion 2200 and is provided for access to photoactivation chamber 750 and to allow the operator to close photoactivation chamber 750 so that UV light does not escape into the surrounding during treatment. Recess 752 is provided to allow tubes 1112, 1117 (FIG. 1) to pass into photoactivation chamber 750 when irradiation chamber 700 is loaded and when door 751 is closed. The photoactivation chamber is discussed in detail below with respect to FIGS. 16 and 18.

Upper portion 2100 is located atop base portion 2200. Centrifuge chamber 2101 (FIG. 19) is located in upper portion 2100 behind centrifuge chamber door 2102. Centrifuge chamber door 2102 has a window 2103 so an operator can see in centrifuge chamber 2101 and monitor for any problems. Window 2103 is constructed with glass thick enough to withstand any forces that may be exerted on it from an accident during centrifugation which can rotate the centrifuge bowl at speeds greater than 4800 RPMs. Preferably, window 2103 is constructed of shatter-proof glass. Door 2102 is hingedly connected to upper portion 2100 and has an automatic locking mechanism that is activated by the system controller during system operation. Centrifuge chamber 2101 is discussed below in more detail with respect to FIG. 19.

Preferably, deck 1200 is located on top surface 2204 of base portion 2200 at or near the front of system tower 2000 while upper portion 2100 is extending upward from base portion 2200 near the rear of tower system 2000. This allows the operator easy access to control deck 1200 while simultaneously affording the operator access to centrifuge chamber 2101. By designing tower system 2000 to have the centrifuge chamber 2101 in the upper portion 2100 and having the photoactivation chamber 750 and deck 1200 in base portion 2200, an upright configuration is achieved. As such, system tower 2000 has a reduced footprint size and takes up a reduced amount of valuable hospital floor space.

The height of system tower 2000 remains below sixty inches so that one view is not obstructed when transporting the machine around the hospital form the rear. Additionally, having deck 1200 in a fairly horizontal position will provide the operator with a place to set devices of photopheresis kit 1000 during the loading of other devices, facilitating easy loading. Tower system 2000 is robust enough to withstand forces and vibrations brought on by the centrifugation process.

A monitor 2104 is provided on centrifuge chamber door 2102 above window 2103. Monitor 2104 has a display area 2105 for visually displaying data to an operator, such as, for example, user interfaces for data entry, loading instructions, graphics, warnings, alerts, therapy data, or therapy progress. Monitor 2104 is coupled to and controlled by the system controller. A data card receiving port 2001 is provided on a side of monitor 2104. Data card receiving port 2001 is provided to slidably receive data card 1195 which is supplied with each disposable photopheresis kit 1000 (FIG. 1). As mentioned above, data card 1195 can be pre-programmed to store serve a variety of data to supply to the system controller of tower system 2000. For example, data card 1195 can be programmed to relay information so that the system controller can ensure: (1) that the disposable photopheresis kit is compatible with the blood drive equipment into which it is being loaded; (2) that the photopheresis kit is capable of running the desired treatment process; (3) that the disposable photopheresis kit is of a certain brand name or make. Data card receiving port 2001 has the necessary hardware and circuitry to both read data from, and write data to, data card 1195. Preferably, data card receiving port 2201 will record treatment therapy data to data card 1195. Such information can include for example, collection times, collection volumes, treatment times, volumetric flow rates, any alarms, malfunctions, disturbances in the process, or any other desired data. While data card receiving port 2001 is provided on monitor 2104, it can be located anywhere on tower system 2000 so long as it is coupled to the system controller or other appropriate control means.

A. Photoactivation Chamber for Receiving Irradiation Chamber

Referring now to FIGS. 16 and 18, photoactivation chamber 750 is illustrated in cross section. Photoactivation chamber 750 is formed by housing 756. Housing 756 fits within base portion 2200 of tower system 2000 behind door 751 (FIG. 17). Photoactivation chamber 750 has a plurality of electrical connection ports 753 provided on back wall 754. Electrical connection ports 753 are electrically coupled to a source of electrical energy. Photoactivation chamber 750 is designed to receive UVA light assembly 759 (FIG. 16). When fully loaded into photoactivation chamber 750, electrical contacts (not illustrated) located on contact wall 755 of UVA light assembly 759 form an electrical connection with electrical connection ports 753. This electrical connection allows electrical energy to be supplied to UVA lamps 758 so that they can be activated. Preferably, three electrical connection ports are provided for each set of UVA lamps 758. More preferably, UVA light assembly 759 has two sets of UVA lamps 758 forming a space which irradiation chamber 700 can be inserted. The supply of electrical energy to UVA lamps 758 is controlled by the properly programmed system controller using a switch. UVA lamps 758 are activated and deactivated as necessary by the controller during the photopheresis therapy session.

Vent hole 757 is provided in the top of housing 756 near back wall 754 of photoactivation chamber 750. Vent hole 757 connects to vent duct 760 which leads out of the back of tower system 2000. When heat generated by UVA lamps 758 builds up in photoactivation chamber 750 during a treatment therapy, this heat escapes photoactivation chamber 750 via vent hole 757 and vent duct 760. The heat exits tower system 2000 through tower housing hole 761 located in the rear of tower system 2000, away from the patient and the operator.

Figure 20:
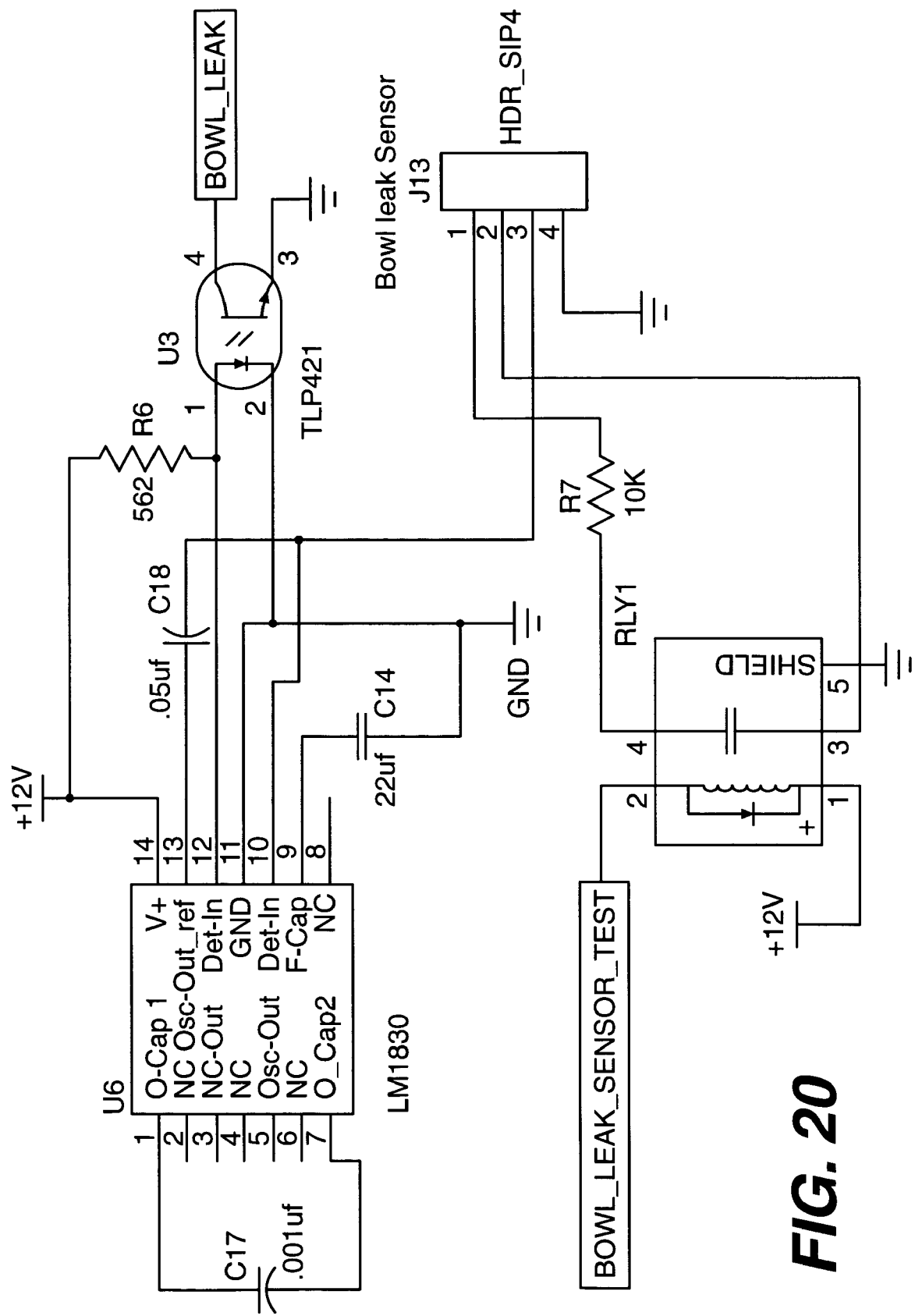
FIG. 20 is an electrical schematic of the leak detection circuit provided in the photoactivation chamber of FIG. 18.

Photoactivation chamber 750 further comprises tract 762 for receiving irradiation chamber 700 and holding irradiation in an upright position between UVA lamps 758. Tract 762 is at or near the bottom of photoactivation chamber 750. Preferably, a leak detector circuit 763 is provided below tract 762 to detect any fluid leaks irradiation chamber 700 during, before, or after operation. Leak detector circuit 762 has two electrodes patterned in a U shape located on an adhesive backed flex circuit. The electrodes are designed to allow for application of a short circuit to test for discontinuities. One end of each electrode goes to an integrated circuit while the other end of each electrode is tied to a solid-state switch. The solid-state switch can be used to check for continuity of the electrodes. By closing the switch the electrodes are shorted to one another. The integrated circuit then detects the short. Closing the switch causes a situation equivalent to the electrodes getting wet (i.e., a leak). IN If the electrodes are damaged in any way, the continuity check will fail. This is a positive indication that the electrodes are not damaged. This test can be performed each time at system start-up or periodically during normal operation to ensure that leak detection circuit 762 is working properly. Leak detection circuit 762 helps ensure that leaks do not go unnoticed during an entire therapy session because the leak detection circuit is damaged. An electrical schematic of leak detector circuit 762 is provided in FIG. 20.

B. Centrifuge Chamber

Figure 19:
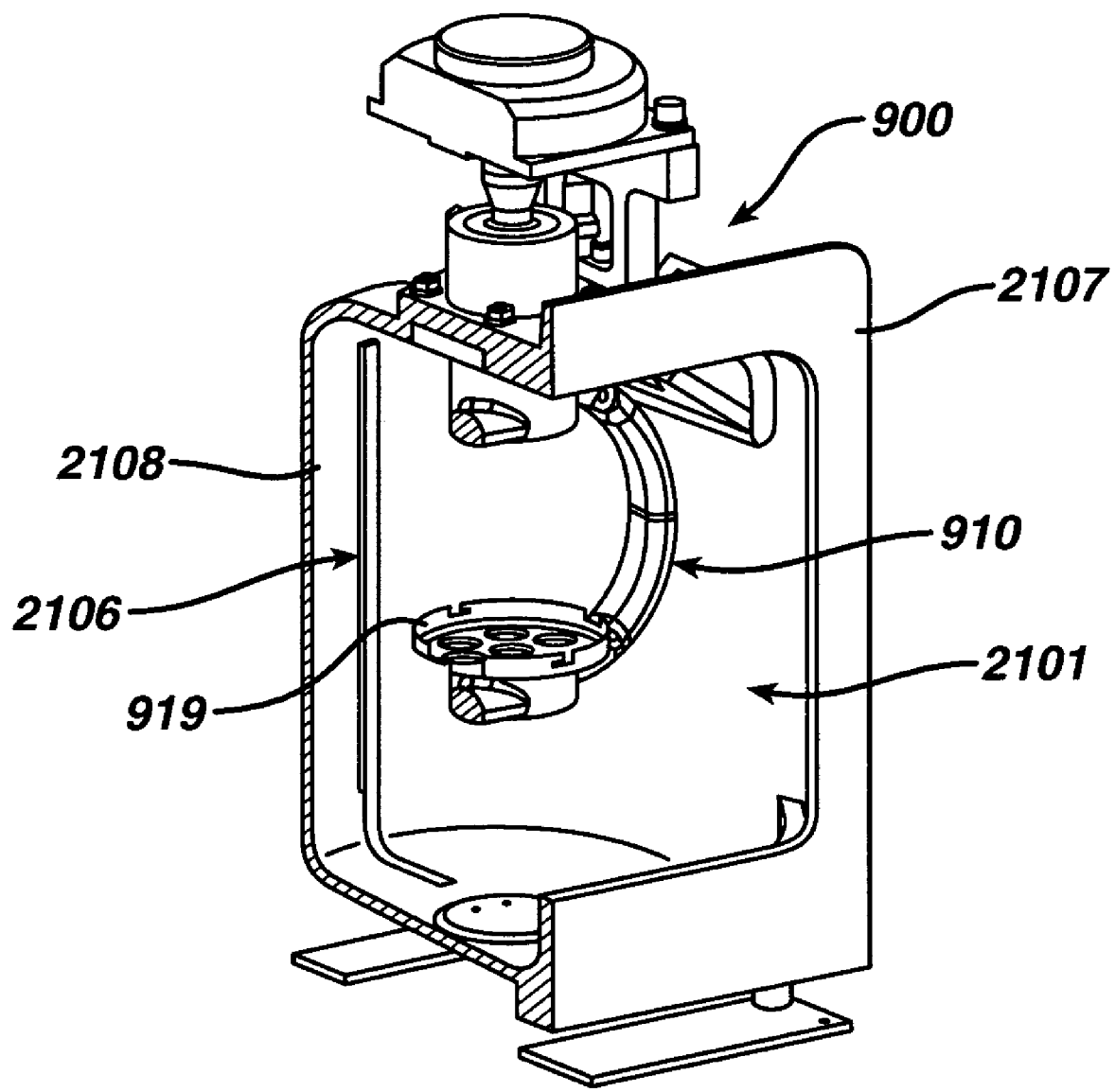
FIG. 19 is a cross-sectional view of an embodiment of the centrifuge chamber used in the tower system of FIG. 17.

FIG. 19 illustrates centrifuge chamber 2101 in cross section with the housing of tower system 2000 removed. Rotational device 900 (also in cross-section) capable of utilizing 1-omega 2-omega spin technology is positioned within centrifuge chamber 2101. Rotational device 900 includes a rotating bracket 910 and a bowl holding plate 919 for rotatably securing centrifuge bowl 10 (FIG. 1). Housing 2107 of centrifuge chamber 2101 is preferably made of aluminum or some other lightweight, sturdy metal. Alternatively, other rotational systems may be used within tower system 2000 such as that described in U.S. Pat. No. 3,986,442, which is expressly incorporated herein by reference in its entirety.

Figure 21:
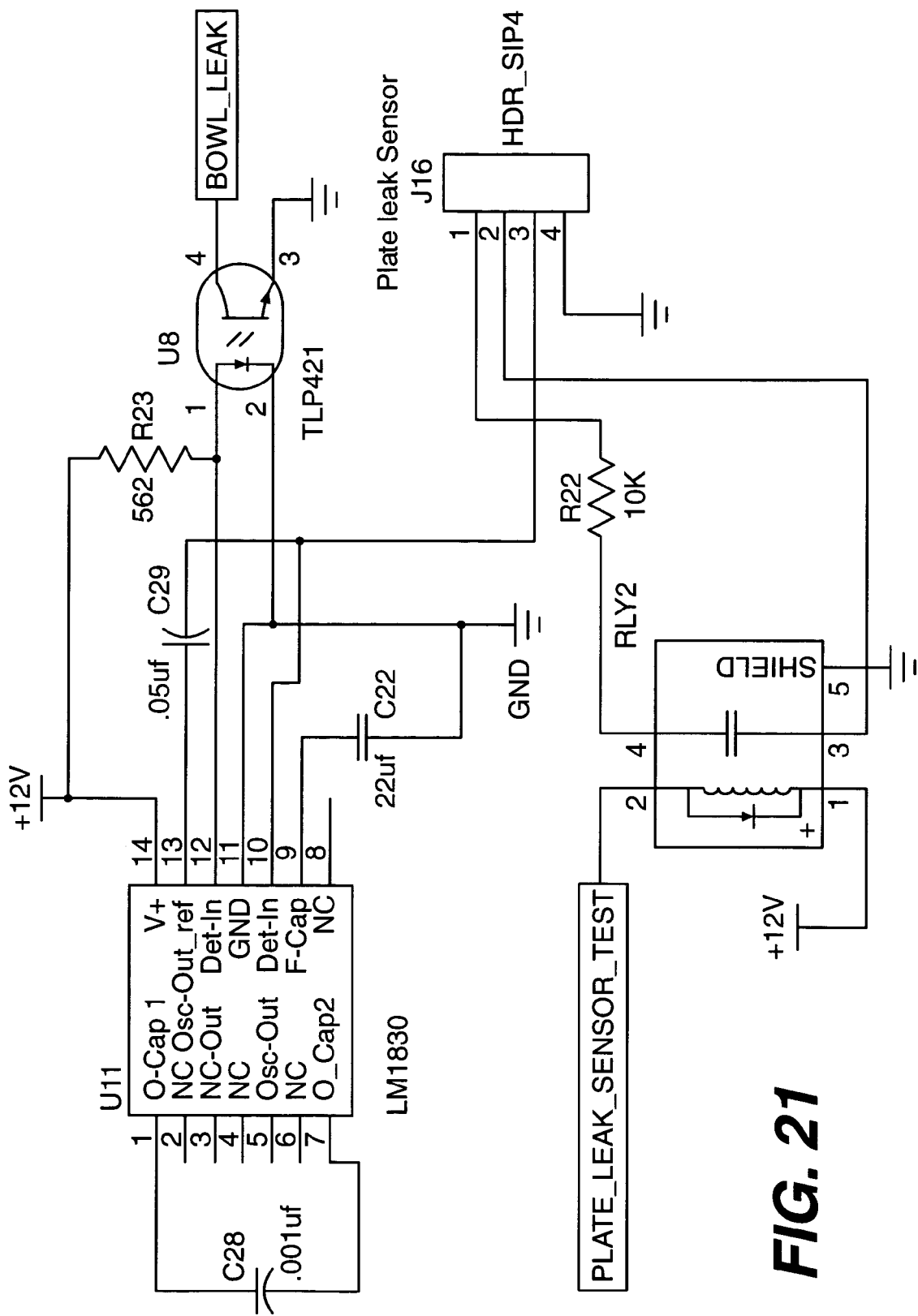
FIG. 21 is an electrical schematic of the leak detection circuit provided in the centrifuge chamber of FIG. 19.

Leak detection circuit 2106 is provided on back wall 2108 of housing 2107. Leak detection circuit 2106 is provided to detect any leaks within centrifuge bowl 10 or the connecting tubes during processing. Leak detection circuit 2106 is identical to leak detector circuit 762 described above. An electrical schematic of leak detection circuit 2106 is provided in FIG. 21.

C. Fluid Flow Control Deck

FIG. 22 illustrates control deck 1200 of tower system 2000 (FIG. 17) without a cassette 1100 loaded thereon. Control deck 1200 performs the valving and pumping so as to drive and control fluid flow throughout photopheresis kit 1000. Preferably, deck 1200 is a separate plate 1202 that is secured to base portion 2200 of tower system 2000 via screws or other securing means, such as, for example, bolts, nuts, or clamps. Plate 1202 can be made of steel, aluminum, or other durable metal or material.

Deck 1200 has five peristaltic pumps, whole blood pump 1301, return pump 1302, recirculation pump 1303, anticoagulant pump 1304, and red blood cell pump 1305 extending through plate 1202. Pumps 1301–1305 are arranged on plate 1202 so that when cassette 1100 is loaded onto deck 1200 for operation, pump loop tubes 1120–1124 extend over and around pumps 1301–1305 (FIG. 25).

Air bubble sensor assembly 1204 and HCT sensor assembly 1205 are provided on plate 1202. Air bubble sensor assembly 1204 has three trenches 1206 for receiving tubes 1114, 1106, and 1119 (FIG. 25). Air bubble sensor assembly 1204 uses ultrasonic energy to monitor tubes 1114, 1106, and 1119 for differences in density that would indicate the presence of air in the liquid fluids normally passing therethrough. Tubes 1114, 1106, and 1119 are monitored because these lines go to the patient. Air bubble sensor assembly 1204 is operably coupled and transmits data to the system controller for analysis. If an air bubble is detected, the system controller will shut down operation and prohibit fluid flow into the patient by occluding tubes 1114, 1106, and 1109 by moving compression actuators 1240–1242 to a raised position, thereby compressing tubes 1114, 1106, and 1119 against cassette 1100 as discussed above and/or shutting down the appropriate pump. HCT sensor assembly 1205 has trench 1207 for receiving HCT component 1125 of tube 1116. HCT sensor assembly 1205 monitors tube 1116 for the presence of red blood cells by using a photoelectric sensor. HCT sensor assembly 1205 is also operably coupled to and transmits data to the system controller. Upon HCT sensor assembly 1205 detecting the presence of red blood cells in tube 1116, the system controller will take the appropriate action, such as stopping the appropriate pump or activating one of compression actuators 1243–1247, to stop fluid flow through tube 1116.

Deck 1200 also has five compression actuators 1243–1247 and three compression actuators 1240–1242 strategically positioned on plate 1202 so that when cassette 1100 is loaded onto deck 1200 for operation, each of compression actuators 1240–1247 are aligned with corresponding apertures 1137 and 1157. Compression actuators 1240–1247 can be moved between a lowered position and a raised position. As illustrated in FIG. 22, compression actuators 1243–1247 are in the lowered position and compression actuators 1240–1242 are in the raised position. When in a raised position, and when cassette 1100 is loaded onto deck 1200 as illustrated in FIG. 25, compression actuators 1240–1247 will extend through the corresponding apertures 1137 or 1157 and compress the portion of flexible tubing that is aligned with that aperture, thereby pinching the flexible tube shut so that fluid can not pass. When in the lowered position, compression actuators 1240–1247 do not extend through apertures 1137 and 1157 and thus do compress the flexible tubing.

Compression actuators 1243–1247 are spring retracted so that their default position is to move to the lowered position unless activated. Compression actuators 1243–1247 are independently controlled and can be raised r lowered independent of one another. Compression actuators 1240–1242 on the other hand are coupled together. As such, when one compression actuator 1240–1242 is lowered or raised, the other two compression actuators 1240–1242 are also lowered in raised accordingly. Additionally, compression actuators 1240–1242 are spring loaded so that their default position is to move to the raised position. Thus, if the system loses power during a therapy session, compression actuators 1240–1242 will automatically move to the raised position, occluding tubes 1114, 1106, and 1119 and preventing fluids from entering or leaving the patient.

Figure 23:
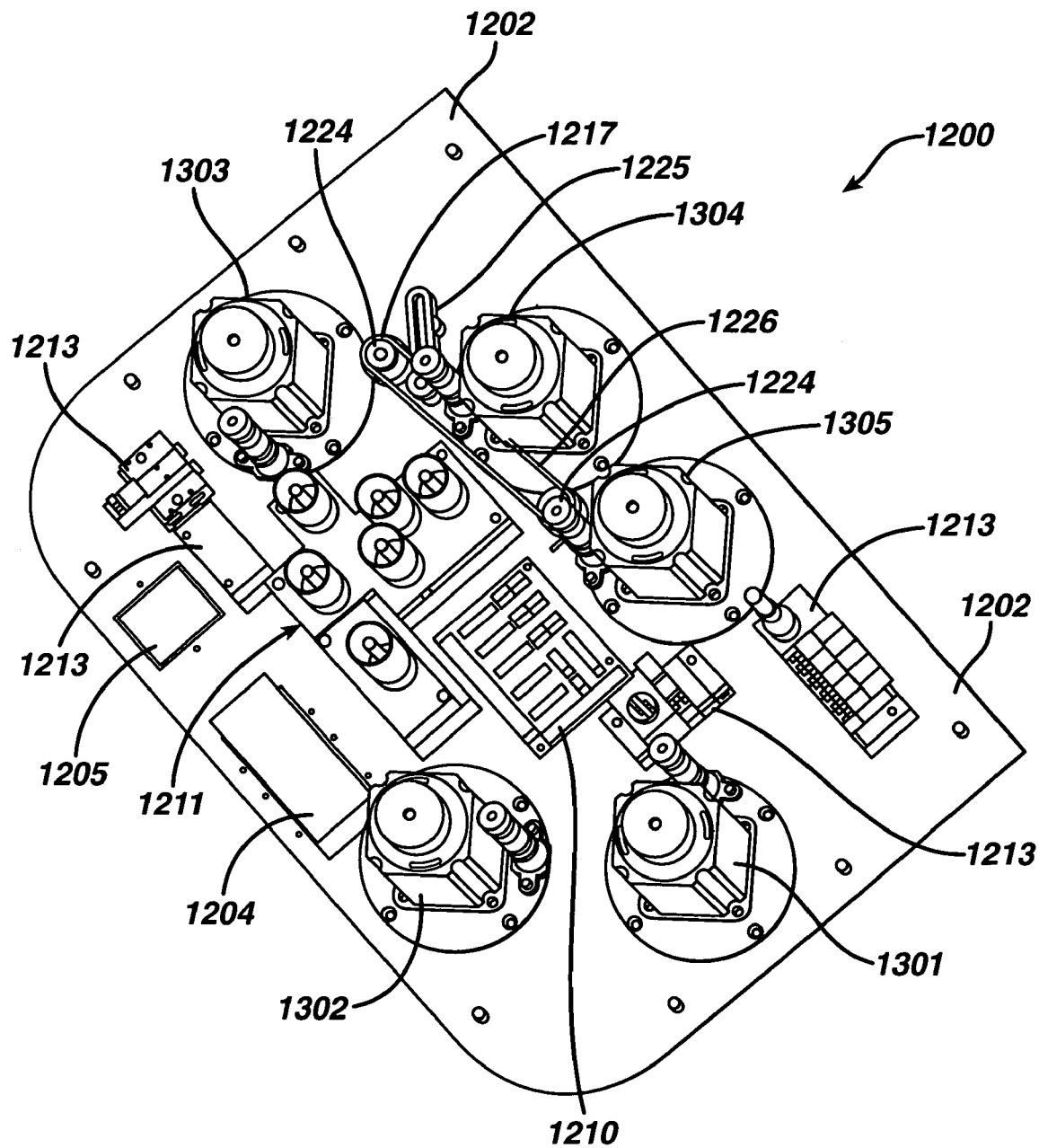
FIG. 23 is a perspective bottom view of the control deck of FIG. 22.
Figure 24:
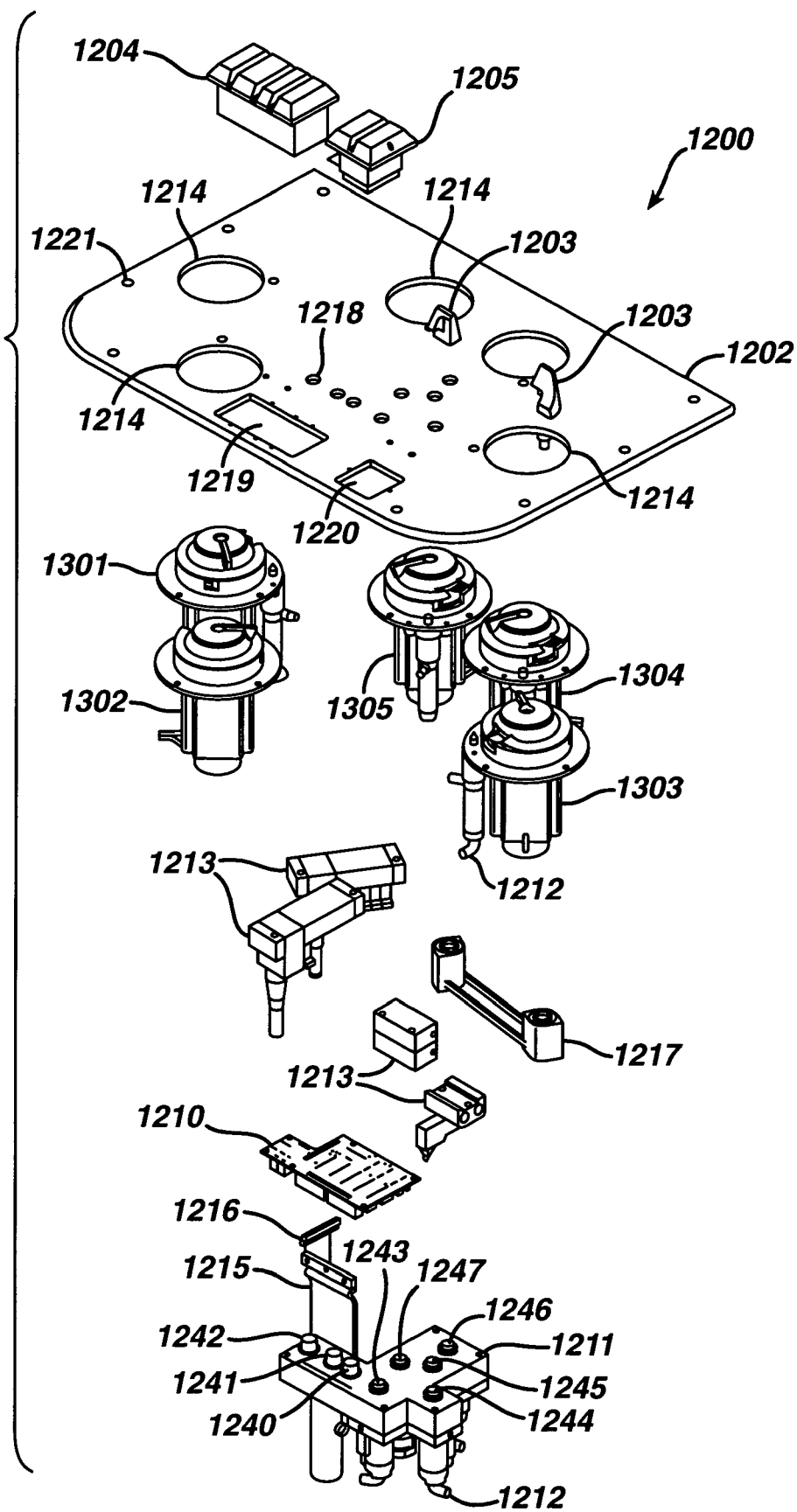
FIG. 24 is an exploded view of the control deck of FIG. 22.

Referring now to FIGS. 23 and 24, deck 1200 further includes system controller 1210, cylinder assembly 1211, manifold assemblies 1213, pump cable 1215, pump motor cable 1216, and timing belt assembly 1217. System controller 1210 is a properly programmed integrated circuit that is operably coupled to the necessary components of the system to perform all of the functions, interactions, decisions, and reaction discussed above and necessary to perform a photopheresis therapy according to the present invention. Cylinder assembly 1211 couples each of compression actuators 1240–1247 to a pneumatic cylinder. Air ports 1212 are provided on the various elements of deck 1200 as necessary to connect air lines to the devices and the appropriate one of manifolds 1213. As such, air can be provided to the devices as necessary to actuate the necessary component, such as compression valves 1240–1247. All of these functions and timing are controlled by system controller 1210. Timing belt assembly 1217 is used to coordinate the rotation of rotating clamps 1203. Finally, plate 1202 includes a plurality of holes 1215, 1219, 1220, 1221, and 1218 so that the various components of deck 1200 can be properly loaded into and so that deck 1200 can be secured to tower system 2000. Specifically, pumps 1301–1305 fit into holes 1314, HCT sensor assembly 1205 fits into hole 1220, air bubble detector assembly 1204 fits into hole 1219, compression actuators 1240–1247 extend through holes 1218, and bolts extend through holes 1221 to secure deck 1200 to tower assembly 2000.

1. Cassette Clamping Mechanism

Referring now to FIGS. 22 and 25, the method by which cassette 1100 is loaded and secured to deck 1200 will now be discussed. In order for system 2000 to perform a photopheresis therapy, cassette 1100 must be properly loaded onto deck 1200. Because of the compression actuator valving system incorporated in the present invention, it is imperative that cassette 1100 be properly secured to deck 1200 and not shift or become dislodged when compression actuators 1240–1247 occlude portions of the flexible tubing by compressing the flexible tubing against cover 1130 of cassette 1100 (FIG. 3). However, this requirement competes with the desired goals of ease in loading cassette 1100 onto deck 1200 and reducing operator errors. All of these goals are achieved by the below described cassette clamping mechanism.

In order to facilitate clamping of cassette 1100 to deck 1200, deck 1200 is provided with two catches 1208 and two rotating clamps 1203 and 1223. Catches 1208 have a slot 1228 near the middle of the top plate. Catches 1208 are secured to plate 1202 at predetermined positions so that the spacing between them is substantially the same as the spacing between tabs 1102 and 1103 on cassette 1100 (FIG. 2). Rotating clamps 1203 and 1223 are illustrated in a closed position. However, rotating clamps 1203 and 1223 can be rotated to an open position (not illustrated) manually or through the automatic actuation of a pneumatic cylinder. Rotating clamps 1203 and 1223 are spring loaded by torque springs so as to automatically return to the closed position when additional torque is not being applied. Rotating clamps 1203 and 1223 are linked together by timing belt assembly 1217 (FIG. 24).

Referring now to FIG. 23, timing belt assembly 1217 comprises timing belt 1226, torque spring housings 1224, and tension assembly 1225. Timing belt assembly 1217 coordinates the rotation of rotational clamps 1203 and 1223 so that if one is rotated, the other also rotates in the same direction and the same amount. In other words, rotational clamps 1203 and 1223 are coupled. Tension assembly 1217 ensures that timing belt 1226 is under sufficient tension to engage and rotate the rotational clamp 1203 or 1223 that is being coordinated. Torque spring housings 1224 provide casings for the torque springs that torque rotational clamps 1203 and 1223 to the closed position.

Referring back to FIGS. 22 and 25, when loading cassette 1100 onto deck 1200, cassette 1100 is placed at an angle to deck 1200 and tabs 1102 and 1103 (FIG. 2) are aligned with catches 1208. Cassette 1100 is moved so that tabs 1102 and 1103 slidably insert into catches 1208. Rotational clamps 1203 and 1223 are in the closed position at this time. The rear of the cassette 1100 (i.e. the side opposite the tabs 1102 and 1103) contacts rotational clamps 1203 and 1223 as tabs 1102 and 1103 are being inserted in catches 1108. As force is applied downward on cassette 1100, rotational clamps 1103 and 1123 will be rotated to the open position, allowing the rear of cassette 1100 to move downward to a position below ledges 1231 of rotational clamps 1203 and 1223. Once cassette 1100 is in this position, the rotational clamps 1203 and 1223 spring back from the force applied by the torque springs and rotate back to the closed position, locking cassette 1100 in place. When in the locked position, cassette 1100 can resist upward and lateral forces.

To remove cassette 1110 after the therapy session is complete, rotational clamps 1203 and 1223 are rotated to the open position either manually or automatically. Automatic rotation is facilitated by an air cylinder that is coupled to an air line and system controller 1210. Once rotational clamps 1203 and 1223 are in the open position, cassette 1100 is removed by simple lifting and sliding tabs 1102 and 1103 out of catches 1208.

2. Self-Loading Peristaltic Pumps

Referring to FIG. 24, peristaltic pumps 1301–1305 are provided on deck 1200 and are used to drive fluids through photopheresis kit 1000 (FIG. 1) along desired pathways. The activation, deactivation, timing, speed, coordination, and all other functions of peristaltic pumps 1301–1305 are controlled by system controller 1210. Peristaltic pumps 1301–1305 are identical in structure. However, the placement of each peristaltic pump 1301–1305 on deck 1200 dictates the function of each peristaltic pump 1301–1305 with respect to which fluid is being driven and along which pathway. This is because the placement of peristaltic pumps 1301–1305 dictates which pump loop 1220–1224 will be loaded therein.

Figure 28:
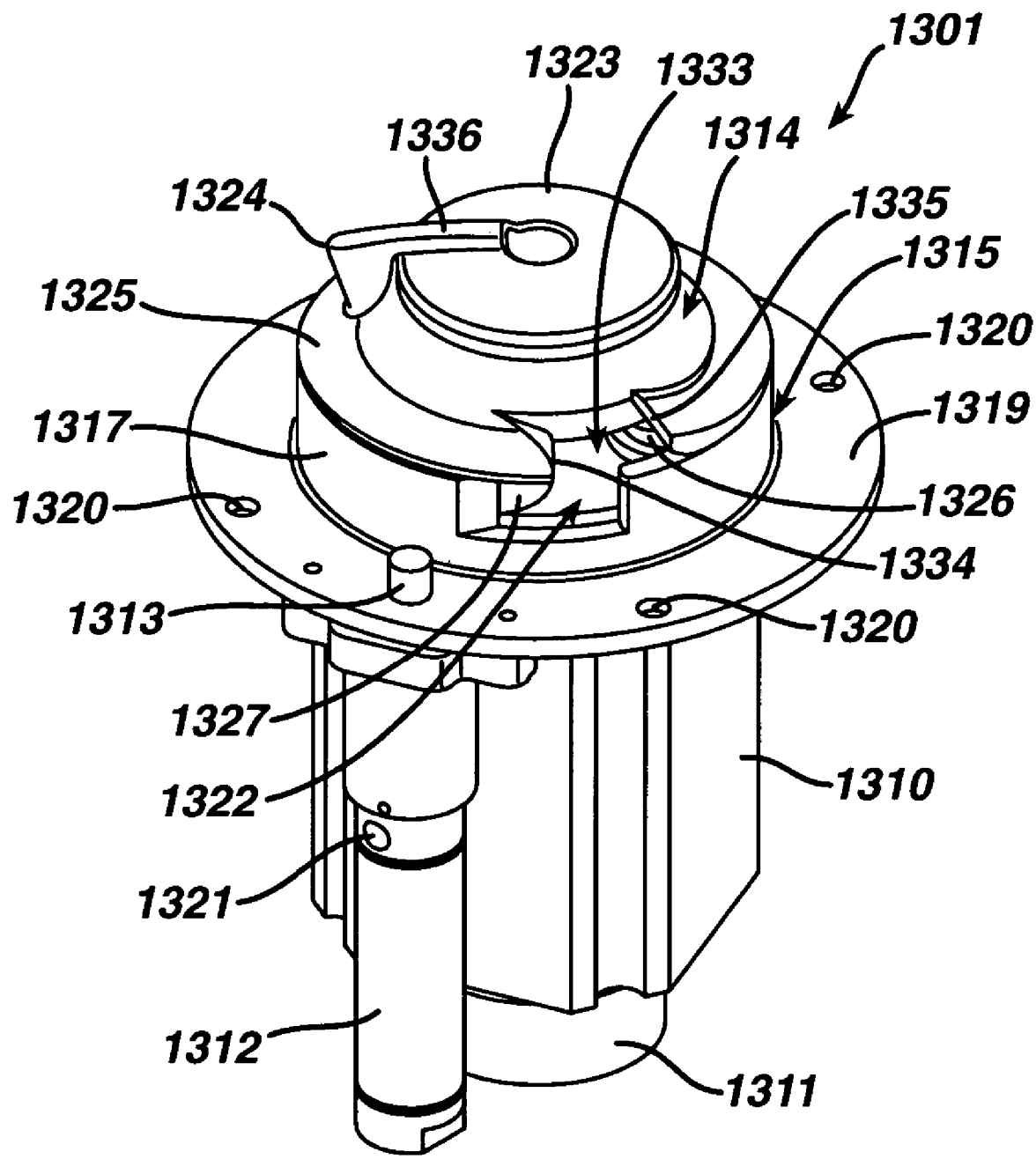
FIG. 28 is top perspective view an embodiment of a peristaltic pump.
Figure 29:
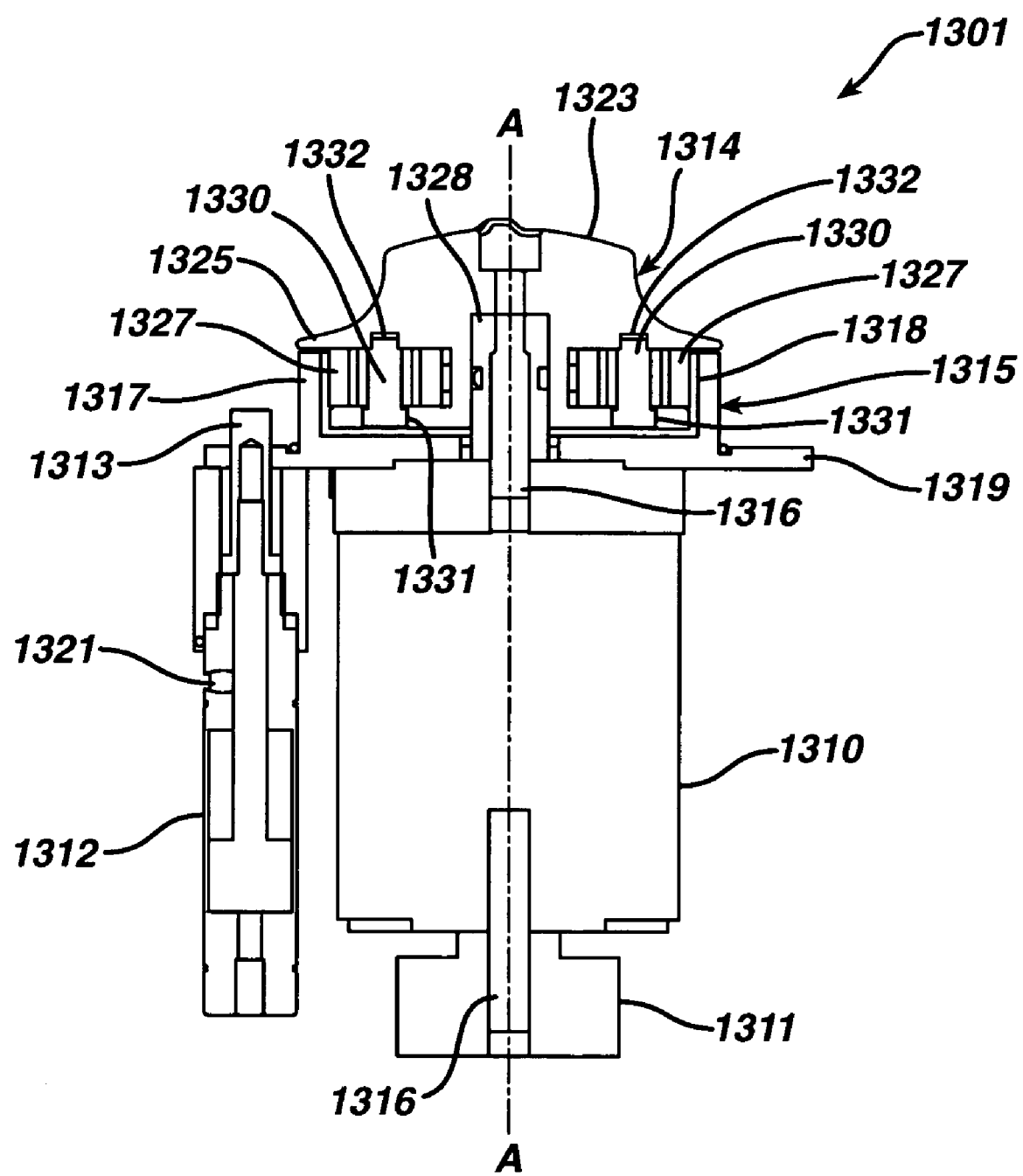
FIG. 29 is a cross sectional side view of the peristaltic pump of FIG. 28.

Referring now to FIGS. 28 and 29, whole blood pump 1301 is illustrated in detail. The structure and functioning of whole blood pump will be described with the understanding that peristaltic pumps 1302–1305 are identical. Whole blood pump 1301 has motor 1310, position sensor 1311, pneumatic cylinder 1312, pneumatic actuator 1313, rotor 1314 (best illustrated in FIG. 30), and housing 1315.

Rotor 1314 is rotatably mounted within housing 1315 and is in operable connection with drive shaft 1316 of motor 1310. Specifically, rotor 1314 is mounted within curved wall 1317 of housing 1315 so as to be rotatable by motor 1310 about axis A—A. When rotor 1314 is mounted in housing 1315, a space 1318 exists between rotor 1314 and curved wall 1317. This space 1318 is the tube pumping region of whole blood pump 1301 into which pump loop tube 1121 (FIG. 33) fits when loaded for pumping. Position sensor 1316 is coupled to drive shaft 1316 of motor 1310 so that the rotational position of rotor 1314 can be monitored by monitoring drive shaft 1316. Position sensor 1311 is operably connected to and transmits data to system controller 1210 (FIG. 24). By analyzing this data, system controller 1210, which is also coupled to motor 1310, can activate motor 1310 to place rotor 1314 in any desired rotational position.

Housing 1315 also includes a housing flange 1319. Housing flange 1319 is used to secure whole blood pump 1310 to plate 1202 of deck 1200 (FIG. 22). More specifically, a bolt is extended through bolt holes 1320 of housing flange 1319 to threadily engage holes within plate 1202. Housing flange 1319 also includes a hole (not shown) to allow pneumatic actuator 1313 to extend therethrough. This hole is sized so that pneumatic actuator 1313 can move between a raised and lowered position without considerable resistance. Pneumatic actuator 1313 is activated and deactivated by pneumatic cylinder 1312 in a piston-like manner through the use of air. Pneumatic cylinder 1312 comprises air inlet hole 1321 for connecting an air supply line. When air is supplied to pneumatic cylinder 1312, pneumatic actuator extends upward through housing flange 1319 to a raised position. When air ceases to be supplied to pneumatic cylinder 1312, pneumatic actuator retracts back into pneumatic cylinder 1312, returning to the lowered position. System controller 1210 (FIG. 22) controls the supply of air to air inlet hole 1321.

Curved wall 1317 of housing 1315 contains two slots 1322 (only one visible). Slots 1322 are located on substantially opposing sides of curved wall 1317. Slots 1322 are provided for allowing pump loop tube 1121 (FIG. 33) to pass into tube pumping region 1318. More specifically, pump inlet portion 1150 and outlet portions 1151 (FIG. 33) of pump loop tube 1121 pass through slots 1322.

Figure 30:
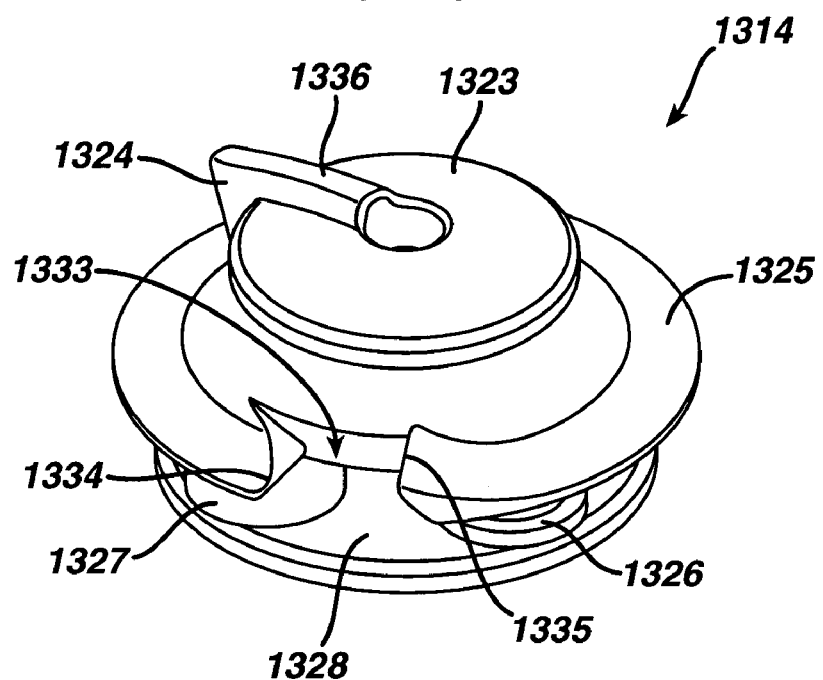
FIG. 30 is a top perspective view the rotor of the peristaltic pump of FIG. 29.
Figure 31:
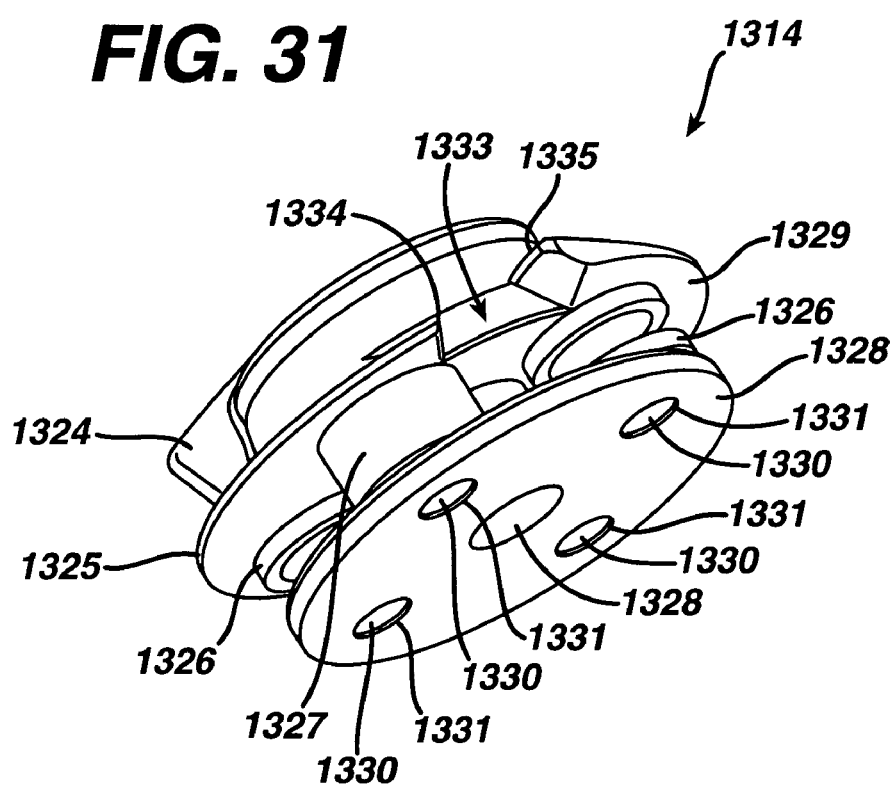
FIG. 31 is a bottom perspective view of the rotor of FIG. 30.

Turning now to FIGS. 30 and 31, rotor 1314 is illustrated as removed from housing 1315 so that its components are more clearly visible. Rotor 1314 has a top surface 1323, angled guide 1324, rotor flange 1325, two guide rollers 1326, two drive rollers 1327, and rotor floor 1328. Guide rollers 1326 and drive rollers 1327 are rotatably secured about cores 1330 between rotor floor 1328 and a bottom surface 1329 of rotor flange 1325. As is best illustrated in FIG. 29, cores 1330 fit into holes 1331 of rotor floor 1328 and recesses 1332 in bottom surface 1329. Guide rollers 1326 and drive rollers 1327 fit around cores 1330 and can rotate thereabout. Preferably, two guide rollers 1326 and two drive rollers 1327 are provided. More preferably, guide rollers 1326 and drive rollers 1327 are provided on rotor 1314 so as to be in an alternating pattern.

Referring to FIGS. 29 and 31, drive rollers 1327 are provided to compress the portion of pump loop tube 1121 that is loaded into tube pumping region 1318 against the inside of curved wall 1317 as rotor 1314 rotates about axis A-A, thereby deforming the tube and forcing fluids to flow through the tube. Changing the rotational speed of rotor 1314 will correspondingly change the rate of fluid flow through the tube. Guide rollers 1326 are provided to keep the portion of pump loop tube 1121 that is loaded into tube pumping region 1318 properly aligned during pumping. Additionally, guide rollers 1326 help to properly load pump tube loop 1121 into tube pumping region 1318. While guide rollers 1326 are illustrated as having a uniform cross-section, it is preferred that the top plate of the guide rollers be tapered so as to come to a sharper edge near its outer diameter. Tapering the top plate results in a guide roller with a non-symmetric cross-sectional profile. The tapered embodiment helps ensure proper loading of the tubing into the tube pumping region.

Rotor 1314 further includes cavity 1328 extending through its center. Cavity 1328 is designed to connect rotor 1314 to drive shaft 1316 of motor 1310.

Figure 32:
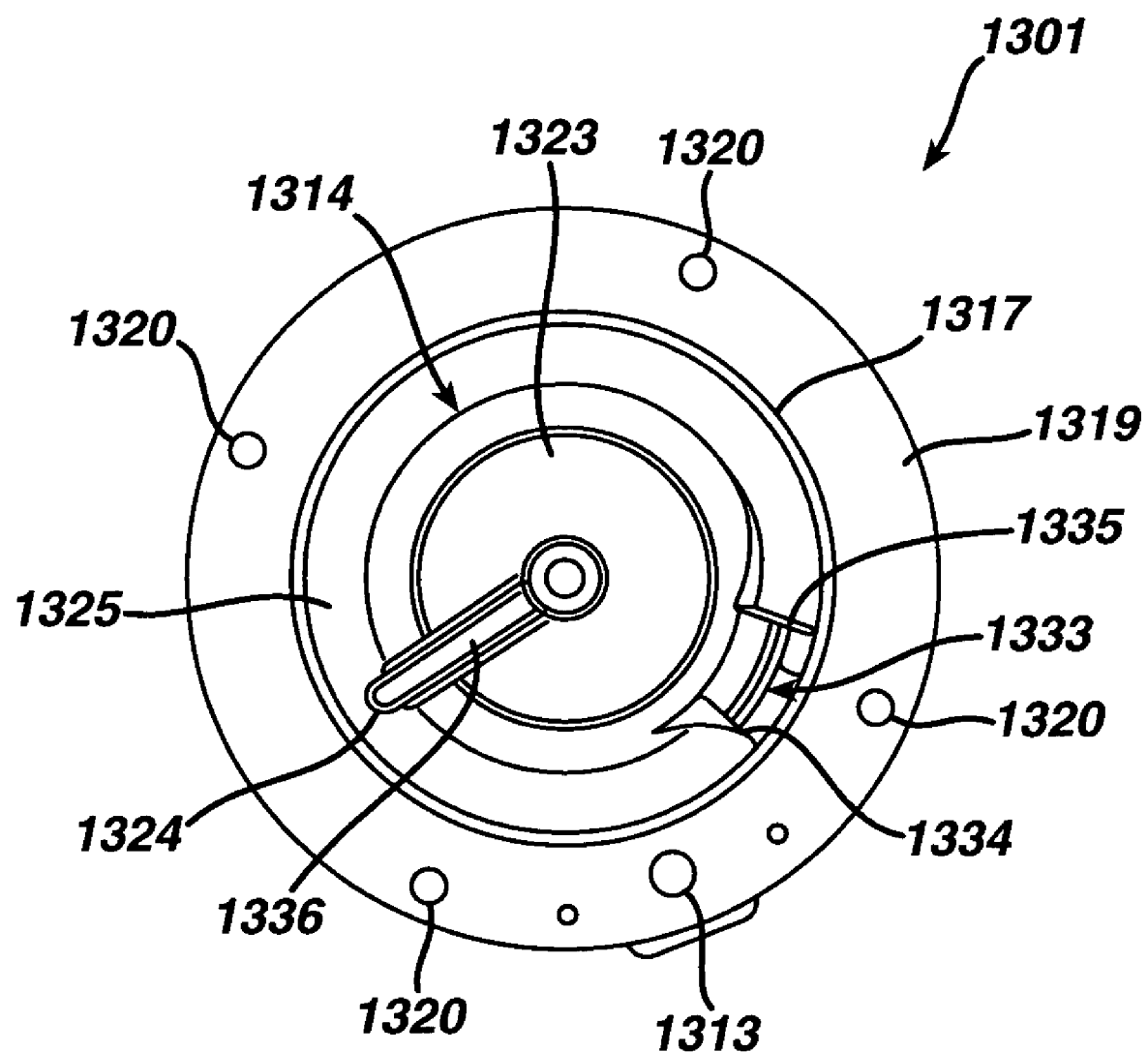
FIG. 32 is a top view of the peristaltic pump of FIG. 28.

Referring now to FIGS. 30 and 32, rotor flange has opening 1333. Opening 1333 is defined by a leading edge 1334 and a trailing edge 1335. The terms leading and trailing are used assuming that rotating rotor 1314 in the clockwise direction is the forward direction while rotating rotor 1314 in a counterclockwise direction is the rearward direction. However, the invention is not so limited and can be modified for counterclockwise pumps. Leading edge 1334 is beveled downward into opening 1333. Trailing edge 1335 extends upward from the top surface of rotor flange 1325 higher than the leading edge 1334. Leading edge is provide for trailing edge for capturing and feeding pump loop tube 1121 into tube pumping region 1318 upon rotor 1314 being rotated in the forward direction.

Rotor 1314 also has angled guide 1324 extending upward, at an inverted angle, from rotor flange 1325. Angled guide 1324 is provided for displacing pump loop tube 1121 toward rotor flange 1325 upon rotor 1314 being rotated in the forward direction. Preferably, angled guide 1324 has elevated ridge 1336 running along top surface 1323 for manual engagement by an operator if necessary. More preferably, angled guide 1314 is located forward of leading edge 1334.

Figure 33:
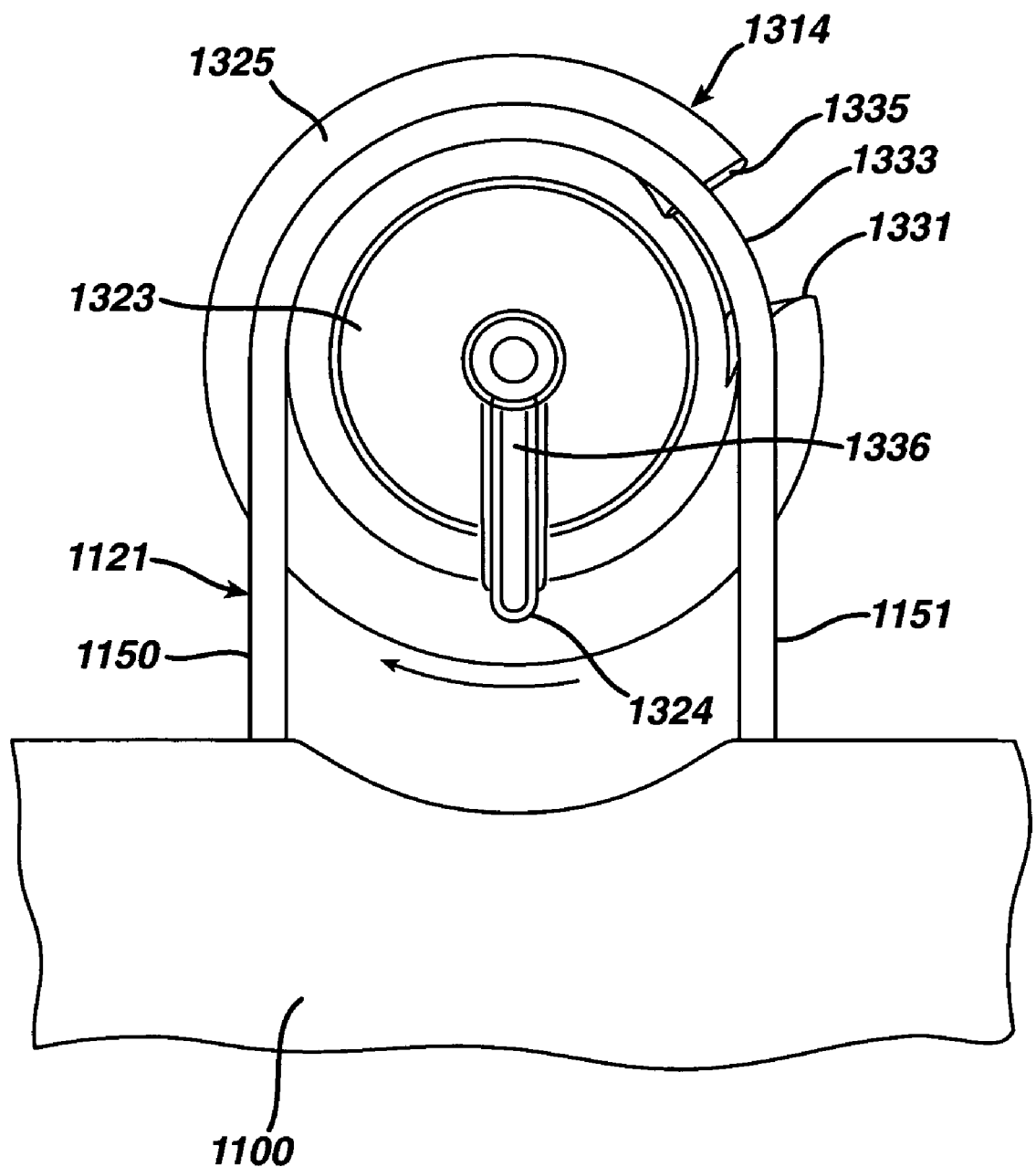
FIG. 33 is a top view of the peristaltic pump of FIG. 28 in a loading position and near the cassette of FIG. 2.

Referring now to FIGS. 28 and 33, whole blood pump 1301 can automatically load and unload pump lop tube 1121 into and out of tube pumping region 1318. Using position sensor 1311, rotor 1314 is rotated to a loading position where angled guide 1324 will face cassette 1100 when cassette 1100 is loaded onto deck 1200 (FIG. 25). More specifically, rotor 1314 is preset in a position so that angled guide 1324 is located between inlet portion 1150 and outlet portion 1151 of pump loop 1121 when cassette 1100 is secured to the deck, as is illustrated in FIG. 13. When cassette 1100 is secured to deck 1200, pump lop tube 1121 extends over and around rotor 1314. Pneumatic actuator 1313 is in the lowered position at this time.

Once cassette 1100 is properly secured and the system is ready, rotor 1314 is rotated in the clockwise direction (i.e., the forward direction). As rotor 1314 rotates, pump tube loop 1121 is contacted by angled guide 1324 and displaces against the top surface of rotor flange 1325. The portions of pump loop tube 1121 that are displaced against rotor flange 1325 are then contacted by trailing edge 1325 and fed downward into tube pumping region 1318 through opening 1333. A guide roller 1326 is provided directly after opening 1333 to further properly position the tubing within tube pumping chamber for pumping by drive rollers 1327. When loaded, inlet portion 1150 and outlet portion 1151 of pump loop tube 1121 pass through slots 1322 of curved wall 1317. One and a half revolutions are needed to fully load the tubing.

To automatically unload pump tube loop 1121 from whole blood pump 1301 after the therapy is complete, rotor 1314 is rotated to a position where opening 1333 is aligned with the slot 1322 through which outlet portion 1151 passes. Once aligned, pneumatic actuator 1313 is activated and extended to the raised position, contacting and lifting outlet portion 1151 to a height above trailing edge 1335. Rotor 1314 is then rotated in the counterclockwise direction, causing trailing edge to 1335 to contact and remove pump loop tube 1121 from tube pumping region 1318 via opening 1333.

D. Infra-Red Communication

Figure 34:
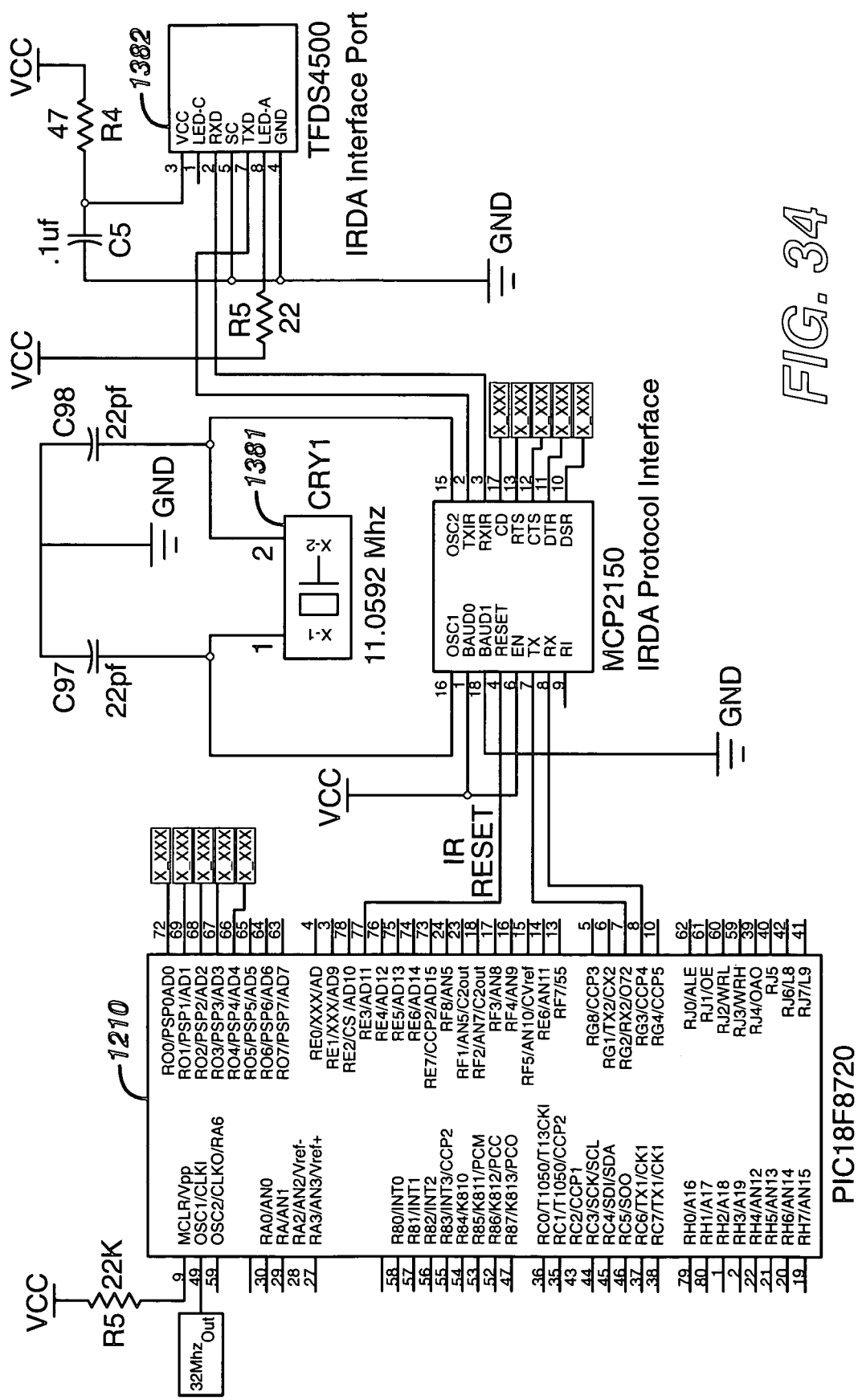
FIG. 34 is an electrical schematic of the infrared communication port circuit.

Referring to FIG. 34, tower system 2000 (FIG. 17) preferably further includes a wireless infrared ("IR") communication interface (not shown). The wireless IR interface consists of three primary elements, system controller 1210, IRDA protocol integrated circuit, 1381, and IRDA transceiver port 1382. The IR communication interface is capable of both transmitting and receiving data via IR signals from a remote computer or other device having IR capabilities. In sending data, system controller 1210 sends serial communication data to the IRDA protocol chip 1381 to buff the data. IRDA protocol chip 1381 adds additional data and other communication information to the transmit string and then sends it to ERDA transceiver 1382. Transceiver 1382 converts the electrical transmit data into encoded light pulses and transmits them to a remote device via a photo transmitter.

In receiving data, IR data pulses are received by a photo detector located on the transceiver chip 1382. The transceiver chip 1382 converts the optical light pulses to electrical data and sends the data stream to IRDA protocol chip 1381 where the electrical signal is stripped of control and additional IRDA protocol content. The remaining data is then sent to the system controller 1210 where the data stream is parsed per the communication protocol.

By incorporating an IR communication interface on tower system 2000 real time data relating to a therapy session can be transmitted to a remote device for recording, analysis, or further transmission. Data can be sent via IR signals to tower system 2000 to control the therapy or allow protocols to be changed in a blinded state. Additionally, IR signals do not interfere with other hospital equipment, like other wireless transmission methods, such as radio frequency.

III. Photopheresis Treatment Process

Figure 26:
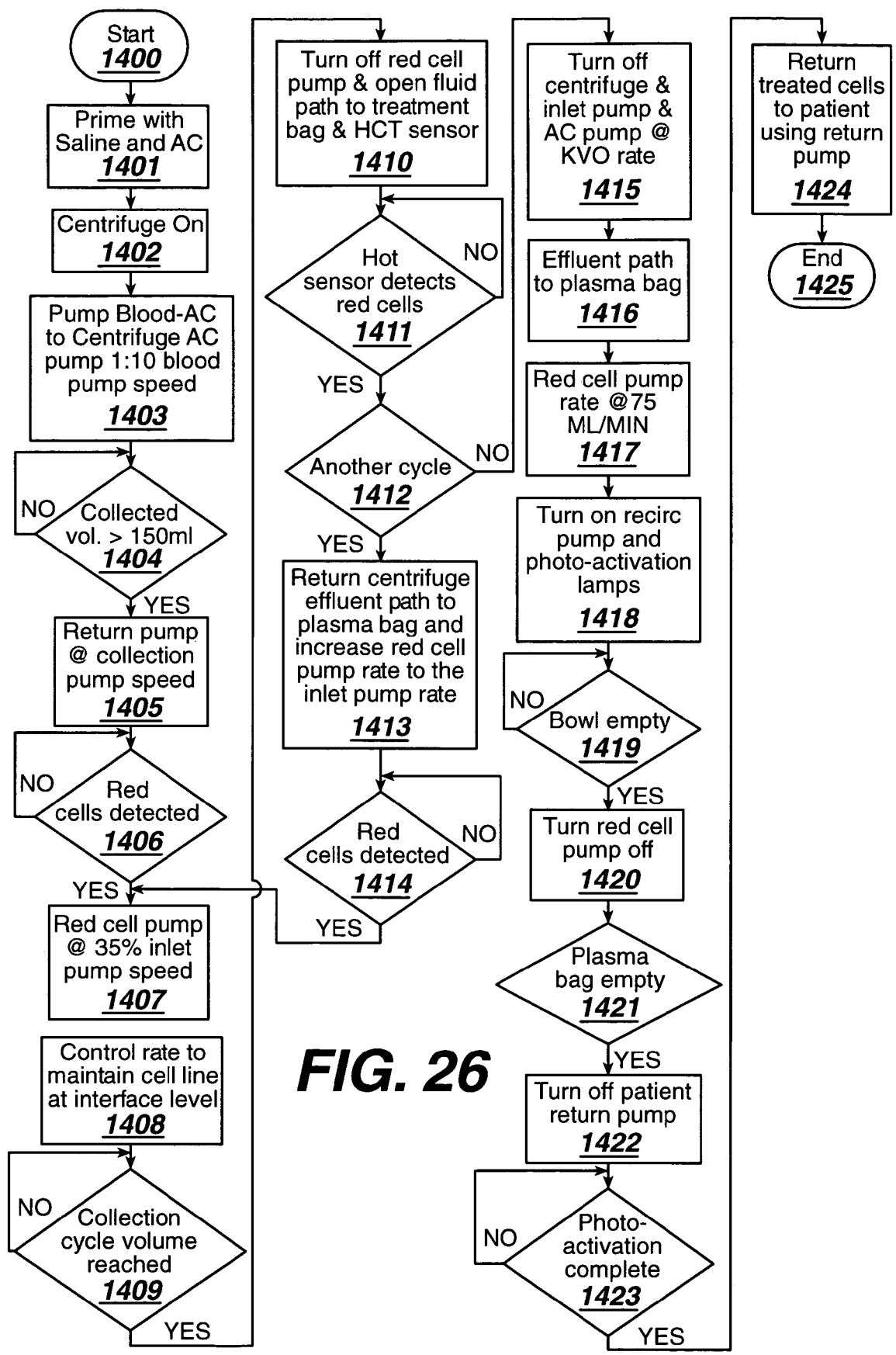
FIG. 26 is a flowchart of an embodiment of a photopheresis treatment process.

Referring together to FIG. 26, a flow chart illustrating an embodiment of the invention which includes photactivation of buffy coat, and FIG. 27, a schematic representation of apparatus which can be employed in such an embodiment, the process starts 1400 with a patient 600 connected by means of a needle adapter 1193 carrying a needle, for drawing blood, and needle adapter 1194 carrying another needle, for returning treated blood and other fragments. Saline bag 55 is connected by connector 1190 and anticoagulant bag 54 is connected by connector 1191. Actuators 1240, 1241, and 1242 are opened, anticoagulant pump 1304 is turned on, and saline actuator 1246 is opened so that the entire disposable tubing set is primed 1401 with saline 55 and anticoagulant 54. The centrifuge 10 is turned on 1402, and blood-anticoagulant mixture is pumped 1403 to the centrifuge bowl 10, with the A/C pump 1304 and WB pump 1301 controlled at a 1:10 speed ratio.

When the collected volume reaches 150 ml 1404, the return pump 1302 is set 1405 at the collection pump 1301 speed until red cells are detected 1406 at an HCT sensor (not shown) in the centrifuge chamber 1201 (FIG. 19). Packed red cells and buffy coat have at this point accumulated in the spinning centrifuge bowl and are pumped out slowly at a rate, controlled by the processor, which maintains the red cell line at the sensor interface level.

The red cell pump 1305 is then set 1407 at 35% of the inlet pump speed while controlling 1408 the rate to maintain the cell line at the interface level until the collection cycle volume is reached 1409, at which point the red cell pump 1305 is turned off 1410 and the fluid path to the treatment bag 50 via the HCT sensor 1125 is opened by lowering actuator 1244, and stops when the HCT sensor 1125 detects 1411 red cells. "Collection cycle volume" is defined as the whole blood processed target divided by the number of collection cycles, for example a white blood process target of 1500 ml may require 6 cycles, and so 1500/6 is a volume of 250 ml. With whole blood continuing at 1410 to be delivered from the patient to the bowl and the red cell pump off, red cells will accumulate and will push out the buffy coat from inside the bowl 10. The red cells are used to push out the buffy coat and will be detected by the effluent hematocrit (HCT) sensor, indicating that the buffy coat has been collected.

If another cycle is needed 1412, the centrifuge 10 effluent path is returned 1413 to the plasma bag 51 and the red cell pump 1305 rate is increased 1413 to the inlet pump 1301 pump rate until red cells are detected 1414, which is the beginning of the second cycle. If another cycle 1412 is not needed, the centrifuge 10 is turned off 1415 and inlet pump 1301 and anticoagulant pump 1304 are set at KVO rate, 10 ml/hr in this embodiment. The effluent path is directed 1416 to the plasma bag 51, the red cell pump 1305 rate is set 1417 at 75 ml/min, the recirculation pump 1303 and photoactivation lamps are turned on 1418 for sufficient period to treat the buffy coat, calculated by the controller depending on the volume and type of disease being treated.

When the bowl 10 is empty 1419, the red cell pump 1305 is turned off 1420 and the plasma bag 51 is emptied 1421 by opening actuator 1247 and continuing return pump 1302. The return pump 1302 is turned off 1422 when the plasma bag 51 is empty and when photoactivation is complete 1423, the treated cells are returned 1424 to the patient from the plate 700 by means of the return pump 1302. Saline is used to rinse the system and the rinse is returned to the patient, completing the process 1425.

The anticoagulant, blood from patient, and fluid back to patient are all monitored by air detectors 1204 and 1202, and the fluid back to the patient goes through drip chamber and filter 1500. The pumps, 1304, 1301, 1302, 1303, and 1305, the actuators 1240, 1241, 1242, 1243, 1244, 1245, 1246, and 1247, and the spinning of the bowl 10 are all controlled by the programmed processor in the tower.

The process and related apparatus have significant advantages over prior processes and apparatus in that the invention allow buffy coat to be in the bowl longer since red cells are being drawn off while collecting buffy coat in the bowl while centrifuging, keeping more buffy coat in the bowl until the desired amount of buffy coat cells are collected prior to withdrawing the collected buffy cells. Platelets, leukocytes, and other buffy coat fractions can also be separated, or red cells can be collected rather than returning them with plasma to the patient as the illustrated process does.

It has been found that increasing the time that buffy coat 810 is subjected to rotational motion in centrifuge bowl 10 yields a "cleaner cut" of buffy coat 820. A "cleaner cut" means that the hematocrit count (HCT %) is decreased. HCT % is the amount of red blood cells present per volume of buffy coat. The amount of time that buffy coat 820 is subjected to rotational motion in centrifuge bowl 10 can be maximized in the following manner. First, whole blood 800 is fed into first bowl channel 420 as centrifuge bowl 10 is rotating. As discussed above, whole blood 800 is separated into buffy coat 820 and RBC's 810 as it moves outwardly atop lower plate 300. Second bowl channel 410 and third bowl channel 740 are closed at this time. The inflow of whole blood 800 is continued until the separation volume 220 is filled with a combination of buffy coat 820 near the top and RBC's 810 near the bottom of centrifuge bowl 10. By removing RBC's 810 from centrifuge bowl 10 via second bowl channel 410 only, additional volume is created for the inflow of whole blood 800 and the unremoved buffy coat 820 is subjected to rotational forces for an extended period of time. As centrifuge bowl 10 continues to rotate, some of the RBC's 810 that may be trapped in buffy coat 820 get pulled to the bottom of centrifuge bowl 10 and away from third bowl channel 740 and buffy coat 820. Thus, when third bowl channel 740 is opened, the buffy coat 820 that is removed has a lower HCT %. By controlling the inflow rate of whole blood 800 and the outflow rates of buffy coat 820 and RBC's 810, a steady state can be reached that yields a buffy coat 820 with an approximately constant HCT %.

The elimination of batch processing and the improved yields achieved by the current invention, have reduced the treatment time necessary to properly treat patients. For an average sized adult, 90–100 milliliters of buffy coat/white blood cells must be captured in order to conduct a full photopheresis treatment. In order to collect this amount of buffy coat/white blood cells, the present invention needs to process around 1.5 liters of whole blood. The required amount of buffy coat/white blood cells can be removed from the 1.5 liters of whole blood in about 30–45 minutes using the present invention, collecting around 60% or more of the total amount of the buffy coat/white blood cells that are subjected to the separation process. The captured buffy coat/white blood cells have an HCT of 2% or less. In comparison, one existing apparatus, the UVAR XTS, takes around 90 minutes to process 1.5 liters of whole blood to obtain the sufficient amount of buffy coat/white blood cells. The UVAR XTS only collects around 50% of the total amount of the buffy coat/white blood cells that are subjected to the separation process. The HCT of the buffy coat/white blood cells collected by the UVAR XTS is around, but not substantially below, 2%. Another existing apparatus, the Cobe Spectra™ by Gambro, must process 10 liters of whole blood in order to collect the sufficient amount of buffy coat/white blood cells. This typically takes around 150 minutes, collecting only 10–15% of the total amount of the buffy coat/white blood cells that are subjected to the separation process, and having an HCT of about 2%. Thus, it has been discovered that while existing apparatus and systems require anywhere from 152 to 225 minutes to separate, process, treat, and reinfuse the requisite amount of white blood cells or buffy coat, the present invention can perform the same functions in less than 70 minutes. These times do not include the patient preparation or prime time. The times indicate only the total time that the patient is connected to the system.

What is claimed is:

1. An apparatus for separating components of a fluid comprising:

an outer housing with an upper housing end and a lower housing end, wherein said outer housing increases in diameter from said upper housing end to said lower housing end, said lower housing end having a housing floor and said housing upper end having a housing outlet;

a base said outer housing and said base having an interior volume between them and said outer housing adapted for rotation about a center axis;

a top core having an outer wall, an upper top core end, and a lower top core end;

said top core connected with said outer housing for rotation therewith; occupying a top coaxial volume of said interior volume of said outer housing; and providing a top separation volume between said top core and said outer housing;

said upper top core end having a lumen connector; said lumen connector having a first lumen wall extending downward from the a top surface of the lumen connector;

said lumen connector further having an inner lumen wall within said first lumen wall and extending downward from the top surface; said inner lumen wall having a top wall end and a bottom wall end;

an upper plate having a top surface, a bottom surface, a second lumen wall extending above said top surface; said upper plate adapted to form a tight fit with the lower top core end for rotation therewith;

said second lumen wall adapted to overlap with said first lumen wall to form a lumen having an upper lumen end and a lower lumen end; said lumen extending axially through said core forming a first bowl channel for inflowing said fluid and said lumen having fluid communication with the separation volume via a trench;

a bottom core having an outer wall, a top surface contacting and connected with bottom surface of upper plate for rotation therewith; an upper bottom core end, a lower bottom core end, said top surface having an indentation and a trench, and a lumen wall that has an upper wall end and a lower wall end; said bottom core occupying a bottom coaxial volume of said interior volume between said outer housing and said base;

said upper wall end of lumen wall is adapted to engage with bottom wall end of inner lumen wall to form an inner lumen having an upper lumen end and a lower lumen end; said inner lumen forming a second bowl channel for removing a first separated fluid component;

a lower plate having a top surface, a bottom surface, and a hollow cylinder near center of said lower plate; said hollow cylinder has an opening adapted to engage with lower wall end of said lumen; and said lower plate having a circumference adapted to form a tight fit with the lower bottom core end for rotation therewith;

a connection sleeve having a sleeve flange surrounding a lumen mounting recess; said lumen mounting recess and top surface of lumen connector engaged to form a bowl chamber for removing a second separated fluid component; said connection sleeve further adapted to be secured to said apparatus near said housing outlet of said outer housing for rotation therewith.

2. The apparatus of claim 1 wherein said outer wall of said top core increases in diameter from said upper end to said lower end.

3. The apparatus of claim 1 wherein said outer wall of said bottom core increases in diameter from said upper end to said lower end.

4. The apparatus of claim 1 wherein said outer wall of said top core increases in diameter from said upper end to said lower end and said outer wall of said bottom core increases in diameter from said upper end to said lower end.

5. The apparatus of claim 1 wherein said lumen having a height and said lumen wall having a height and the height of said lumen is about one third to about four times the height of said lumen wall.

6. The apparatus of claim 5 wherein the height of said lumen and the height of said lumen wall are about the same.

7. The apparatus of claim 1 wherein the top surface of said bottom core has one to 10 trenches.

8. The apparatus of claim 7 wherein the top surface of said bottom core has three to six trenches.

9. The apparatus of claim 1 wherein said connection sleeve is adapted to fluidly connect a first and second bowl channels, and a bowl chamber to a corresponding conduit channel of an external conduit.

10. The apparatus of claim 1 wherein said outer housing comprises a locking mechanism adapted to secure said outer housing to a means for rotating said apparatus.

11. The apparatus of claim 10 wherein said locking mechanism comprises protrusions.

12. The apparatus of claim 11 wherein said locking mechanism comprises a key slot.

13. The apparatus of claim 1 wherein said lower plate is circular.

14. The apparatus of claim 1 wherein said apparatus is adapted for use without a rotatable seal.

15. The apparatus of claim 1 wherein said apparatus is closed to undesired contagions.

16. The apparatus of claim 1 wherein said apparatus is adapted to allow rotation of said upper bottom cores and said lower bottom core, said lower plate, said upper plate, and said outer housing about said lumens.

17. The apparatus of claim 1 further comprising means for rotating said outer housing about said axis.

18. The apparatus of claim 17 wherein said means for rotating comprises a bracket.

19. The apparatus of claim 18 wherein said bracket is adapted to engage and rotate an external conduit that is fluidly connected to said first bowl channel, said second bowl channel, and said bowl chamber.

20. The apparatus of claim 19 wherein said rotation means is adapted to rotate said outer housing and said external conduit using 1-omega/2-omega spin technology.

21. The apparatus of claim 17 further comprising:

means to remove said fluid from a source, said means to remove said fluid fluidly connected to said first bowl channel, means to remove said first separated fluid component via said second bowl channel;

means to remove said second separated fluid component via said bowl chamber; and means to treat said second separated fluid component subsequent to being removed via bowl chamber.

22. The apparatus of claim 21 further comprising means to reinfuse treated second separated fluid component and said first separated fluid component back into said source, wherein said apparatus is a closed-loop apparatus when connected to said source.

23. The apparatus of claim 22 wherein said reinfusion means comprises a needle or catheter.

24. The apparatus of claim 21 further comprising an anticoagulant source fluidly connected between said means to remove said fluid from said source and said first bowl channel.

25. The apparatus of claim 21 wherein said means to remove said fluid from said source comprises a needle or catheter.

26. The apparatus of claim 21 wherein said means to remove said first separated fluid component comprises a pump.

27. The apparatus of claim 21 wherein said treatment means comprises a chamber and a source of ultraviolet radiation.

* * * * *